(12) United States Patent
Tojo et al.

(10) Patent No.: US 8,916,718 B2
(45) Date of Patent: Dec. 23, 2014

(54) COMPOUND HAVING 2-FLUOROPHENYLOXYMETHANE STRUCTURE

(75) Inventors: Kenta Tojo, Kitaadachi-gun (JP); Kiyofumi Takeuchi, Kitaadachi-gun (JP); Masashi Osawa, Kitaadachi-gun (JP); Masakazu Kaneoya, Kitaadachi-gun (JP); Tetsuo Kusumoto, Kitaadachi-gun (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 14/116,709

(22) PCT Filed: May 22, 2012

(86) PCT No.: PCT/JP2012/063011
§ 371 (c)(1),
(2), (4) Date: Apr. 22, 2014

(87) PCT Pub. No.: WO2012/161178
PCT Pub. Date: Nov. 29, 2012

(65) Prior Publication Data
US 2014/0275577 A1 Sep. 18, 2014

(30) Foreign Application Priority Data

May 26, 2011 (JP) ................................. 2011-117918

(51) Int. Cl.
- C07D 407/08 (2006.01)
- C07D 309/06 (2006.01)
- C09K 19/30 (2006.01)
- C09K 19/20 (2006.01)
- C07C 43/225 (2006.01)

(52) U.S. Cl.
CPC .......... C07D 309/06 (2013.01); C09K 19/3066 (2013.01); C09K 19/20 (2013.01); C07C 43/225 (2013.01)
USPC ........................................................ 549/370

(58) Field of Classification Search
USPC ........................................................ 549/370
See application file for complete search history.

(56) References Cited

U.S. PATENT DOCUMENTS

2009/0302273 A1  12/2009  Tanaka

FOREIGN PATENT DOCUMENTS

| JP | 02-501311 A | 5/1990 |
|----|-------------|--------|
| JP | 02-233626 A | 9/1990 |
| JP | 04-501575 A | 3/1992 |
| JP | 06-504032 A | 5/1994 |
| JP | 08-120268 A | 5/1996 |
| JP | 09-157202 A | 6/1997 |
| JP | 10-101599 A | 4/1998 |
| JP | 2000-17263 A | 1/2000 |
| JP | 2002-371033 A | 12/2002 |
| JP | 2005-517079 A | 6/2005 |
| KR | 2006-0119879 A | 11/2006 |
| WO | 98/23564 A1 | 6/1998 |
| WO | 2005/019377 A1 | 3/2005 |

OTHER PUBLICATIONS

International Search Report dated Jul. 31, 2012, issued in corresponding application No. PCT/JP2012/063011.
Chapman, James et al., "Near-UV transparent nematics", Molecular Crystals and Liquid Crystals, 2004, 411, 1091-1098.

*Primary Examiner* — Taofiq A Solola
(74) *Attorney, Agent, or Firm* — Westerman, Hattori, Daniels & Adrian, LLP

(57) ABSTRACT

The present invention relates to a compound having a 2-fluorophenyloxymethane structure and useful for organic electronic materials and medical and agricultural chemicals, particularly materials for liquid crystal display elements.
A problem to be solved by the invention is to provide a compound having relatively large $\Delta\varepsilon$, relatively high $T_{\to i}$, low viscosity ($\eta$), and high miscibility with other liquid crystal compounds, and also provide a liquid crystal composition containing the compound as a constituent component.
The present invention provides a compound having a 2-fluorophenyloxymethane structure and also provides a liquid crystal composition containing the compound and a liquid crystal display device using the liquid crystal composition.

11 Claims, No Drawings

COMPOUND HAVING 2-FLUOROPHENYLOXYMETHANE STRUCTURE

TECHNICAL FIELD

The present invention relates to a compound having a 2-fluorophenyloxymethane structure and useful for organic electronic materials and medical and agricultural chemicals, particularly materials for liquid crystal display elements.

BACKGROUND ART

Liquid crystal display devices have been used for watches and electronic calculators, various measuring apparatuses, automotive panels, word processors, electronic notebooks, printers, computers, televisions, watches, advertising displays, etc. Typical examples of a liquid crystal display mode include a TN (twisted nematic) mode, a STN (super-twisted nematic) mode, a vertical alignment mode and an IPS (in-plane switching) mode using TFT (thin-film transistor), and the like. Liquid crystal compositions used for these liquid crystal display devices are required to have stability to external factors such as moisture, air, heat, light, and the like, exhibit a liquid crystal phase (nematic phase, smectic phase, blue phase, and the like) within as wide a temperature range as possible including room temperature as a center, and have low viscosity and low drive voltage. Further, each of the liquid crystal compositions is composed of several types to several tens types of compounds selected in order to have optimum values of dielectric anisotropy ($\Delta\in$) and refractive index anisotropy ($\Delta n$) for a display device.

A horizontal alignment-mode display, such as a TN mode, a STN mode, an IPS mode, or the like, uses a liquid crystal composition having positive $\Delta\in$. Also, there has been reported a driving method in which a liquid crystal composition having positive $\Delta\in$ is vertically aligned with no voltage applied, and display is performed by applying a transverse electric field, and the need for a liquid crystal composition having positive $\Delta\in$ is further increased. On the other hand, improvement in response speed is required for all driving methods, and a liquid crystal composition having lower viscosity than existing ones is required for solving the problem. In order to produce a liquid crystal composition having low viscosity, it is effective to decrease the viscosity of each of polar compounds constituting a liquid crystal composition. Also, when a liquid crystal composition is used for a display device or the like, it is required that a stable liquid crystal phase is exhibited over a wide temperature range. In order to maintain a liquid crystal phase over a wide temperature range, each of components constituting a liquid crystal composition is required to have high miscibility with other components and high clearing point ($T_{\to i}$).

In order to produce a compound having high $T_{\to i}$, it is generally known to be preferred to introduce three or more ring structures such as a 1,4-cyclohexylene group, a 1,4-phenylene group, or the like. On the other hand, in order to produce a compound having low viscosity, a compound having a plurality of ring structures which are directly bonded to each other without through a linkage group, that is, a compound referred to as a "directly-bonded ring system", is preferred. However, in general, directly-bonded ring-system compounds having three or more ring structures and positive $\Delta\in$ frequently have high crystallinity and low miscibility with a liquid crystal composition. In order to improve the problem, compounds containing various linkage groups introduced therein have been studied. It has been found that viscosity is slightly increased by introducing a linkage group, but miscibility with a liquid crystal composition can be improved (Patent Literatures 1 to 8). However, compounds having a —CH$_2$O— group as a linkage group exhibit high chemical stability and high solubility in liquid crystal compositions but have high viscosity and the problem of significantly decreasing $T_{\to i}$.

CITATION LIST

Patent Literature

PTL 1: Japanese Unexamined Patent Application Publication No. 10-101599
PTL 2: Japanese Unexamined Patent Application Publication (Translation of PCT Application) No. 2-501311
PTL 3: Japanese Unexamined Patent Application Publication No. 9-157202
PTL 4: Japanese Unexamined Patent Application Publication (Translation of PCT Application) No. 2005-517079
PTL 5: Japanese Unexamined Patent Application Publication No. 2-233626
PTL 6: Japanese Unexamined Patent Application Publication (Translation of PCT Application) No. 4-501575
PTL 7: Japanese Unexamined Patent Application Publication (Translation of PCT Application) No. 6-504032
PTL 8: WO98/23564

SUMMARY OF INVENTION

Technical Problem

A problem to be solved by the invention is to provide a compound having relatively large $\Delta\in$, relatively high $T_{\to i}$, low viscosity ($\eta$), and high miscibility with other liquid crystal compounds, and also provide a liquid crystal composition containing the compound as a constituent component and a liquid crystal display device.

Solution to Problem

As a result of study on various compounds in order to solve the problem, the inventors found that the problem can be effectively solved by a compound having a 2-fluorophenyloxymethane structure, leading to the achievement of the present invention.

The present invention provides a compound represented by general formula (1),

[Chem. 1]

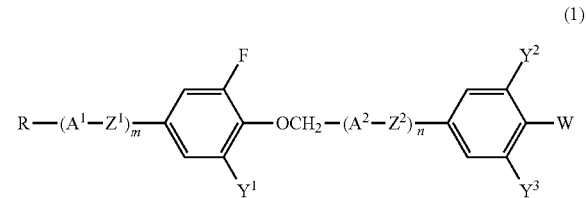

(1)

(in the formula, R represents an alkyl group having 1 to 15 carbon atoms or an alkenyl group having 2 to 15 carbon atoms, and one —CH$_2$— or two or more unadjacent —CH$_2$— present in the group may be substituted by —O—, —S—, —COO—, —OCO—, or —CO—; A$^1$ and A$^2$ each independently represent a group selected from the group consisting of (a) a 1,4-cyclohexylene group (one —$CH_2$— or two or more unadjacent —$CH_2$— present in the group may be substituted by —O— or —S—), (b) a 1,4-phenylene group (one —CH═ or two or more unadjacent —CH═ present in the group may be substituted by —N═, and a hydrogen atom present in the group may be substituted by a fluorine atom), and (c) a naphthalene-2,6-diene group (a hydrogen atom present in the group may be substituted by a fluorine atom), $Z^1$ and $Z^2$ each independently represent —$CH_2O$—, —$OCH_2$—, —$CF_2O$—, —$OCF_2$—, —$CH_2CH_2$—, —$CF_2CF_2$—, —CH═CH—, —CF═CF—, —C≡C—, or a single bond;

$Y^1$, $Y^2$, and $Y^3$ each independently represent a hydrogen atom, a fluorine atom, or a chlorine atom;

W represents a fluorine atom, a chlorine atom, a cyano group, —$CF_3$—, —$OCH_2F$, —$OCHF_2$, or —$OCF_3$;

m and n each independently represent 0, 1, or 2, m+n is 0, 1, or 2, and when there is a plurality of each or any of $A^1$, $A^2$, $Z^1$, and $Z^2$, each or any of $A^1$, $A^2$, $Z^1$ and $Z^2$ may be the same or different), and also provides a liquid crystal composition containing the compound and a liquid crystal display device using the liquid crystal composition.

Advantageous Effects of Invention

A novel liquid crystal compound provided by the present invention and represented by general formula (1) can be industrially easily produced, and the resultant compound represented by general formula (1) has relatively large $\Delta\in$, relatively high $T_{\to i}$, low viscosity, and high solubility in a liquid crystal composition.

Therefore, by using the compound represented by general formula (1) as a component of a liquid crystal composition, a liquid crystal composition exhibiting low viscosity and a liquid crystal phase over a wide temperature range can be produced. Therefore, the compound is very useful as a component of a liquid crystal composition for a liquid crystal display device required to have fast response.

BRIEF DESCRIPTION OF DRAWINGS

Description of Embodiments

In order to decrease viscosity, R in the general formula (1) is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms. Also, the group is preferably linear.

In order to decrease viscosity, $A^1$ and $A^2$ are each independently preferably a trans-1,4-cyclohexylene group or an unsubstituted 1,4-phenylene group, and preferably a trans-1,4-cyclohexylene group; in order to increase $\Delta\in$,

[Chem. 2]

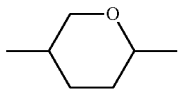 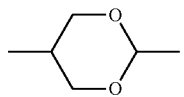

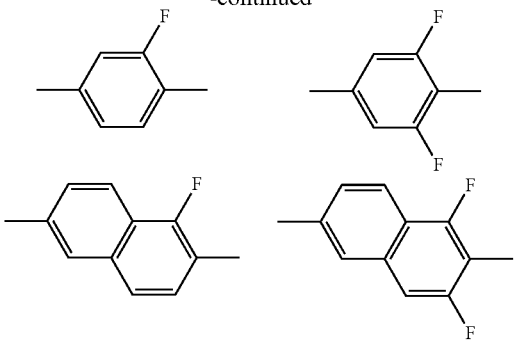

are preferred, and

[Chem. 3]

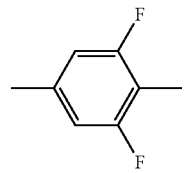

is more preferred; and in order to increase the liquid crystal phase upper limit temperature, a trans-1,4-cyclohexylene group or an unsubstituted 1,4-phenylene group is preferred.

In order to decrease viscosity, $Z^1$ and $Z^2$ are each independently preferably —$CH_2O$—, —$OCH_2$—, —$CF_2O$—, —$OCF_2$—, —CF═CF—, —C≡C—, or a single bond, and more preferably —$CF_2O$—, —$OCF_2$—, —$CH_2CH_2$—, or a single bond.

$Y^1$ represents a hydrogen atom, a fluorine atom, or a chlorine atom, and in order to decrease viscosity, $Y^1$ is preferably a hydrogen atom or a fluorine atom, and in order to increase $\Delta\in$, $Y^1$ is preferably a fluorine atom.

In order to decrease viscosity, $Y^2$ and $Y^3$ are each independently preferably a hydrogen atom, and in order to increase $\Delta\in$, at least one of $Y^2$ and $Y^3$ is preferably a fluorine atom, and both of $Y^2$ and $Y^3$ are more preferably fluorine atoms.

In order to increase $\Delta\in$, W is preferably a fluorine atom, a cyano group, —$CF_2$, or —$OCF_3$, and in order to decrease viscosity, W is preferably a fluorine atom.

In order to balance $\Delta\in$, $T_{\to i}$, and viscosity, preferably, $Y^2$, $Y^3$, and W are fluorine atoms, or W is a —$OCF_3$ group and $Y^2$ and $Y^3$ are both hydrogen atoms. When $\Delta\in$ is regarded as important, $Y^2$, $Y^3$, and W are preferably fluorine atoms, while when $T_{\to i}$ and viscosity are regarded as important, preferably, W is a —$OCF_3$ group and $Y^2$ and $Y^3$ are both hydrogen atoms.

When η is regarded as important, m is preferably 0 or 1, while when $T_{\to i}$ is regarded as important, m is preferably 1 or 2. When η is regarded as important, n is preferably 0 or 1, while when $T_{\to i}$ is regarded as important, n is preferably 1 or 2. When η is regarded as important, m+n is preferably 0 or 1, when $T_{\to i}$ is regarded as important, m+n is preferably 1 or 2, and when balance between η and $T_{\to i}$ is regarded as important, m+n is preferably 1 or 2, and particularly preferably, m is 1 or 2, and n is 0. In order to suppress precipitation of a liquid crystal composition, preferably, m is 0 and n is 1 or 2.

When m represents 2, there are two each of $A^1$ and $Z^1$. In this case, two $A^1$ may be the same or different, and two $Z^1$ may be the same or different.

When n represents 2, there are two each of $A^2$ and $Z^2$. In this case, two $A^2$ may be the same or different, and two $Z^2$ may be the same or different.

A compound represented by the general formula (1) never has a structure in which heteroatoms are directly bonded to each other.

Although examples of preferred compounds are given below, the present invention is not limited to these examples. The general formula (1) is preferably a compound represented by each of general formula (1-1) to general formula (1-54), general formula (2-1) to general formula (2-18), general formula (3-1) to general formula (3-18), general formula (4-1) to general formula (4-18), general formula (5-1) to general formula (5-18), general formula (6-1) to general formula (6-18), general formula (7-1) to general formula (7-18), general formula (8-1) to general formula (8-18), general formula (9-1) to general formula (9-18), general formula (10-1) to general formula (10-18), general formula (11-1) to general formula (11-18), and general formula (12-1) to general formula (12-18) described below.

[Chem. 4]

(1-1)
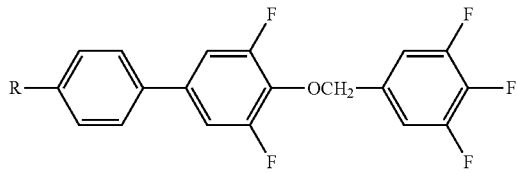

(1-2)
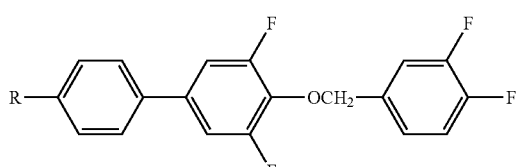

(1-3)
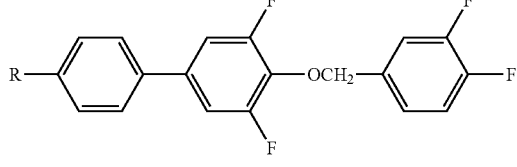

(1-4)
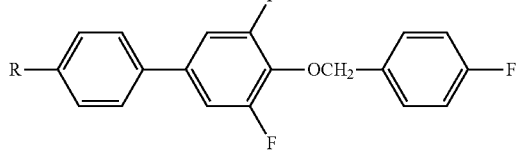

(1-5)
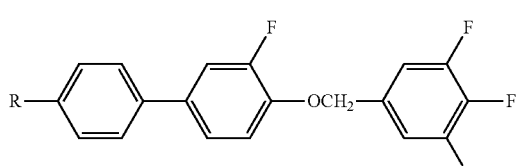

(1-6)
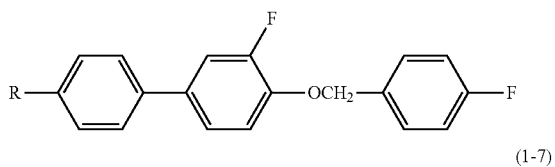

(1-7)
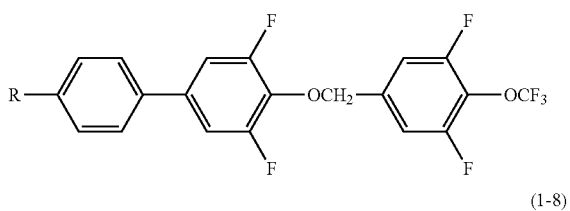

(1-8)
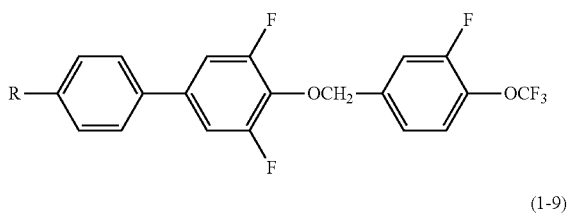

(1-9)
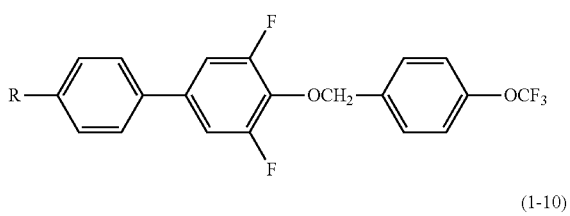

(1-10)
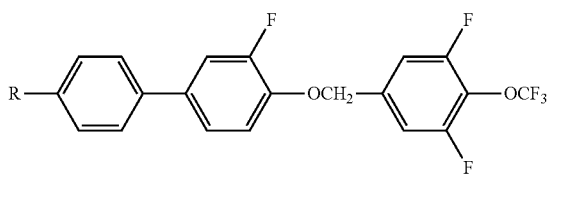

(1-11)
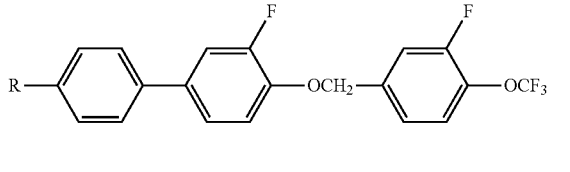

(1-12)
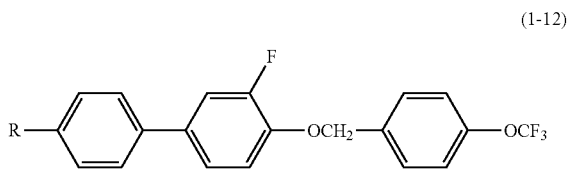

(1-13)
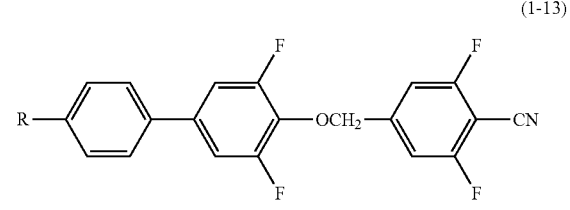

(1-14)
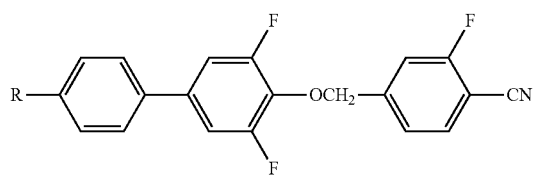
(1-15)
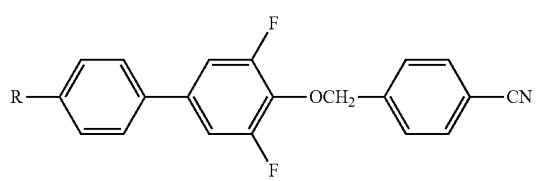
(1-16)
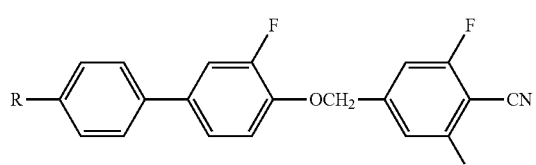
(1-17)
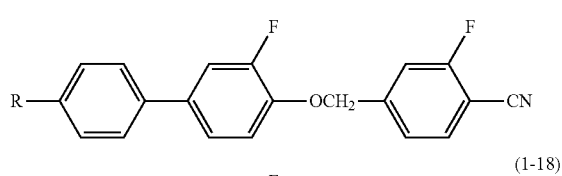
[Chem. 5]
(1-19)
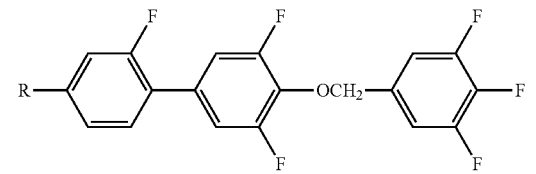
(1-20)
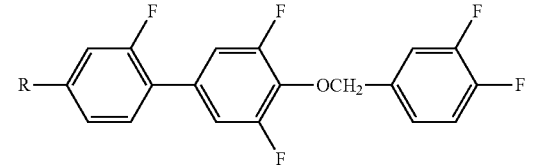
(1-21)
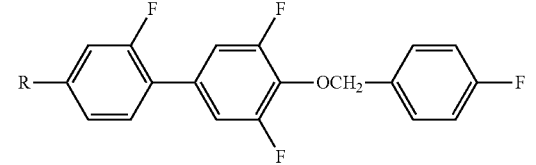
(1-22)
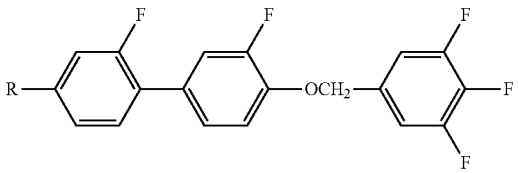
(1-23)
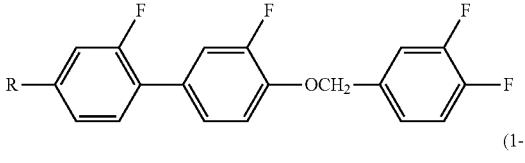
(1-24)
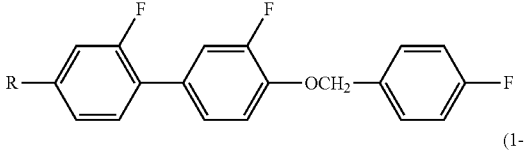
(1-25)
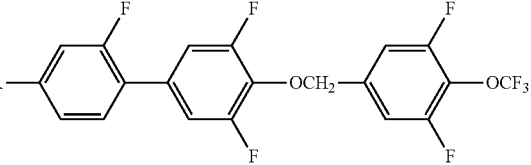
(1-26)
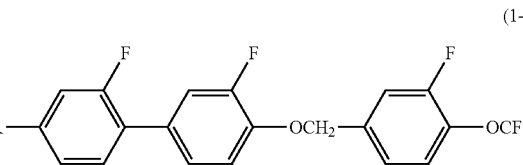
(1-27)
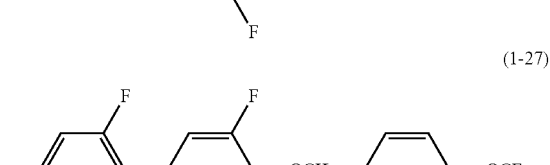
(1-28)
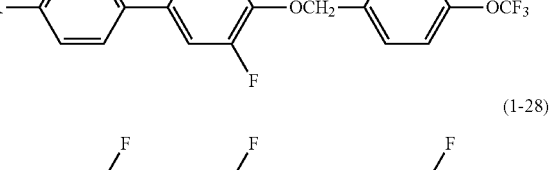
(1-29)
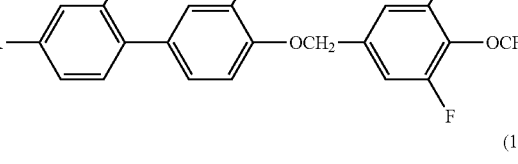
(1-30)
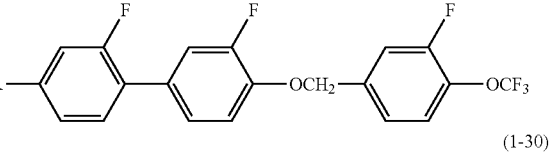

(1-31) 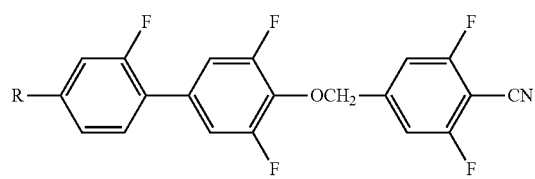
(1-32) 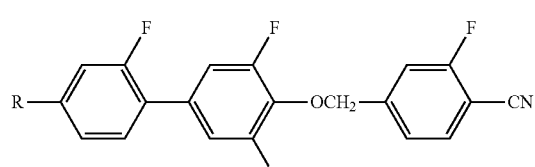
(1-33) 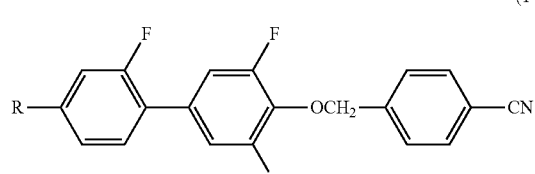
(1-34) 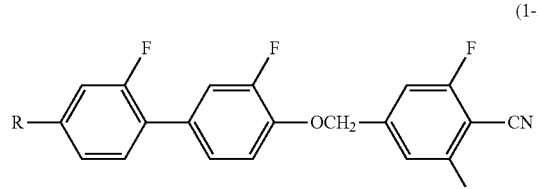
(1-35) 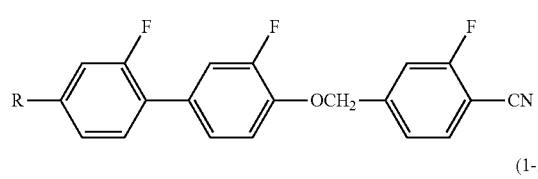
(1-36) 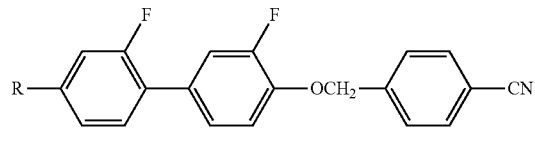
[Chem. 6]
(1-37) 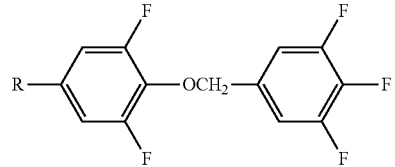
(1-38) 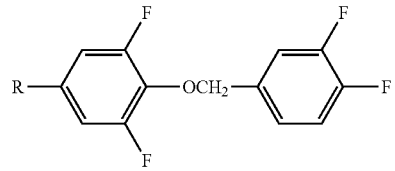
(1-39) 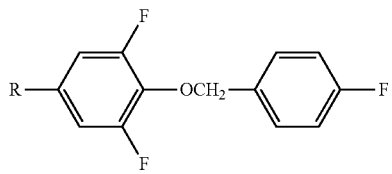
(1-40) 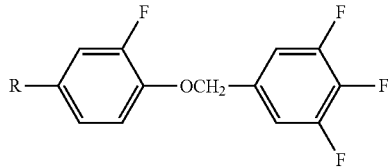
(1-41) 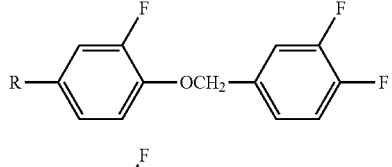
(1-42) 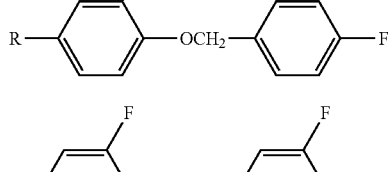
(1-43) 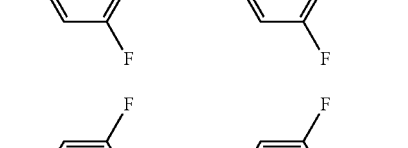
(1-44) 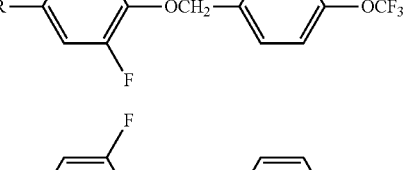
(1-45) 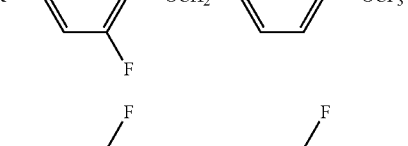
(1-46) 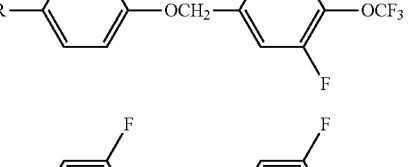
(1-47) 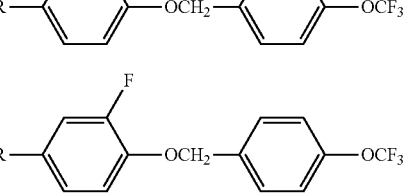
(1-48)

-continued
(1-49)
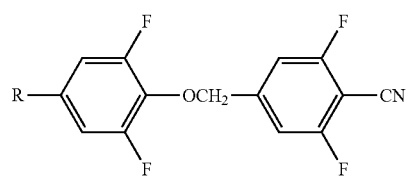
(1-50)
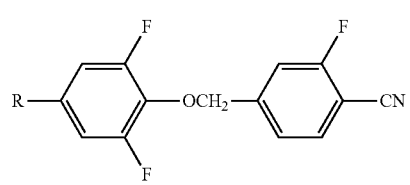
(1-51)
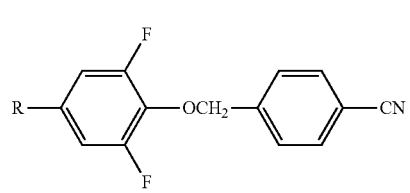
(1-52)
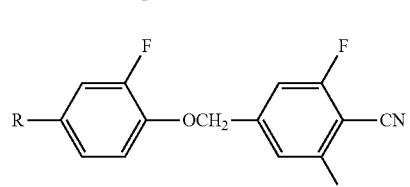
(1-53)
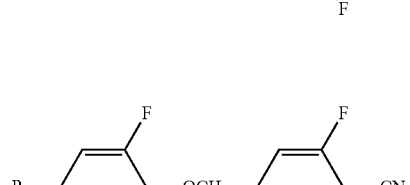
(1-54)
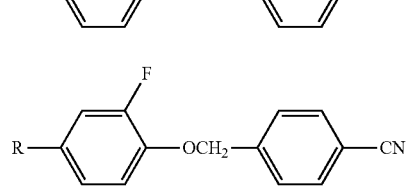
[Chem. 7]
(2-1)
(2-2)
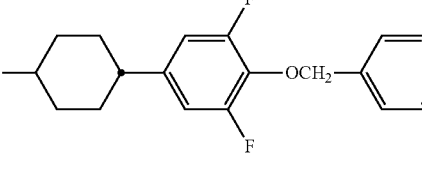
-continued
(2-3)
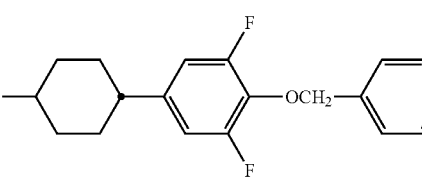
(2-4)
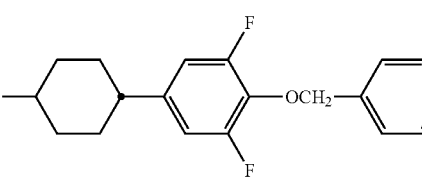
(2-5)
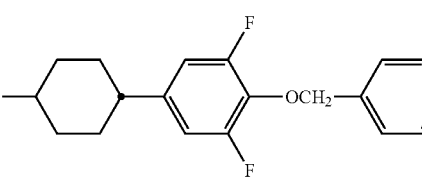
(2-6)
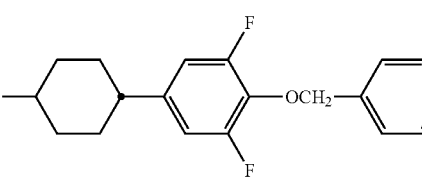
(2-7)
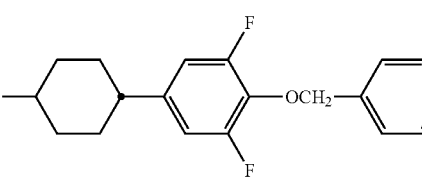
(2-8)
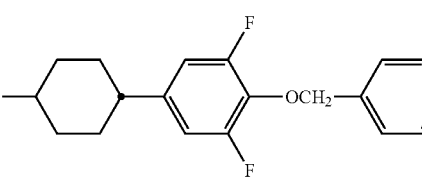
(2-9)
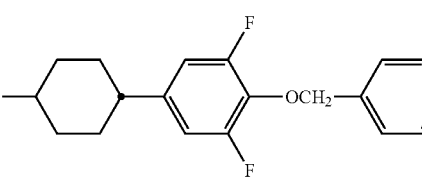
(2-10)
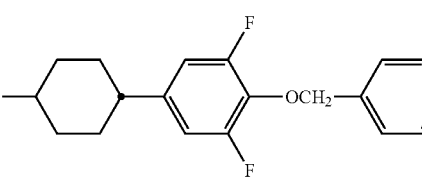

(2-11) 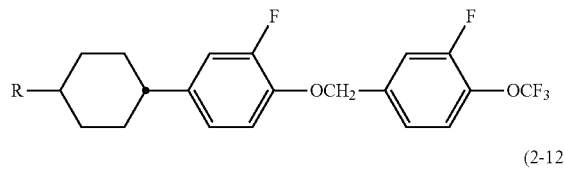
(2-12) 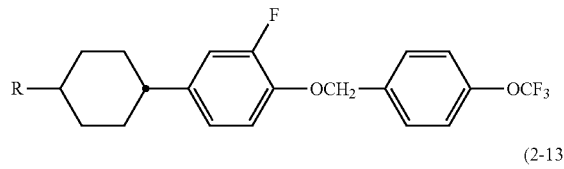
(2-13) 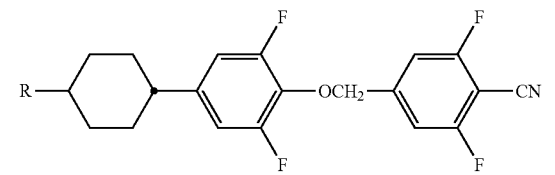
(2-14) 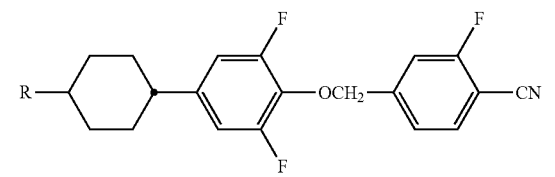
(2-15) 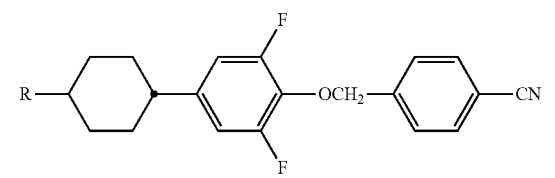
(2-16) 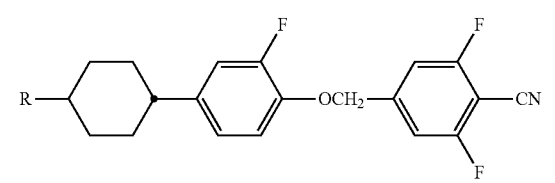
(2-17) 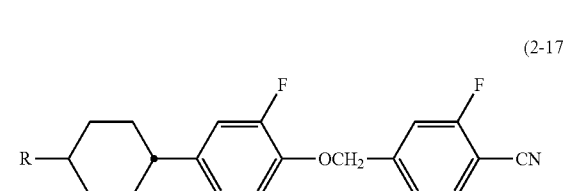
(2-18) 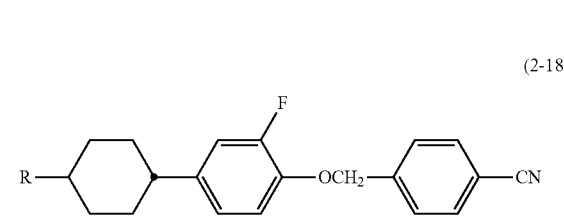
[Chem. 8]
(3-1) 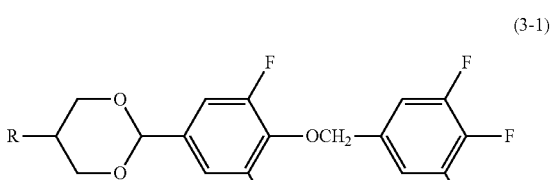
(3-2) 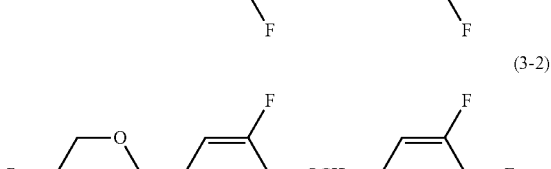
(3-3) 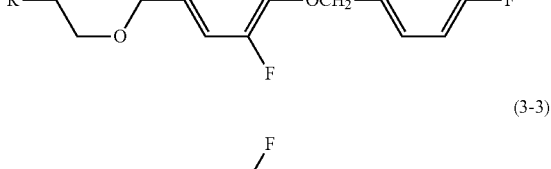
(3-4) 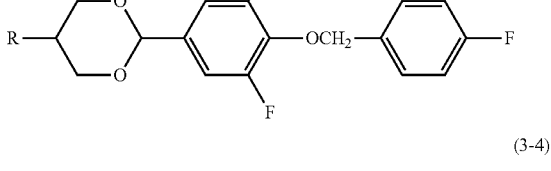
(3-5) 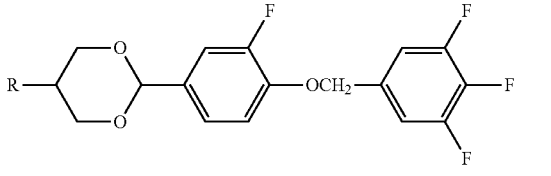
(3-6) 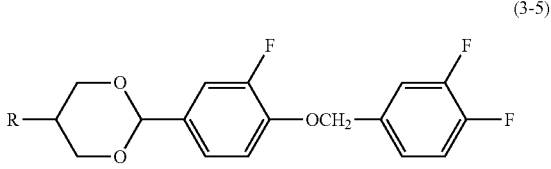
(3-7) 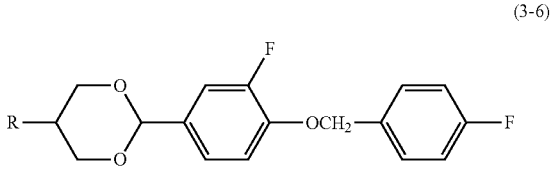
(3-8) 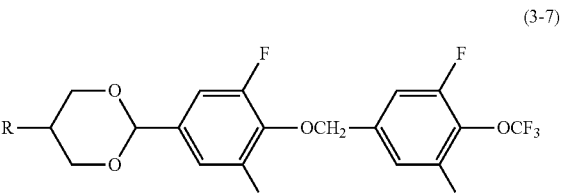

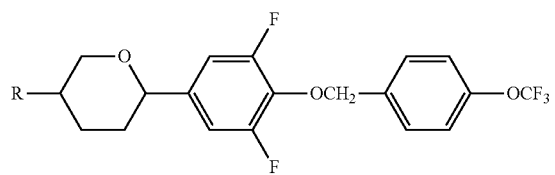
(3-9)
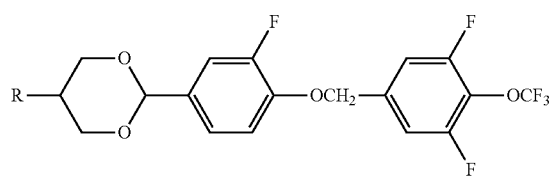
(3-10)
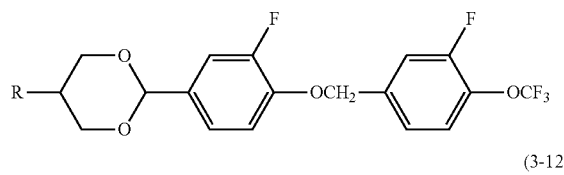
(3-11)
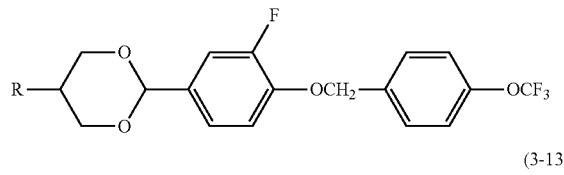
(3-12)
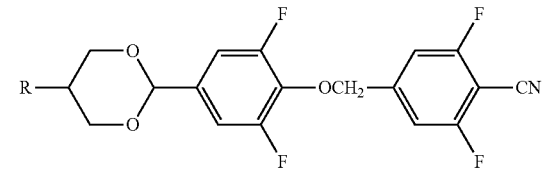
(3-13)
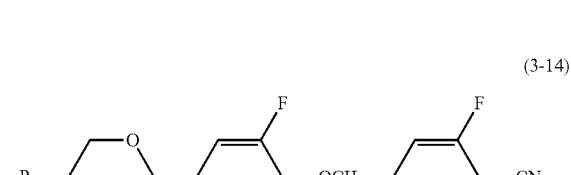
(3-14)
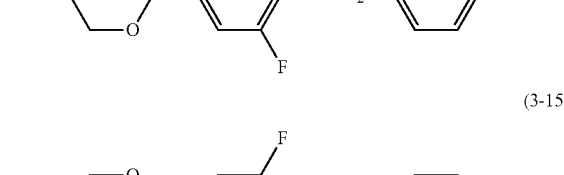
(3-15)
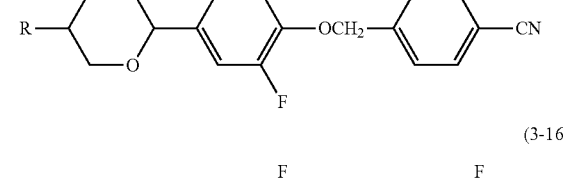
(3-16)
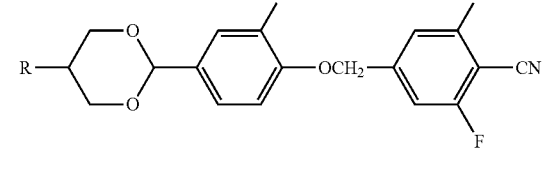
(3-17)
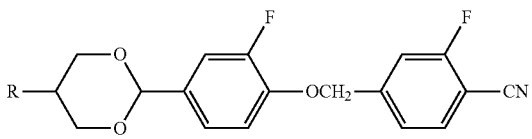
(3-17)
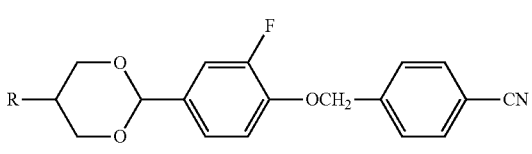
(3-18)
[Chem. 9]
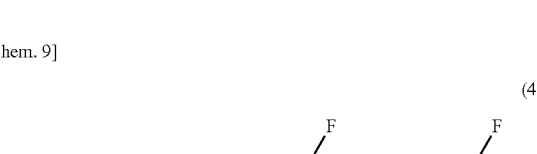
(4-1)
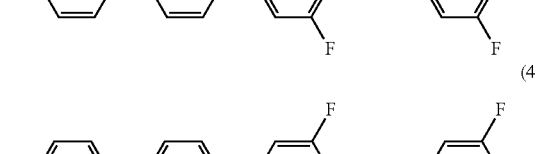
(4-2)
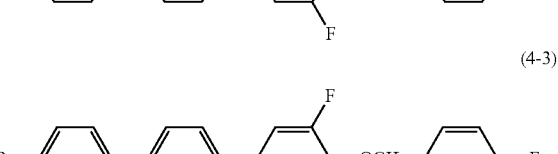
(4-3)
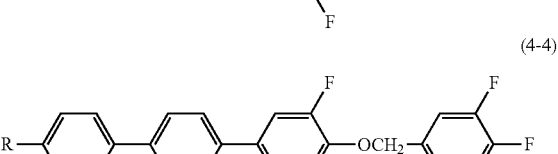
(4-4)
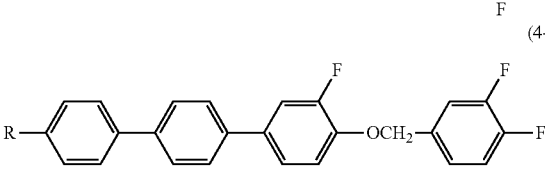
(4-5)
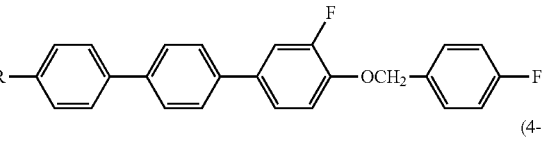
(4-6)
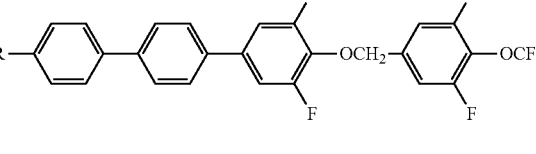
(4-7)

(4-8)
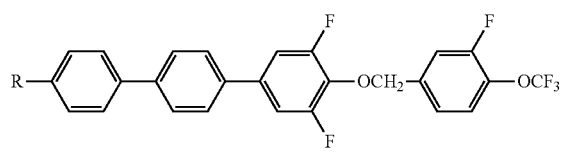
(4-9)
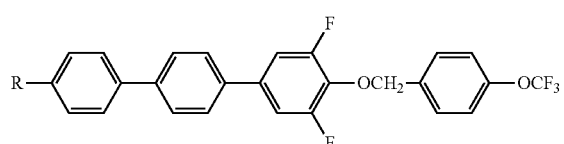
(4-10)
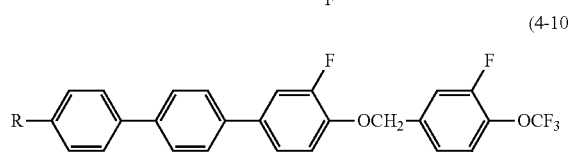
(4-11)
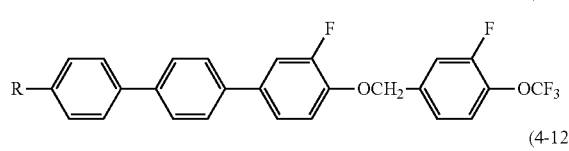
(4-12)
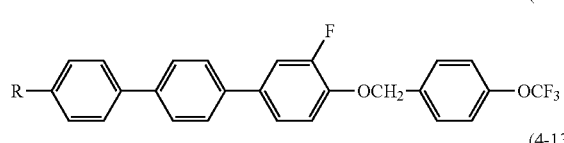
(4-13)
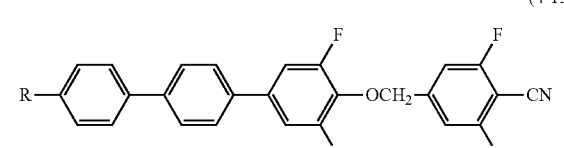
(4-14)
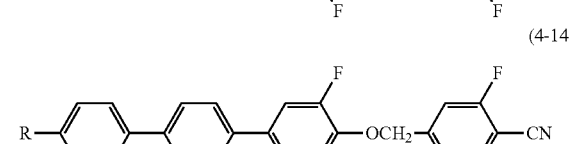
(4-15)
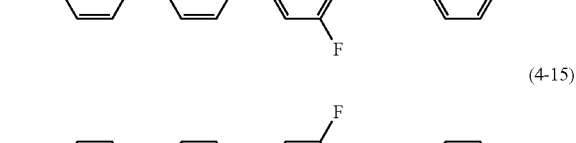
(4-16)
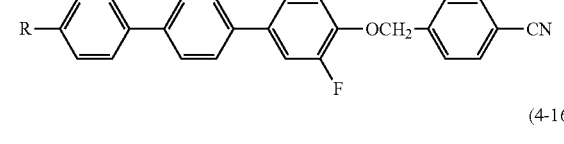
(4-17)
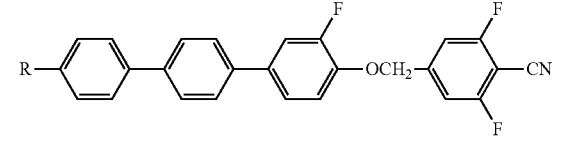
(4-18)
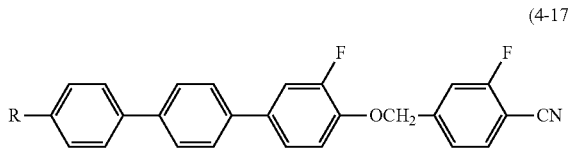
[Chem. 10]
(5-1)
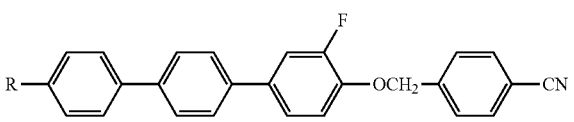
(5-2)
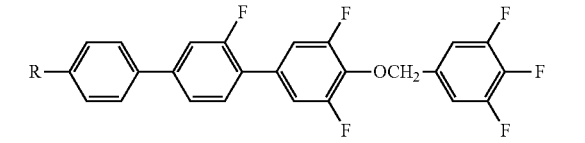
(5-3)
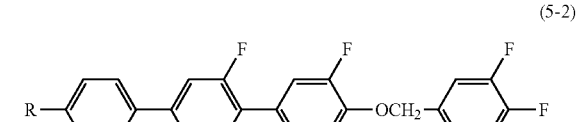
(5-4)
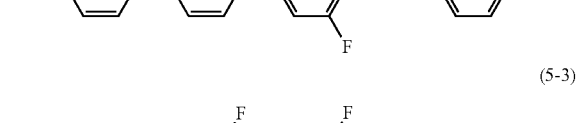
(5-5)
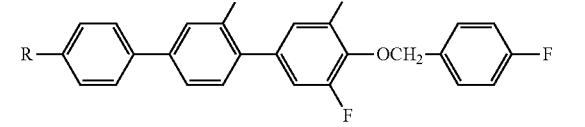
(5-6)
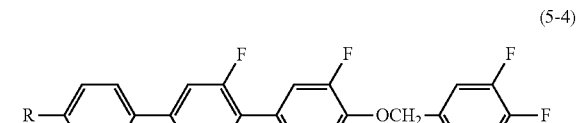
(5-7)
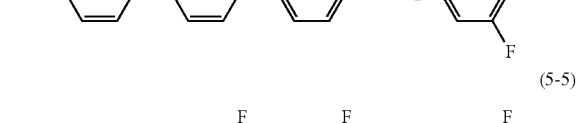
(5-8)
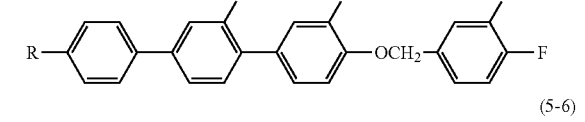

-continued
(5-9) 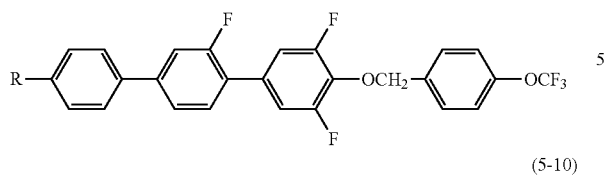
(5-10) 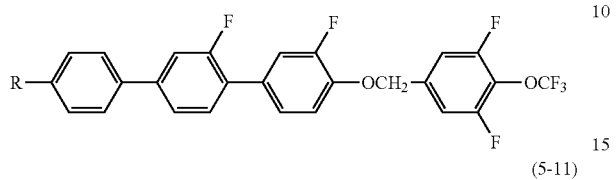
(5-11) 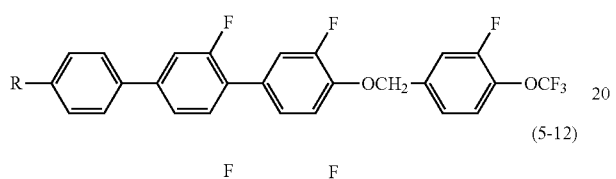
(5-12) 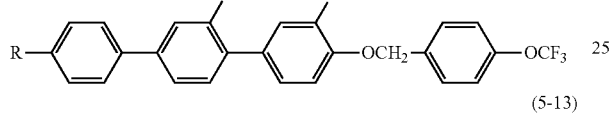
(5-13) 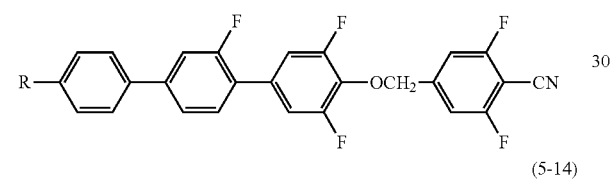
(5-14) 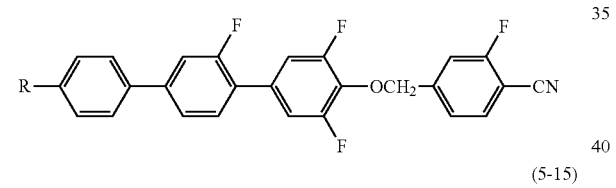
(5-15) 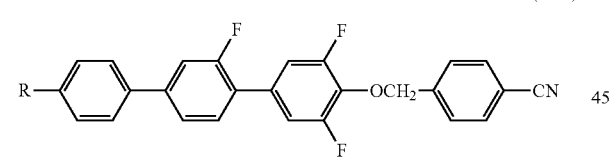
(5-16) 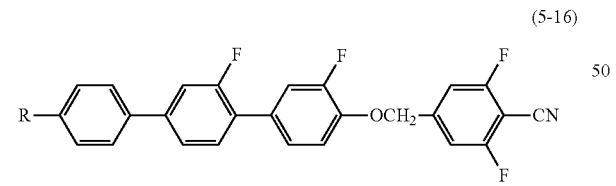
(5-17) 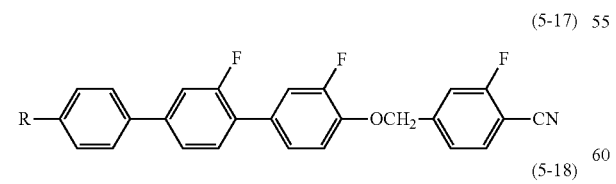
(5-18) 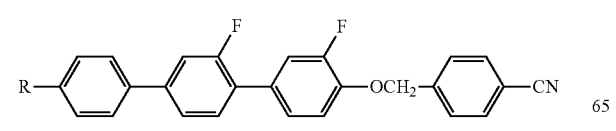
[Chem. 11]
(6-1) 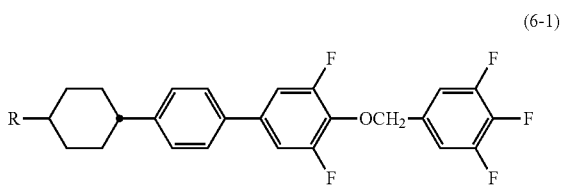
(6-2) 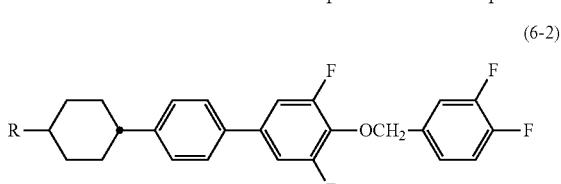
(6-3) 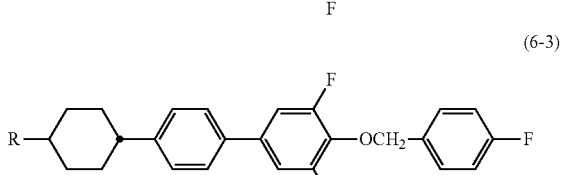
(6-4) 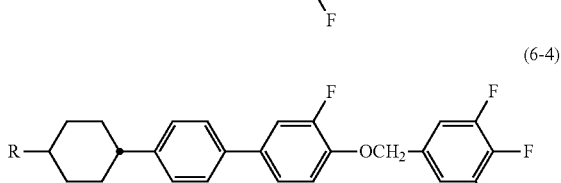
(6-5) 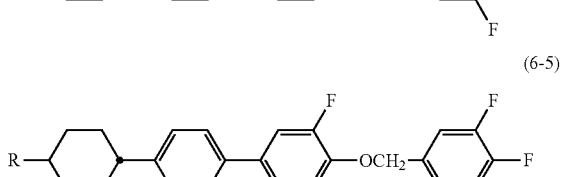
(6-6) 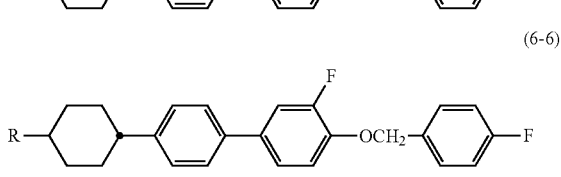
(6-7) 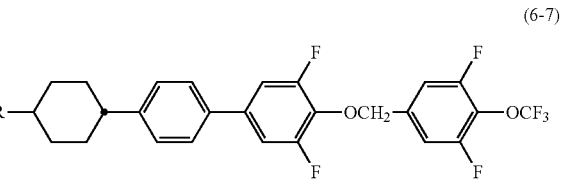
(6-8) 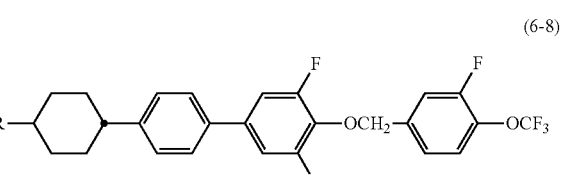
(6-9) 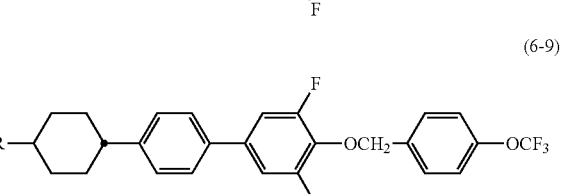

(6-10) 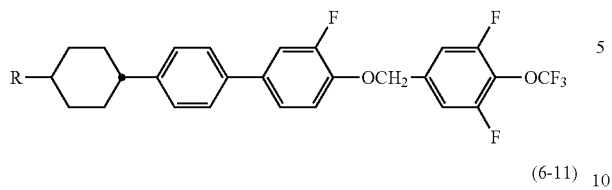
(6-11) 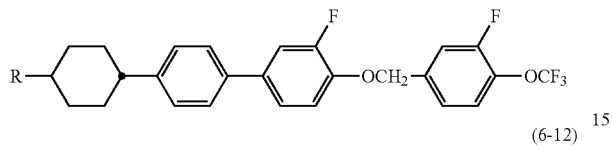
(6-12) 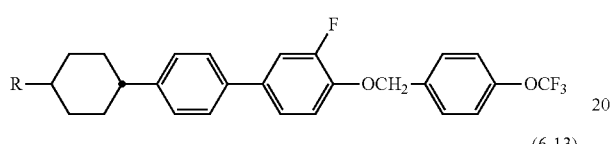
(6-13) 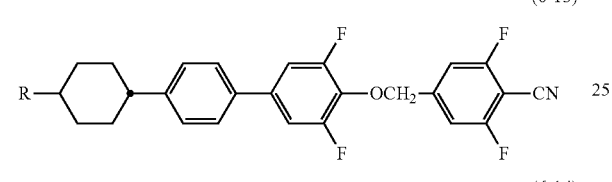
(6-14) 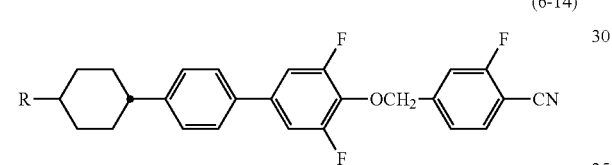
(6-15) 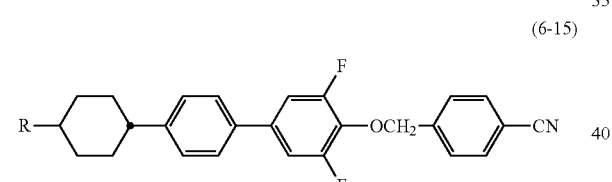
(6-16) 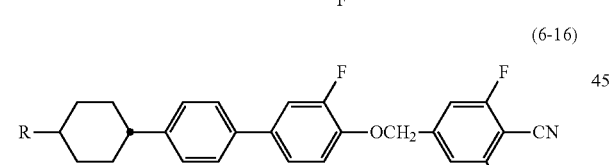
(6-17) 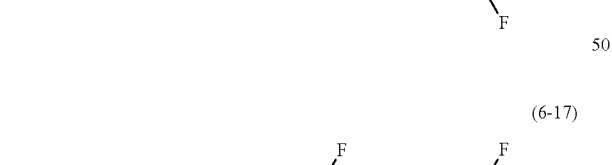
(6-18) 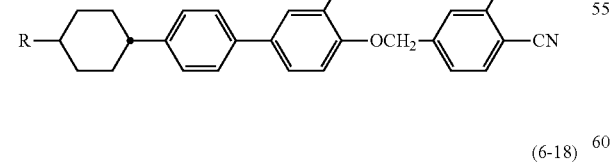
[Chem. 12]
(7-1) 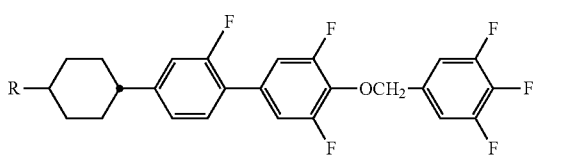
(7-2) 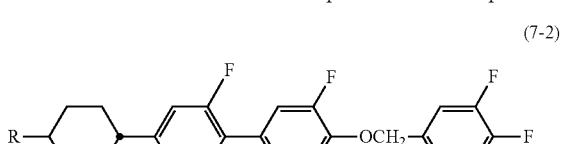
(7-3) 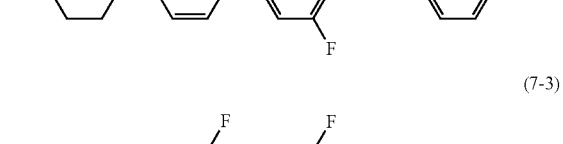
(7-4) 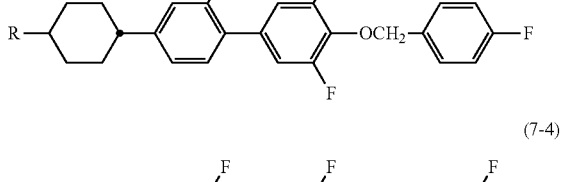
(7-5) 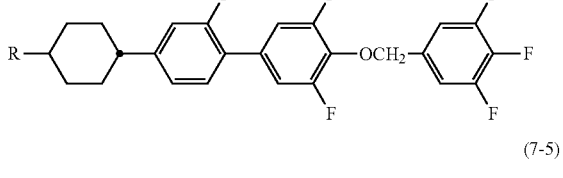
(7-6) 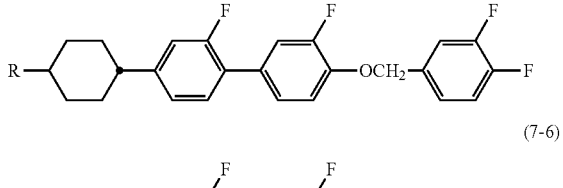
(7-7) 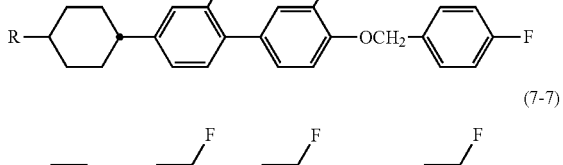
(7-8) 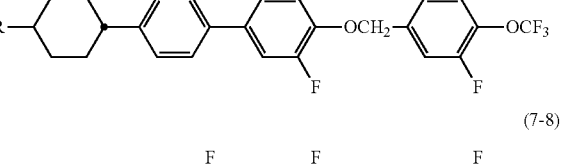
(7-9) 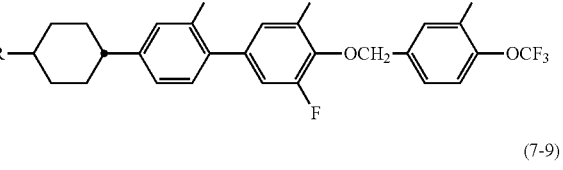

[Chem. 13]

(8-8)
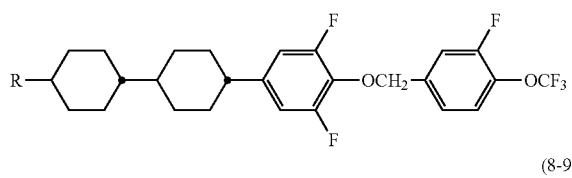
(8-9)
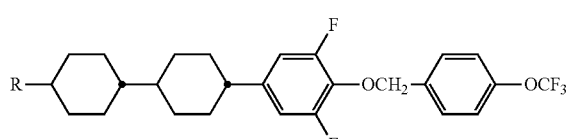
(8-10)
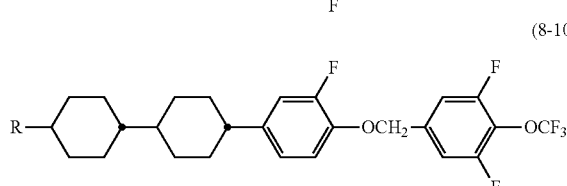
(8-11)
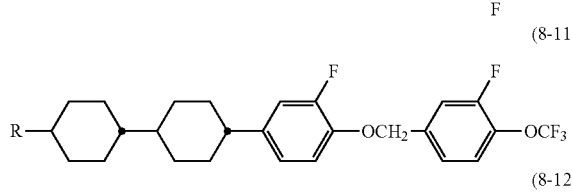
(8-12)
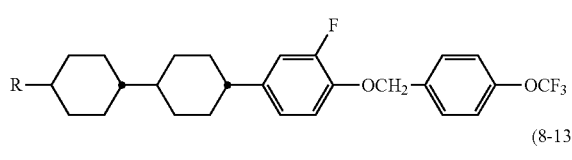
(8-13)
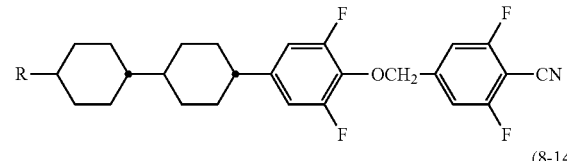
(8-14)
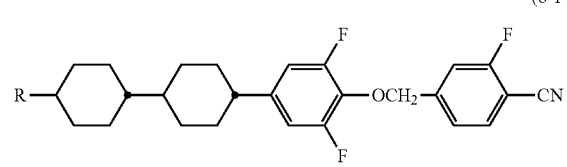
(8-15)
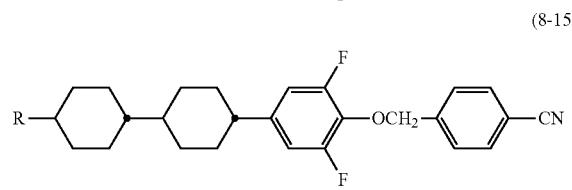
(8-16)
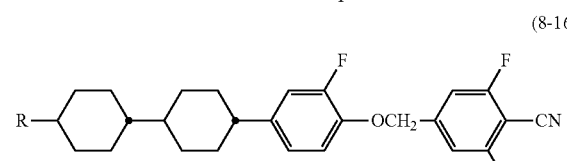
(8-17)
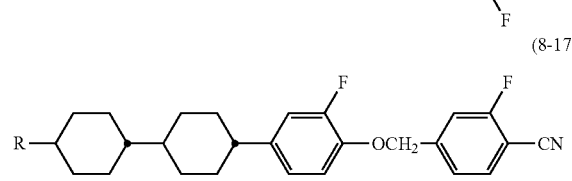
(8-18)
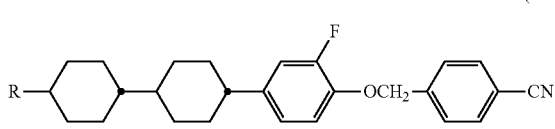
[Chem. 14]
(9-1)
(9-2)
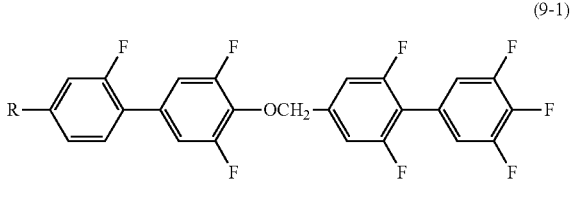
(9-3)
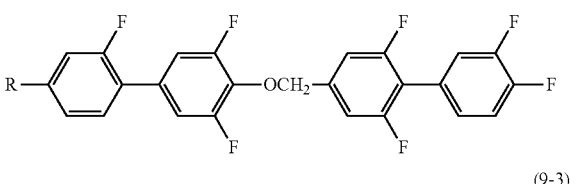
(9-4)
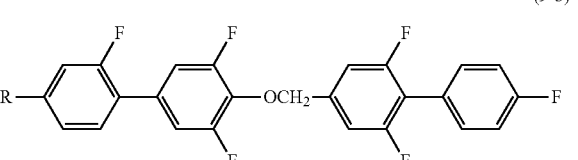
(9-5)
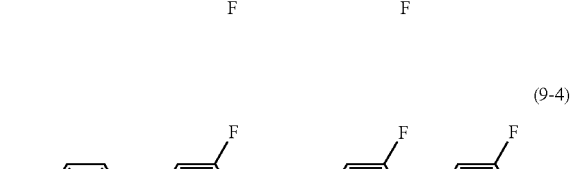
(9-6)
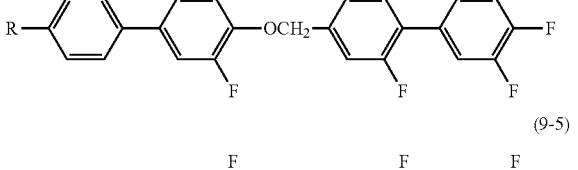
(9-7)
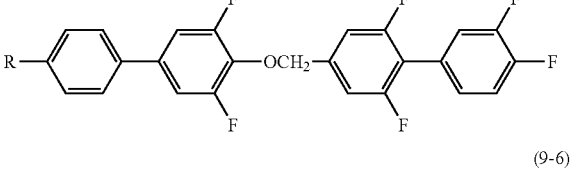

(9-8) 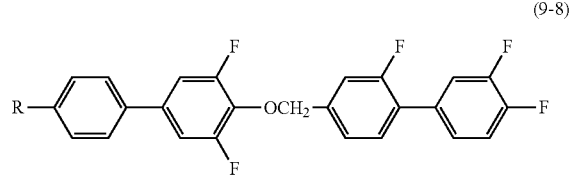
(9-9) 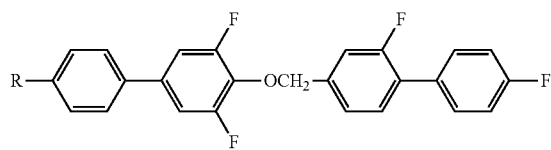
(9-10) 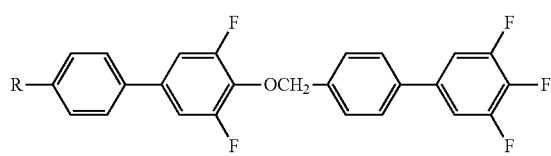
(9-11) 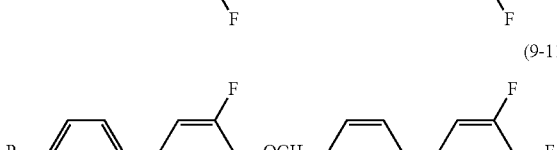
(9-12) 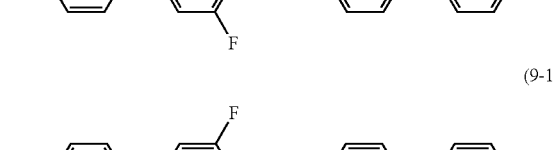
(9-13) 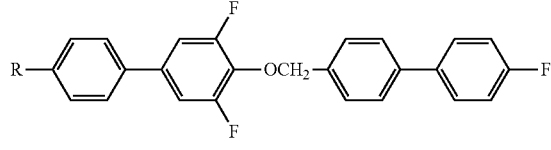
(9-14) 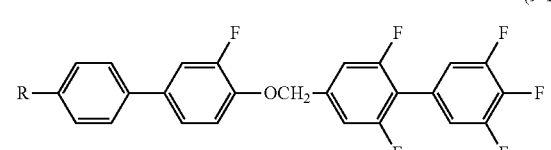
(9-15) 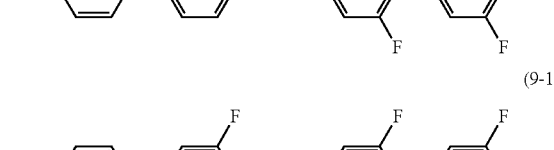
(9-16) 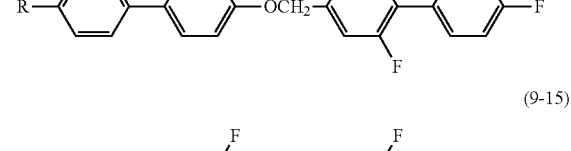
(9-17) 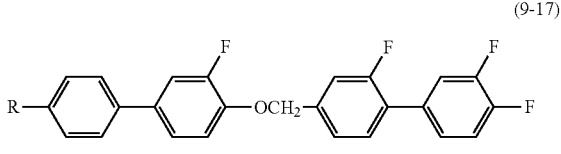
(9-18) 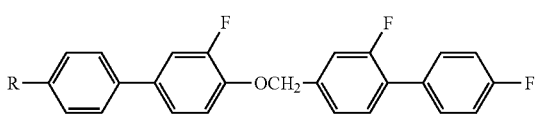
[Chem. 15]
(10-1) 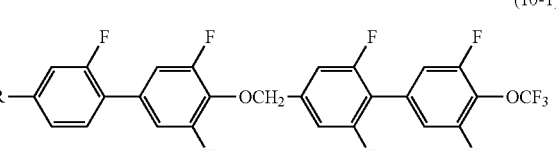
(10-2) 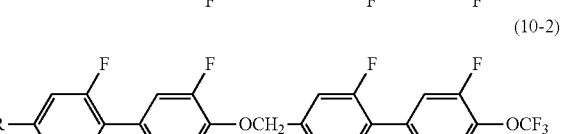
(10-3) 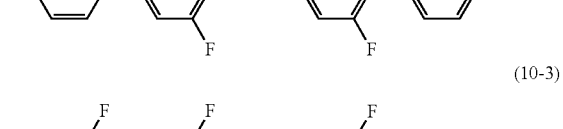
(10-4) 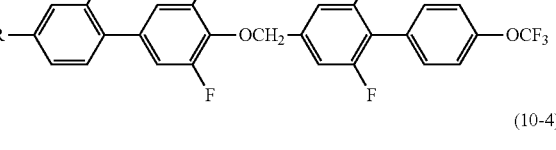
(10-5) 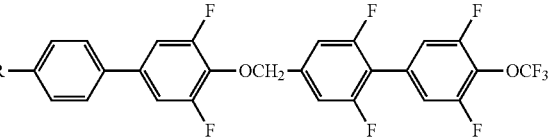
(10-6) 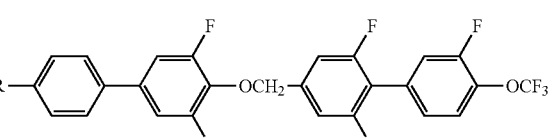
(10-7) 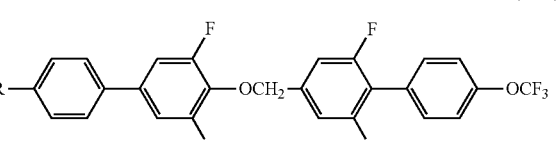

-continued
(10-8) 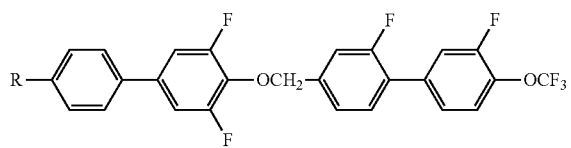
(10-9) 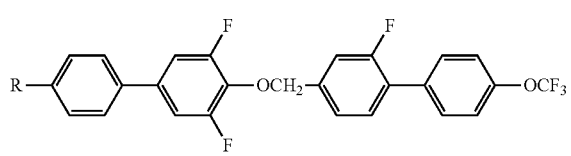
(10-10) 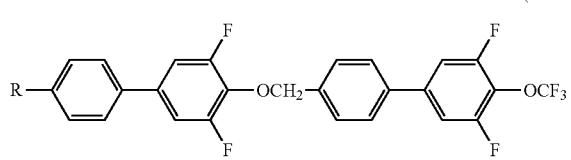
(10-11) 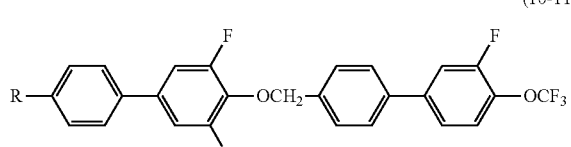
(10-12) 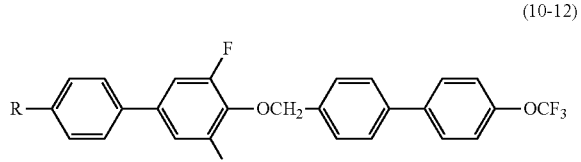
(10-13) 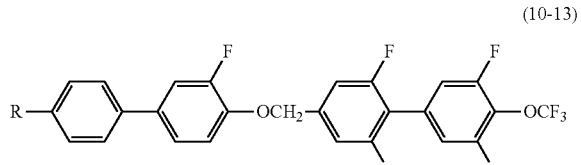
(10-14) 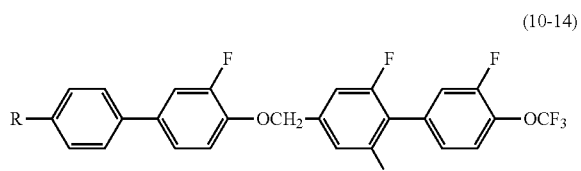
(10-15) 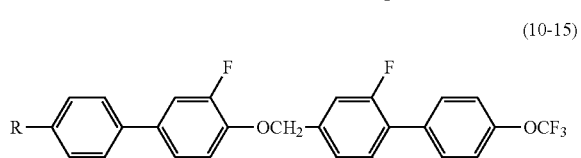
(10-16) 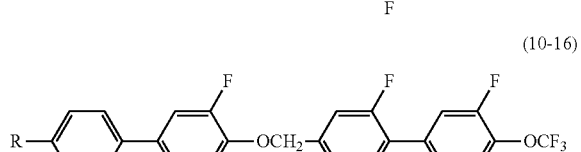
-continued
(10-17) 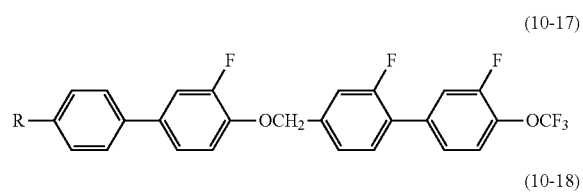
(10-18) 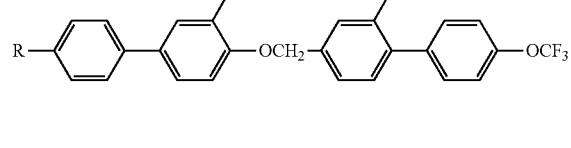
[Chem. 16]
(11-1) 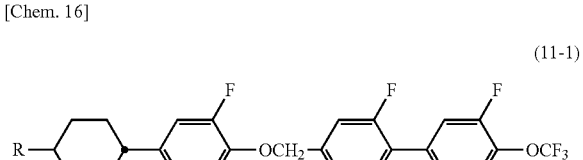
(11-2) 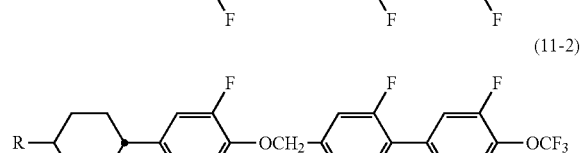
(11-3) 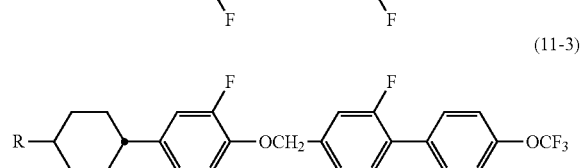
(11-4) 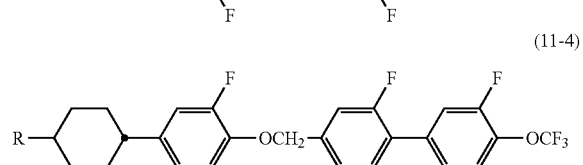
(11-5) 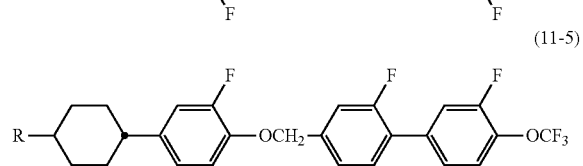
(11-6) 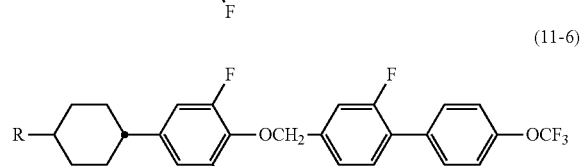
(11-7) 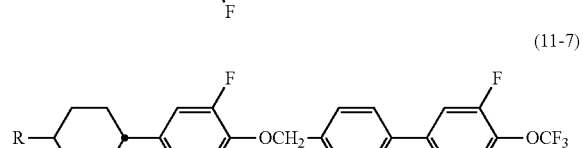

(11-8)
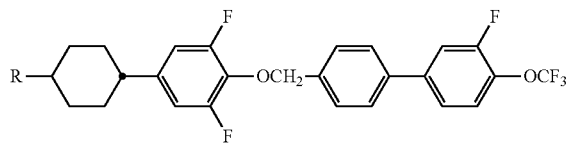
(11-9)
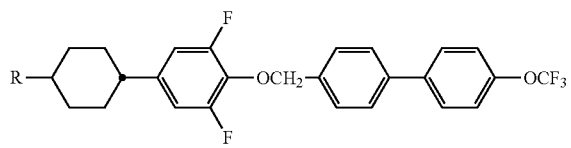
(11-10)
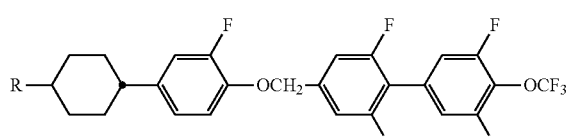
(11-11)
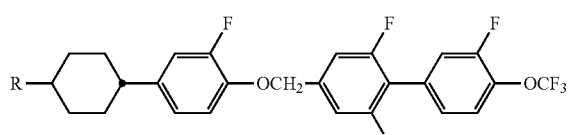
(11-12)
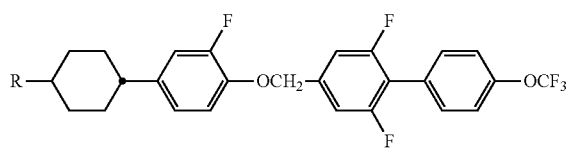
(11-13)
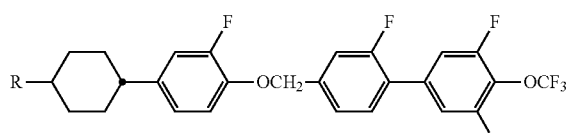
(11-14)
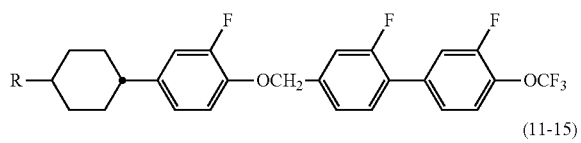
(11-15)
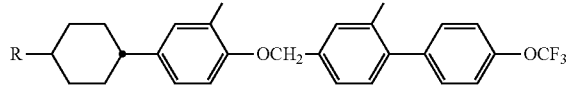
(11-16)
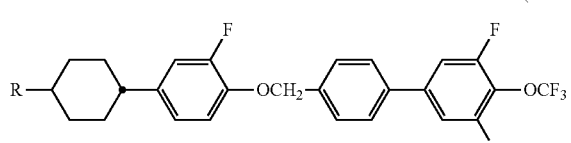
(11-17)
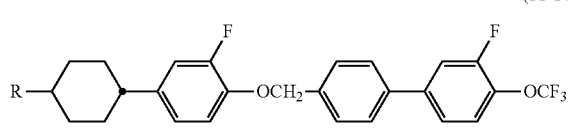
(11-18)
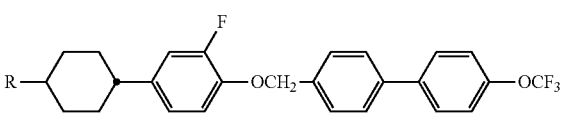
[Chem. 17]
(12-1)
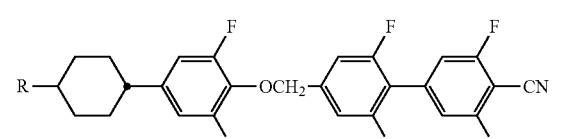
(12-2)
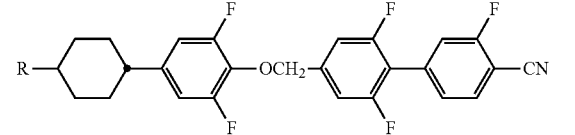
(12-3)
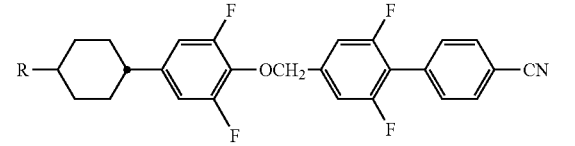
(12-4)
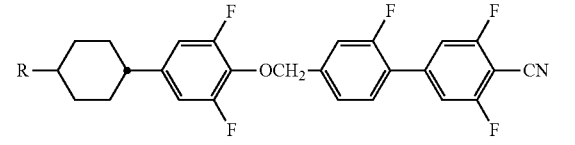
(12-5)
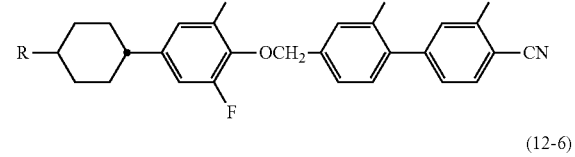
(12-6)
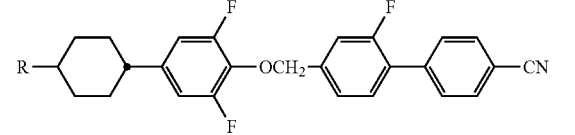
(12-7)
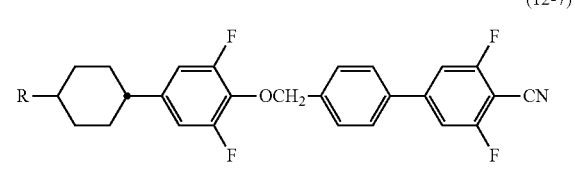

(12-8)
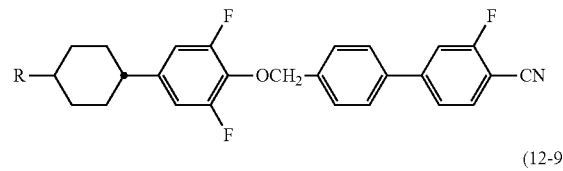
(12-9)
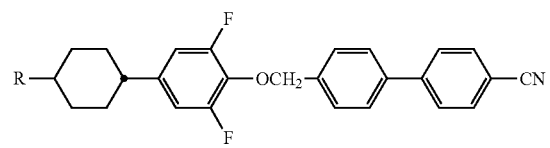
(12-10)
(12-11)
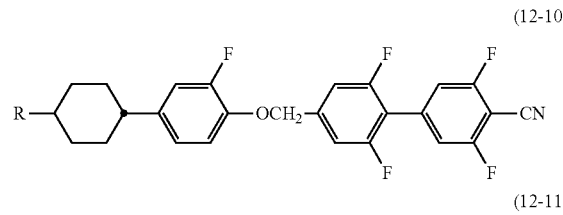
(12-12)
(12-13)
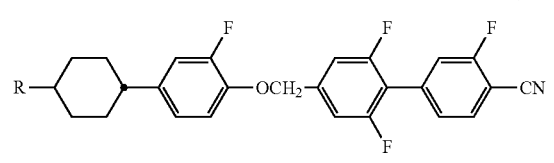
(12-14)
(12-15)
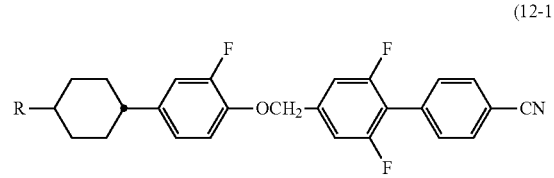
(12-16)
(12-17)
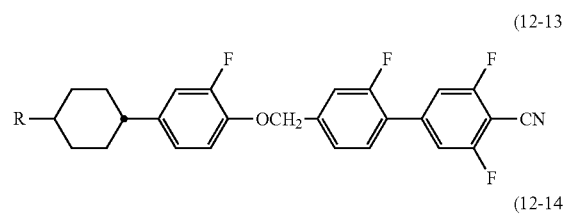
(12-18)
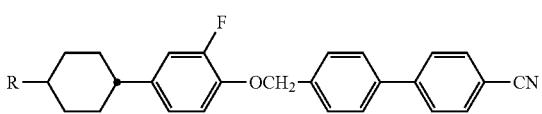
[Chem. 18]
(13-1)
(13-2)
(13-3)
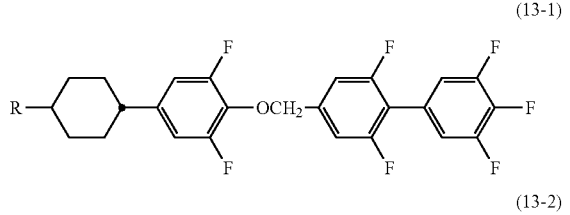
(13-4)
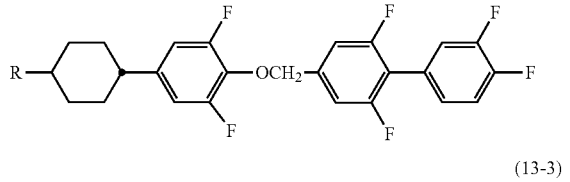
(13-5)
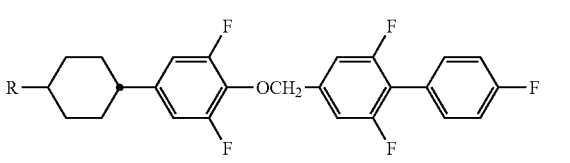
(13-6)
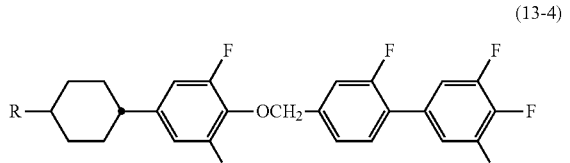
(13-7)
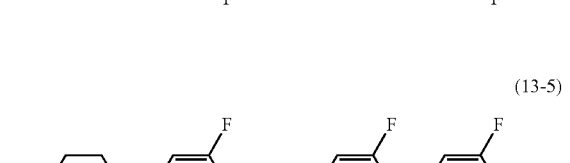

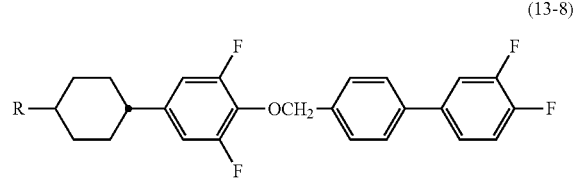
(13-8)
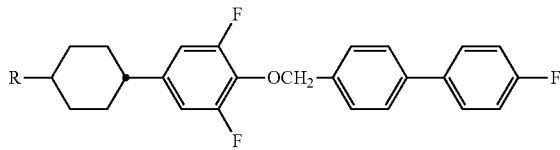
(13-9)
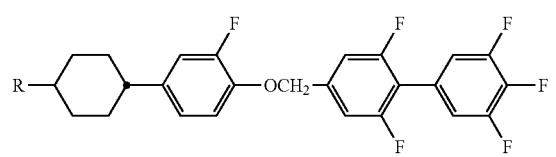
(13-10)
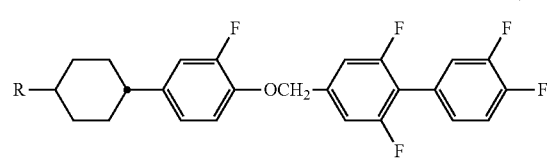
(13-11)
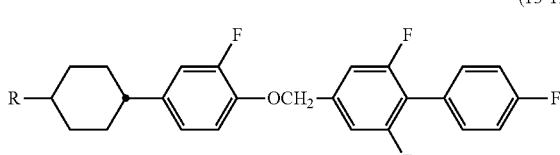
(13-12)
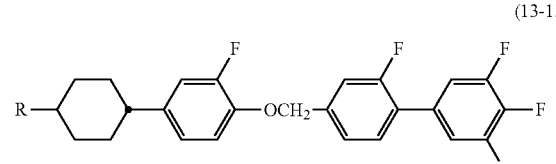
(13-13)
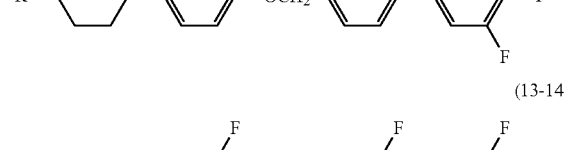
(13-14)
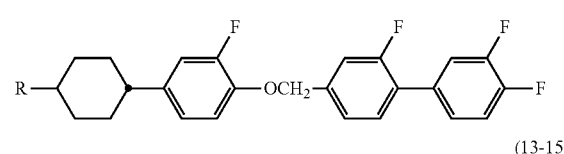
(13-15)
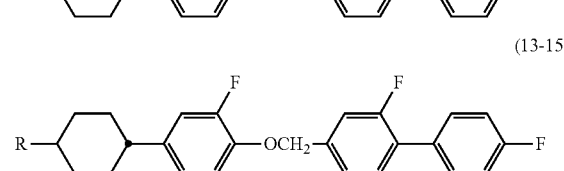
(13-16)
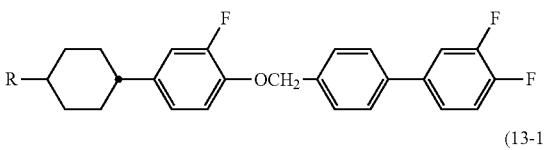
(13-17)
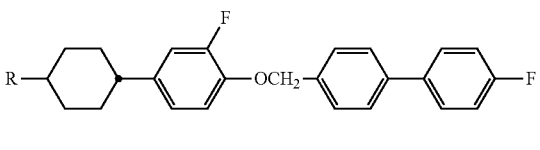
(13-18)
[Chem. 19]
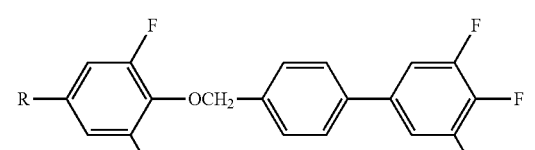
(14-1)
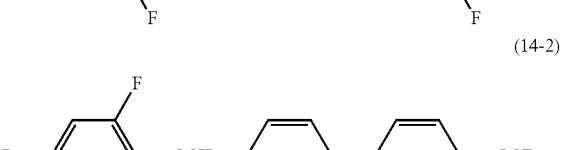
(14-2)
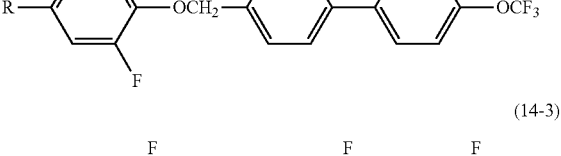
(14-3)
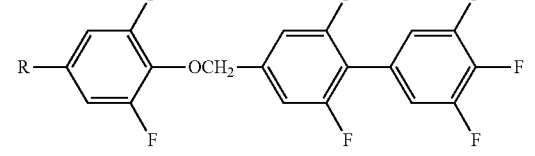
(14-4)
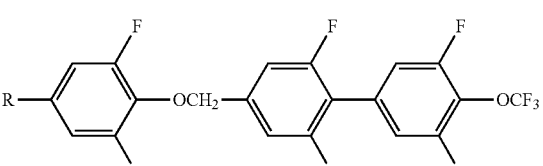
(14-5)
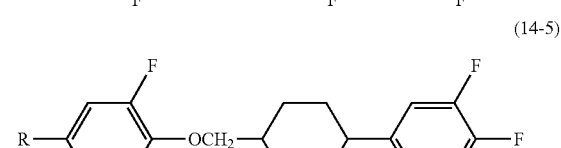
(14-6)
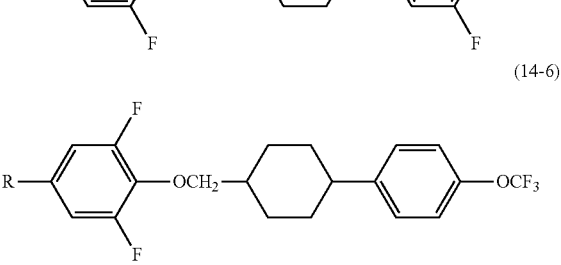

(15-1) 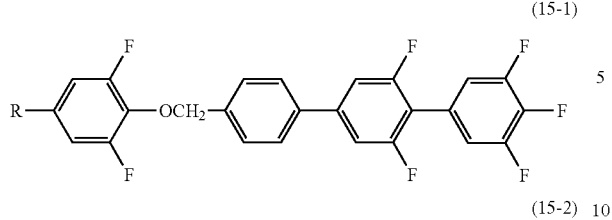
(15-2) 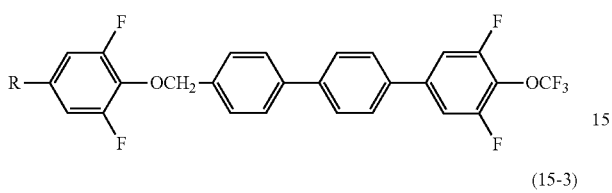
(15-3) 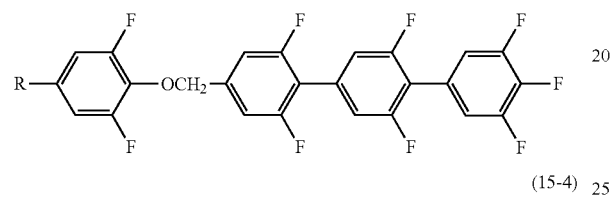
(15-4) 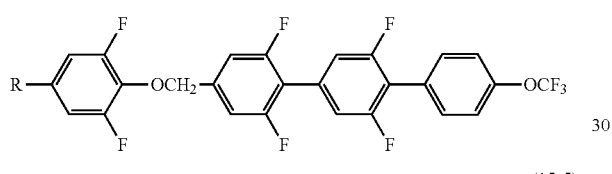
(15-5) 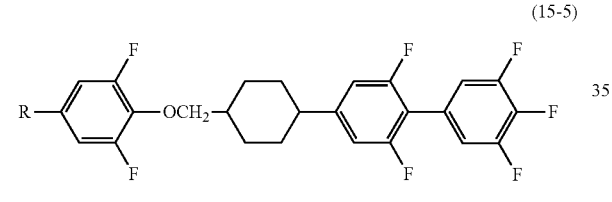
(15-6) 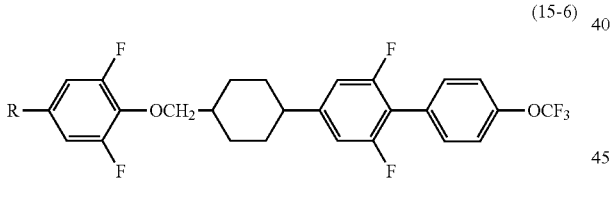
(15-7) 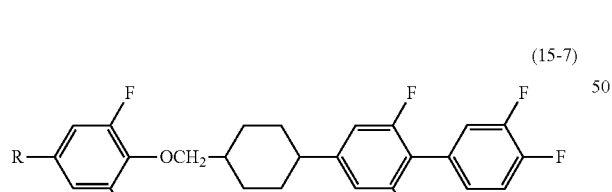
(15-8) 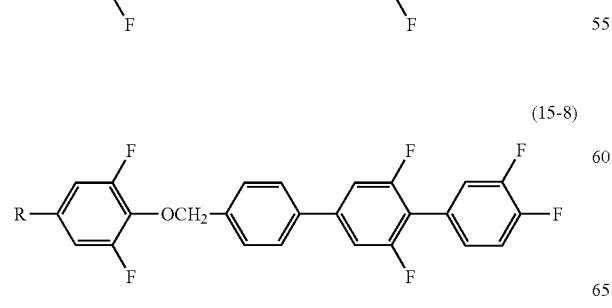
[Chem. 20]
(16-1) 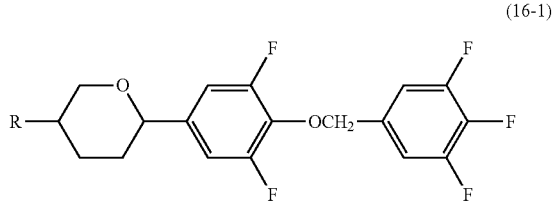
(16-2) 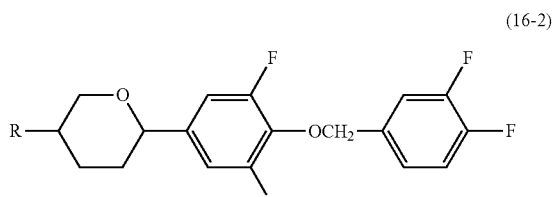
(16-3) 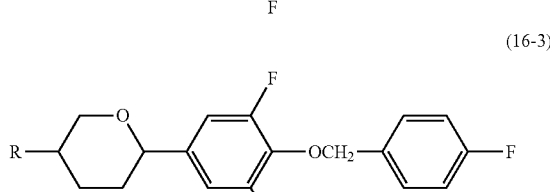
(16-4) 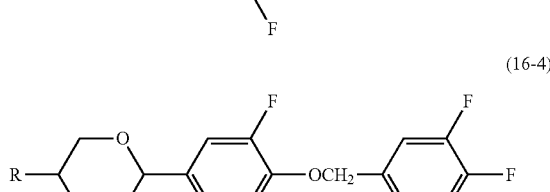
(16-5) 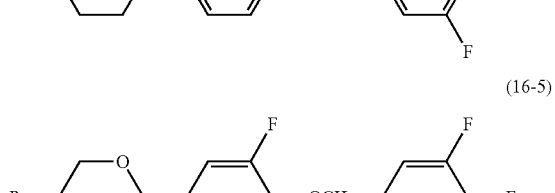
(16-6) 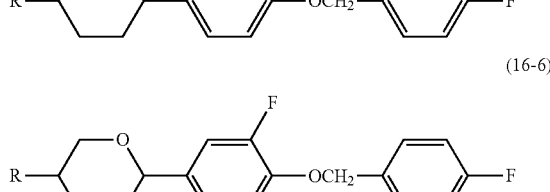
(16-7) 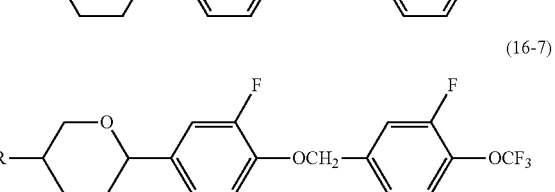
(16-8) 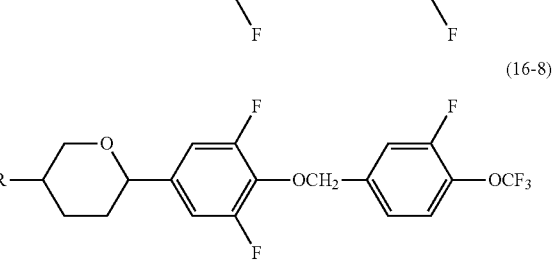

(16-9)
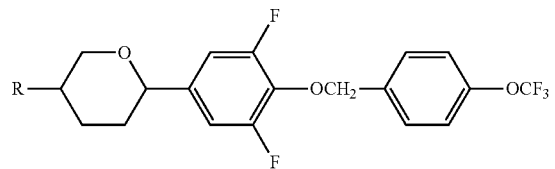
(16-10)
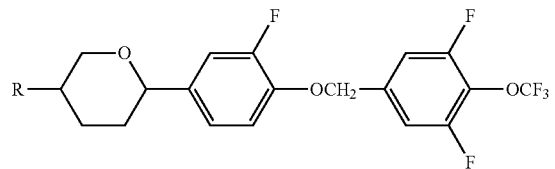
(16-11)
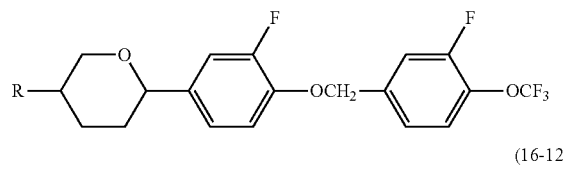
(16-12)
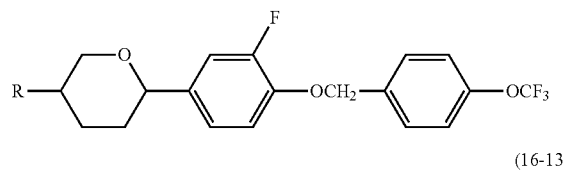
(16-13)
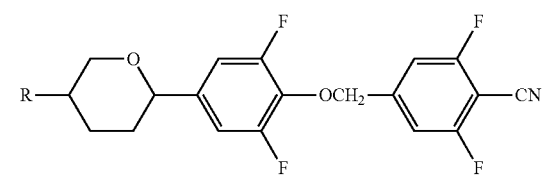
(16-14)
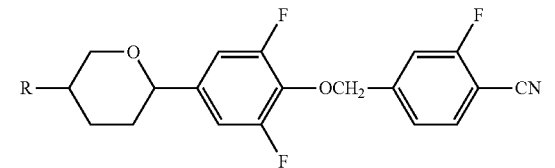
(16-15)
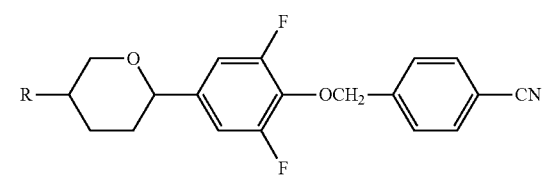
(16-16)
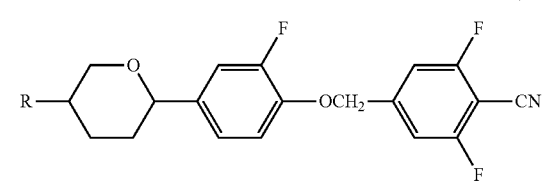
(16-17)
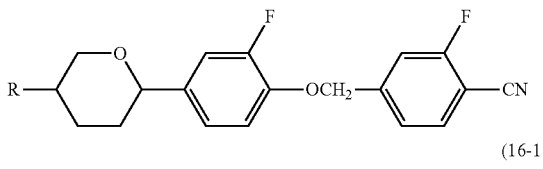
(16-18)
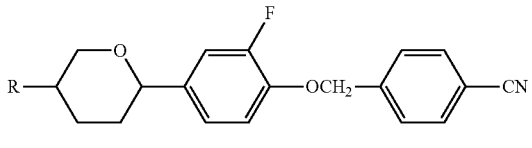
[Chem. 21]
(17-1)
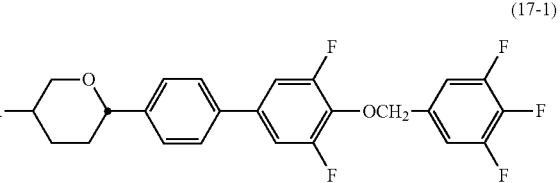
(17-2)
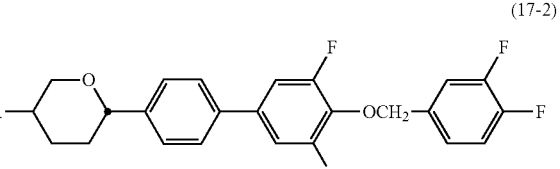
(17-3)
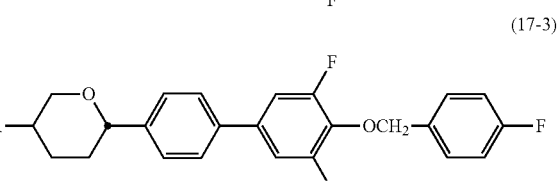
(17-4)
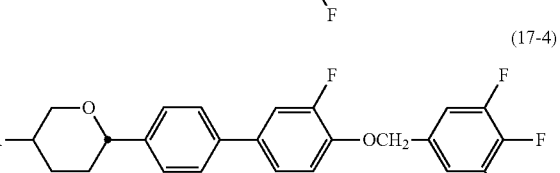
(17-5)
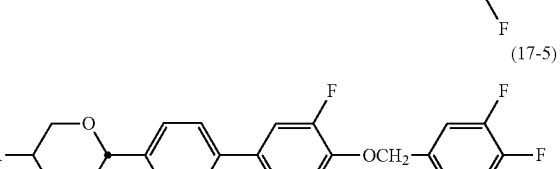
(17-6)
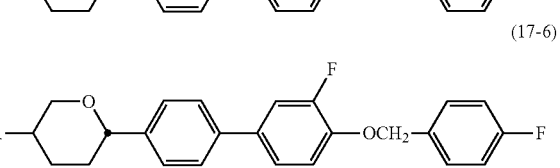
(17-7)
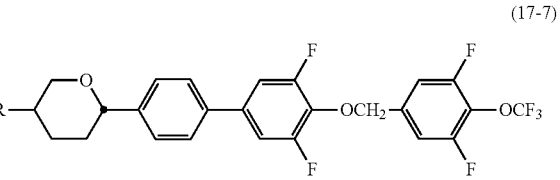

(17-8)
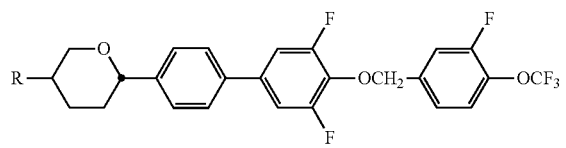
(17-9)
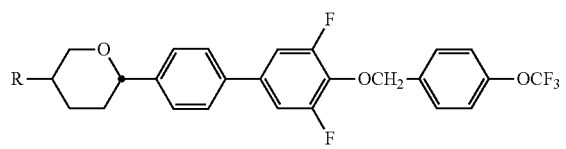
(17-10)
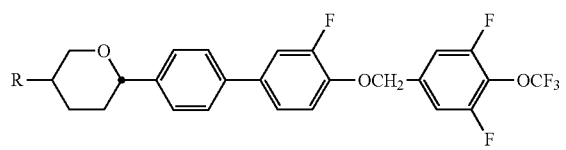
(17-11)
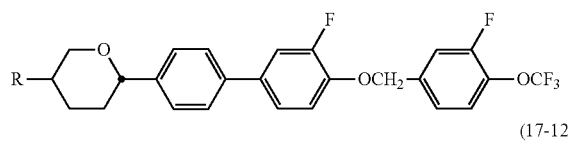
(17-12)
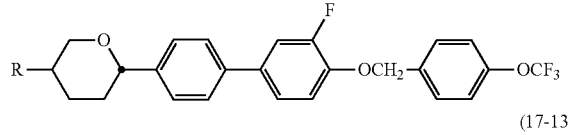
(17-13)
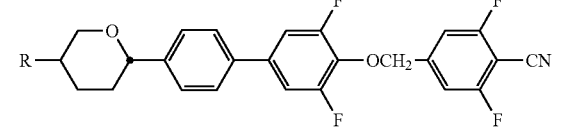
(17-14)
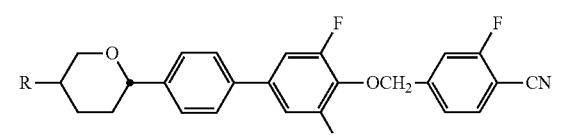
(17-15)
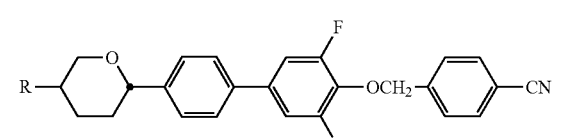
(17-16)
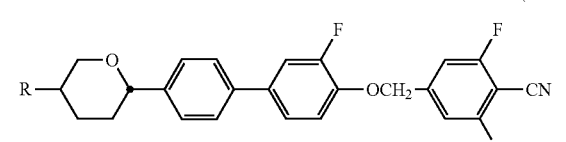
(17-17)
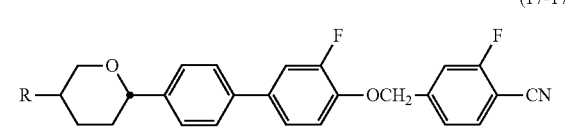
(17-18)
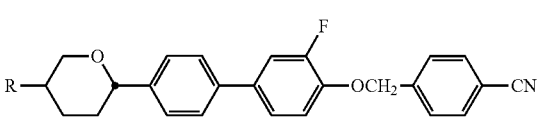
[Chem. 22]
(18-1)
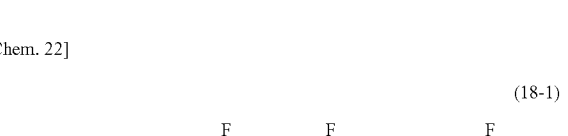
(18-2)
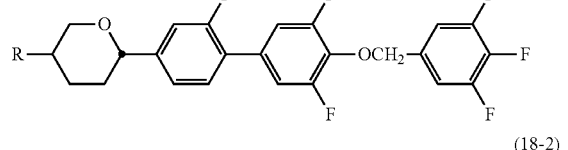
(18-3)
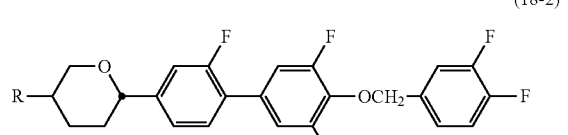
(18-4)
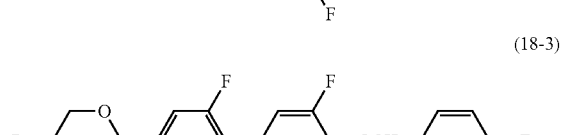
(18-5)
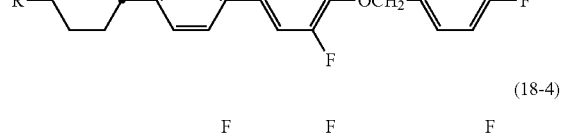
(18-6)
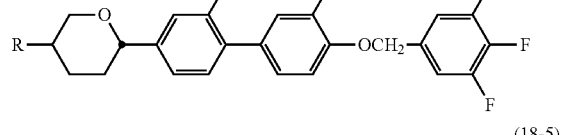
(18-7)
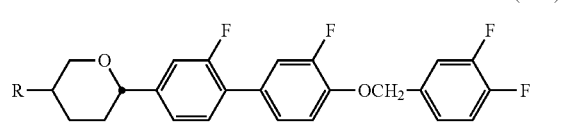
(18-8)
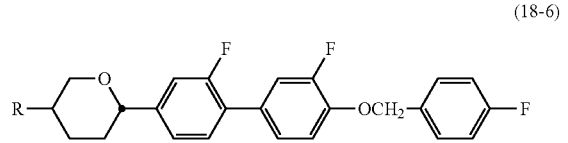

(18-9)
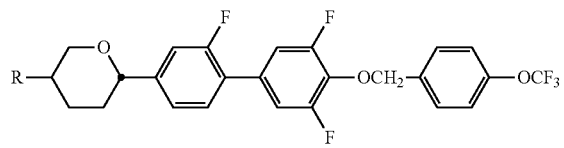
(18-10)
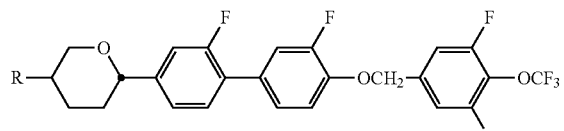
(18-11)
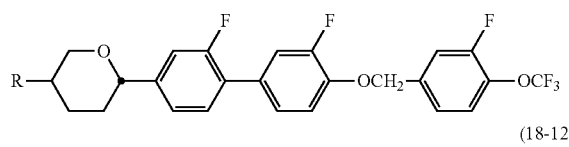
(18-12)
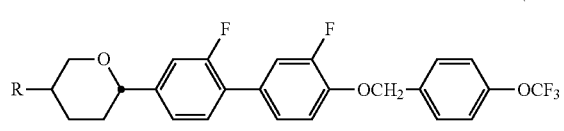
(18-13)
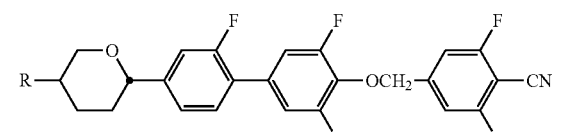
(18-14)
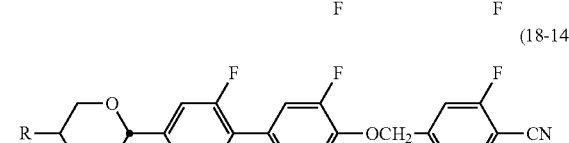
(18-15)
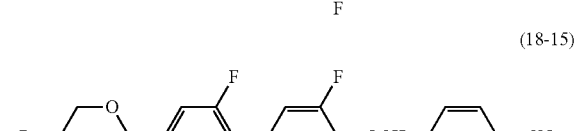
(18-16)
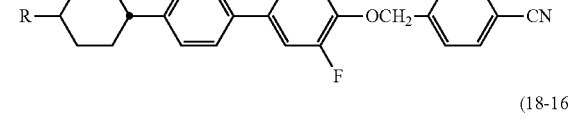
(18-17)
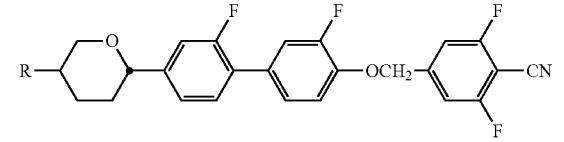
(18-18)
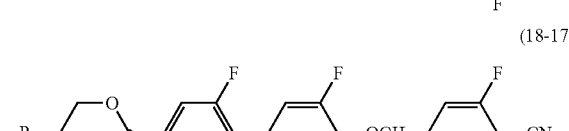
(18-19)
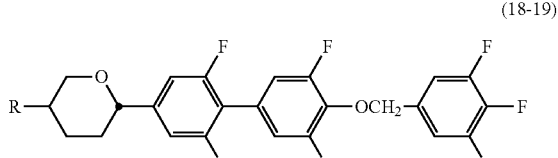
(18-20)
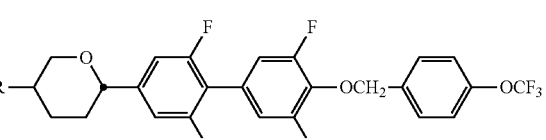
[Chem. 23]
(19-1)
(19-2)
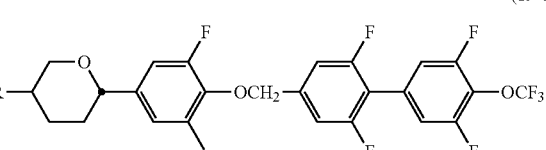
(19-3)
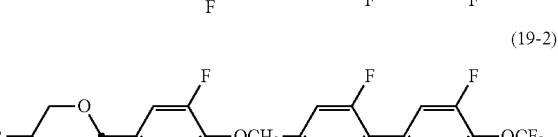
(19-4)
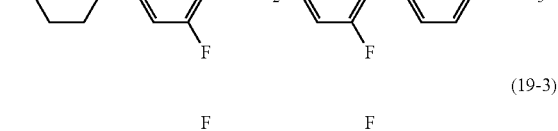
(19-5)
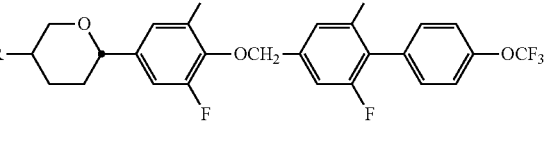
(19-6)
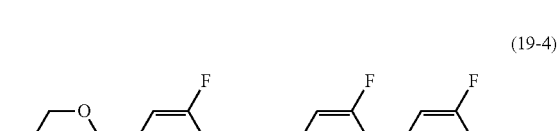

(19-7)
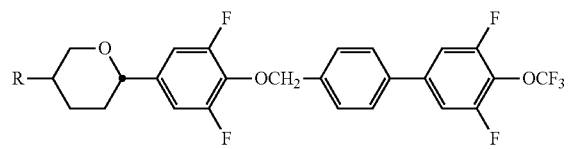
(19-8)
(19-9)
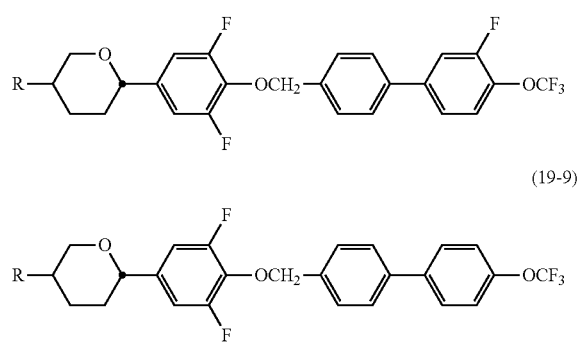
(19-10)
(19-11)
(19-12)
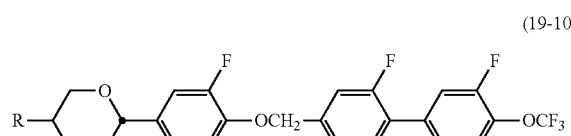
(19-13)
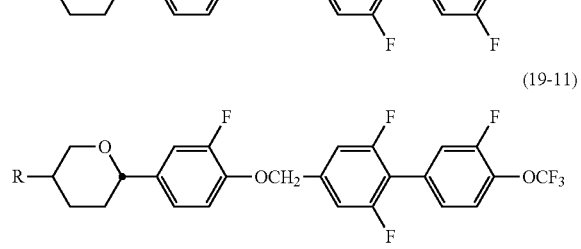
(19-14)
(19-15)
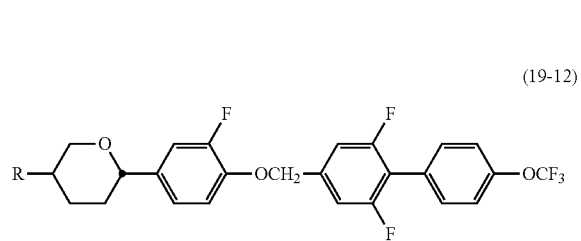
(19-16)
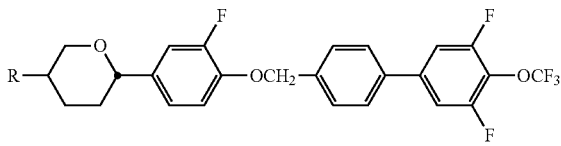
(19-17)
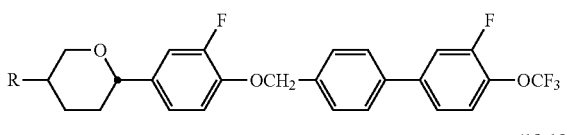
(19-18)
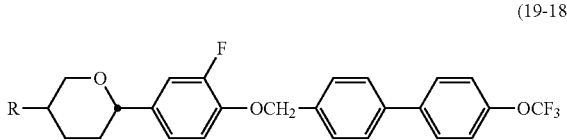
[Chem. 24]
(20-1)
(20-2)
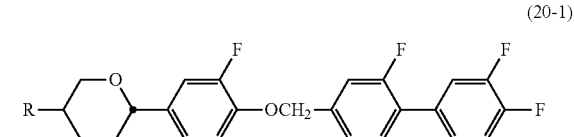
(20-3)
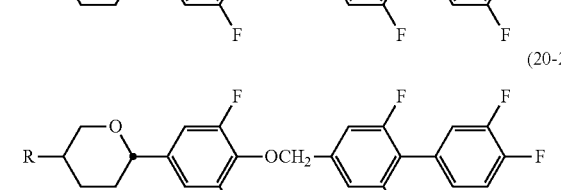
(20-4)
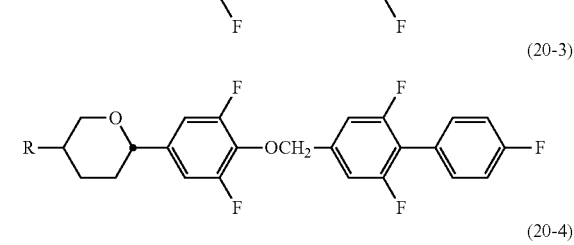
(20-5)
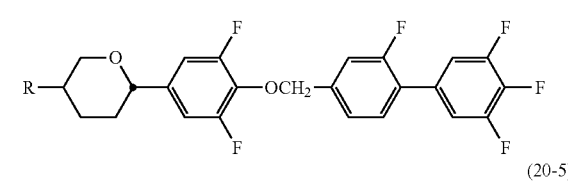
(20-6)
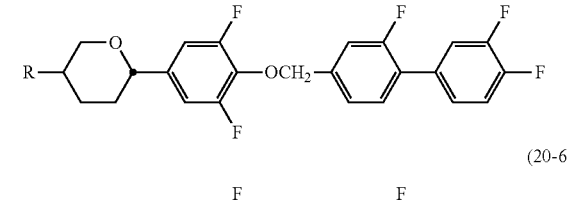
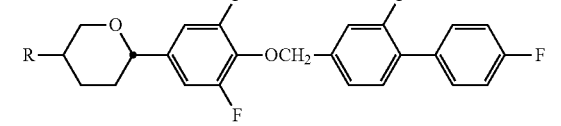

(20-7)
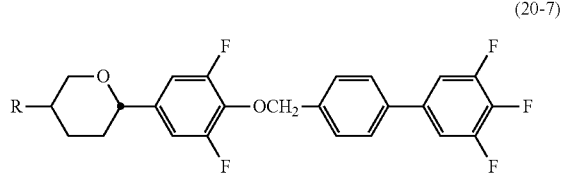

(20-8)
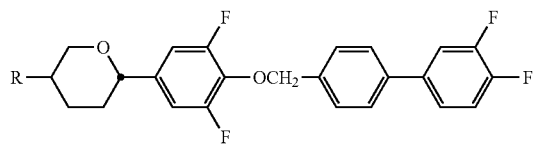

(20-9)
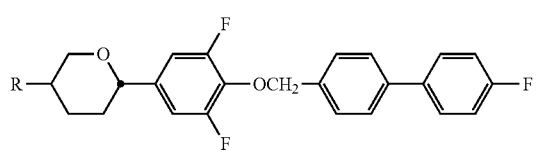

(20-10)
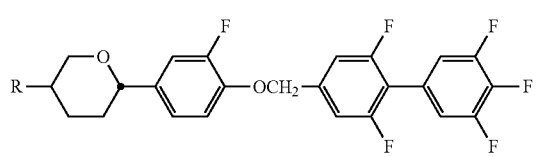

(20-11)
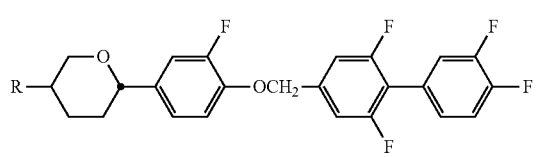

(20-12)
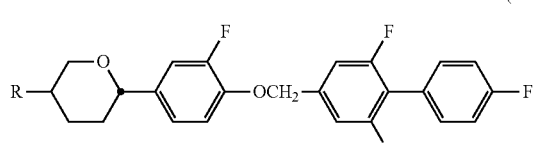

(20-13)
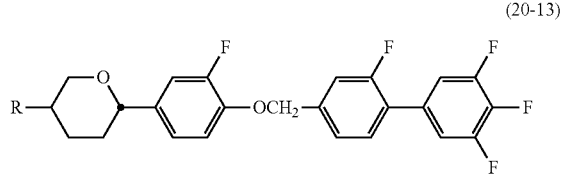

(20-14)
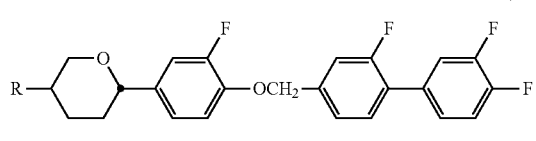

(20-15)
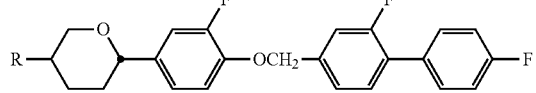

(20-16)
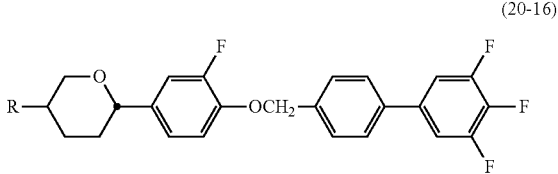

(20-17)
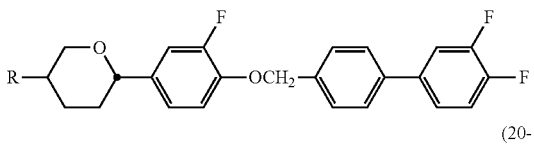

(20-18)
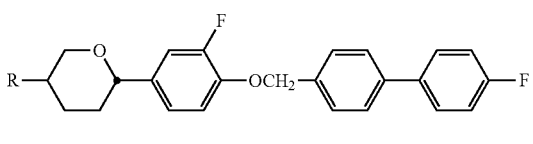

(In the formulae, R each independently represent an alkyl group having 1 to 12 carbon atoms, an alkenyl group having 2 to 12 carbon atoms, an alkoxy group having 1 to 12 carbon atoms, or an alkenyloxy group having 2 to 12 carbon atoms.)

Since a compound represented by general formula (1) present at a low content in a liquid crystal composition of the present invention does not exhibit its effect, the lower limit of the content in the composition is preferably 1% by mass ("%" in the composition represents "% by mass" hereinafter) or more, more preferably 2% or more, and still more preferably 5% or more. Also, a high content causes the problem of precipitation or the like, and thus the upper limit is preferably 50% or less, more preferably 30% or less, still more preferably 20% or less, and particularly preferably 10% or less. Only one compound represented by general formula (1) can be used, but two or more compounds may be simultaneously used.

A compound other than a compound represented by general formula (1) may be used for adjusting the physical property values of the liquid crystal composition, and if required, a compound not having a liquid crystal phase other than a compound having a liquid crystal phase may be added.

Preferred examples of a compound which can be used as a mixture with a compound represented by general formula (1) include second to fourth components described below as components other than at least one compound represented by general formula (1) and used as a first component in the composition provided by the present invention, and at least one of the second to fourth components is particularly preferably contained.

That is, the second component is a so-called fluorine-based (halogen-based) p-type liquid crystal compound, and examples thereof include compounds represented by general formulae (A1) to (A3) below.

[Chem. 25]

(A1)
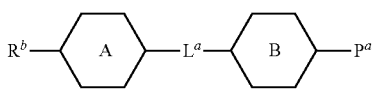

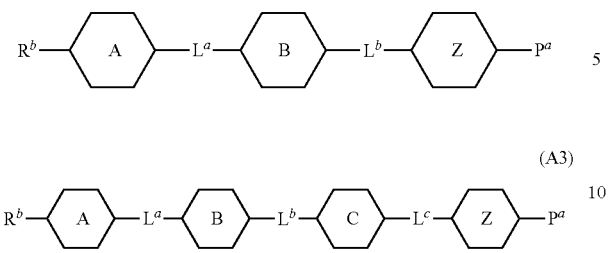

(A2)

(A3)

In the above formulae, $R^b$ represents an alkyl group having 1 to 12 carbon atoms, which may be linear or branched and may have a 3 to 6-membered ring structure, and in which any desired —$CH_2$— present in the group may be substituted by —O—, —CH=CH—, —CH=CF—, —CF=CH—, —CF=CF—, or —C≡C—, and any desired hydrogen atom present in the group may be substituted by a fluorine atom or a trifluoromethoxy group. However, a linear alkyl group having 1 to 7 carbon atoms, a linear 1-alkenyl group having 2 to 7 carbon atoms, a linear 3-alkenyl group 4 to 7 carbon atoms, or an alkyl group having 1 to 5 carbon atoms and an end substituted by an alkoxy group having 1 to 3 carbon atoms is preferred. When an asymmetric carbon is produced by branching, a compound may be either optically active or racemic.

Ring A, ring B, and ring C each independently represent a trans-1,4-cyclohexylene group, a transdecahydronaphthalene-trans-2,6-diyl group, a 1,4-phenylene group which may be substituted by at least one fluorine atom, a naphthalene-2,6-diyl group which may be substituted by at least one fluorine atom, a tetrahydronaphthalene-2,6-diyl group which may be substituted by at least one fluorine atom, a 1,4-cyclohexenylene group which may be substituted by a fluorine atom, a 1,3-dioxane-trans-2,5-diyl group, a pyrimidine-2,5-diyl group, or a pyridine-2,5-diyl group, but a trans-1,4-cyclohexylene group, a transdecahydronaphthalene-trans-2,6-diyl group, a naphthalene-2,6-diyl group which may be substituted by a fluorine atom, or a 1,4-phenylene group which may be substituted by 1 or two fluorine atoms is preferred. In particular, when the ring B is a trans-1,4-cyclohexylene group or transdecahydronaphthalene-trans-2,6-diyl group, the ring A is preferably a trans-1,4-cyclohexylene group, while when the ring C is a trans-1,4-cyclohexylene group or transdecahydronaphthalene-trans-2,6-diyl group, the ring B and ring A are preferably trans-1,4-cyclohexylene groups. In (A3), the ring A is preferably a trans-1,4-cyclohexylene group.

$L^a$, $L^b$, and $L^c$ are linkage groups and each independently represent a single bond, an ethylene group (—$CH_2CH_2$—), a 1,2-propylene group (—$CH(CH_3)CH_2$— and —$CH_2CH(CH_3)$—), a 1,4-butylene group, —COO—, —OCO—, —$OCF_2$—, —$CF_2O$—, —CH=CH—, —CH=CF—, —CF=CH—, —CF=CF—, —C≡C—, or —CH=NN=CH—, but a single bond, an ethylene group, a 1,4-butylene group, —COO—, —$OCF_2$—, —$CF_2O$—, —CF=CF—, or —C≡C— is preferred, and a single bond or an ethylene group is particularly preferred. Also, at least one of $L^a$ and $L^b$ in (A2) and at least two of $L^a$, $L^b$, and $L^c$ in (A3) preferably each represent a single bond.

Ring Z is an aromatic ring and is represented by any one of general formulae (La) to (Lc) below.

[Chem. 26]

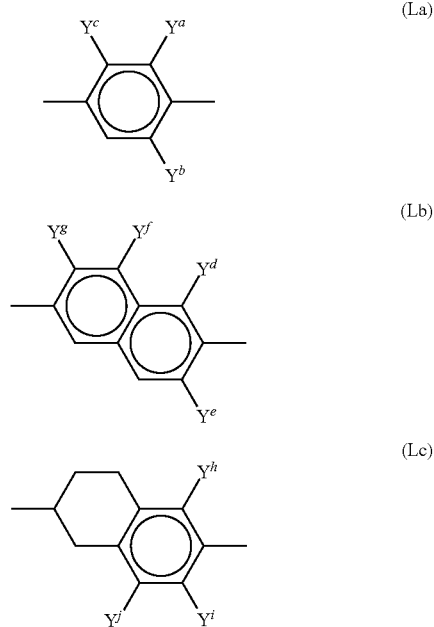

In the formulae, $Y^a$ to $Y^j$ each independently represent a hydrogen atom or a fluorine atom, but at least one of $Y^a$ and $Y^b$ in (La) is preferably a fluorine atom, at least one of $Y^d$ to $Y^f$ in (Lb) is preferably a fluorine atom, $Y^d$ is particularly preferably a fluorine atom, at least one of $Y^h$ and $Y^i$ in (Lc) is preferably a fluorine atom, and $Y^h$ is particularly preferably a fluorine atom.

Terminal group $P^a$ represents a fluorine atom, a chlorine atom, a trifluoromethoxy group, a difluoromethoxy group, a trifluoromethyl group or difluoromethyl group, an alkoxy group having 2 or 3 carbon atoms and substituted by two or more fluorine atoms, an alkyl group having 2 or 3 carbon atoms and substituted by two or more fluorine atoms, an alkenyl group having 2 or 3 carbon atoms and substituted by two or more fluorine atoms, or an alkenyloxy group having 2 or 3 carbon atoms and substituted by two or more fluorine atoms, but a fluorine atom, a trifluoromethoxy group, or a difluoromethoxy group is preferred, and a fluorine atom is particularly preferred.

The third component is a so-called cyano-based p-type liquid crystal compound, and examples thereof include compounds represented by general formulae (B1) to (B3) below.

[Chem. 27]

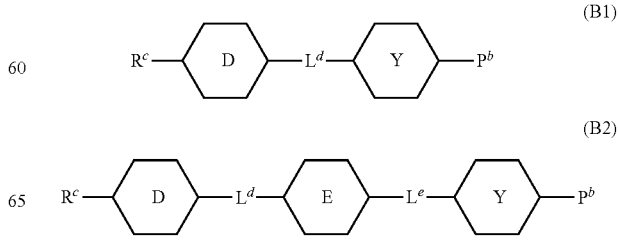

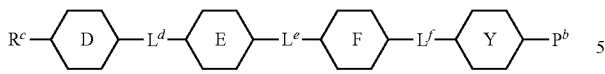
(B3)

In the above formulae, $R^c$ represents an alkyl group having 1 to 12 carbon atoms, which may be linear or branched and may have a 3 to 6-membered ring structure, and in which any desired —CH$_2$— present in the group may be substituted by —O—, —CH═CH—, —CH═CF—, —CF═CH—, —CF═CF—, or —C≡C—, and any desired hydrogen atom present in the group may be substituted by a fluorine atom or a trifluoromethoxy group. However, a linear alkyl group having 1 to 7 carbon atoms, a linear 1-alkenyl group having 2 to 7 carbon atoms, a linear 3-alkenyl group 4 to 7 carbon atoms, and an alkyl group having 1 to 5 carbon atoms and an end substituted by an alkoxy group having 1 to 3 carbon atoms are preferred. When an asymmetric carbon is produced by branching, a compound may be either optically active or racemic.

Ring D, ring E, and ring F each independently represent a trans-1,4-cyclohexylene group, a transdecahydronaphthalene-trans-2,6-diyl group, a 1,4-phenylene group which may be substituted by at least one fluorine atom, a naphthalene-2,6-diyl group which may be substituted by at least one fluorine atom, a tetrahydronaphthalene-2,6-diyl group which may be substituted by at least one fluorine atom, a 1,4-cyclohexenylene group which may be substituted by a fluorine atom, a 1,3-dioxane-trans-2,5-diyl group, a pyrimidine-2,5-diyl group, or a pyridine-2,5-diyl group, but a trans-1,4-cyclohexylene group, a transdecahydronaphthalene-trans-2,6-diyl group, a naphthalene-2,6-diyl group which may be substituted by a fluorine atom, or a 1,4-phenylene group which may be substituted by one or two fluorine atoms is preferred. In particular, when the ring E is a trans-1,4-cyclohexylene group or transdecahydronaphthalene-trans-2,6-diyl group, the ring D is preferably a trans-1,4-cyclohexylene group, while when the ring F is a trans-1,4-cyclohexylene group or transdecahydronaphthalene-trans-2,6-diyl group, the ring D and ring E are preferably trans-1,4-cyclohexylene groups. In (B3), the ring D is preferably a trans-1,4-cyclohexylene group.

$L^d$, $L^e$, and $L^f$ are linkage groups and each independently represent a single bond, an ethylene group (—CH$_2$CH$_2$—), a 1,2-propylene group (—CH(CH$_3$)CH$_2$— and —CH$_2$CH (CH$_3$)—), a 1,4-butylene group, —COO—, —OCO—, —OCF$_2$—, —CF$_2$O—, —CH═CH—, —CH═CF—, —CF═CH—, —CF═CF—, —C≡C—, —OCH$_2$—, —CH$_2$O—, or —CH═NN═CH—, but a single bond, an ethylene group, —COO—, —OCF$_2$—, —CF$_2$O—, —CF═CF—, or —C≡C— is preferred, and a single bond, an ethylene group, or —COO— is particularly preferred. Also, at least one of $L^d$ and $L^e$ in (B2) and at least two of $L^d$, $L^e$, and $L^f$ in (B3) preferably each represent a single bond.

$P^b$ represents a cyano group.

Ring Y is an aromatic ring and is represented by any one of general formulae (Ld) to (Lf) below.

[Chem. 28]

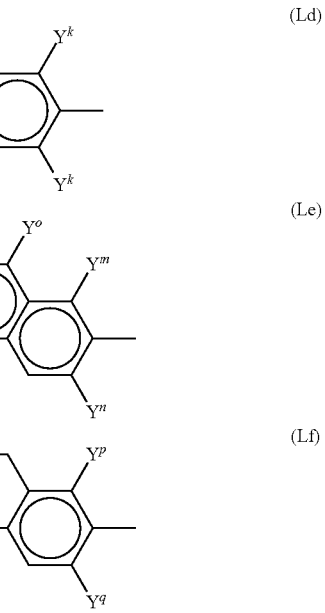

In the formulae, $Y^k$ to $Y^q$ each independently represent a hydrogen atom or a fluorine atom, but at least one of $Y^k$ and $Y^l$ in (Ld) is preferably a fluorine atom, at least one of $Y^m$ to $Y^o$ in (Le) is preferably a fluorine atom, $Y^m$ is particularly preferably a fluorine atom, at least one of $Y^p$ and $Y^q$ in (Lf) is preferably a fluorine atom, and $Y^p$ is particularly preferably a fluorine atom.

The fourth component is a so-called nonpolar liquid crystal compound having a dielectric anisotropy of about 0, and examples thereof include compounds represented by general formulae (C1) to (C3) below.

[Chem. 29]

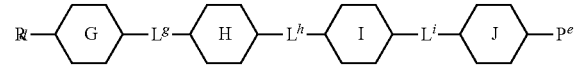

In the above formulae, $R^d$ and $P^e$ each independently represent an alkyl group having 1 to 12 carbon atoms, which may be linear or branched and may have a 3 to 6-membered ring structure, and in which any desired —CH$_2$— present in the group may be substituted by —O—, —CH═CH—, —CH═CF—, —CF═CH—, —CF═CF—, or —C≡C—, and any desired hydrogen atom present in the group may be substituted by a fluorine atom or a trifluoromethoxy group. However, a linear alkyl group having 1 to 7 carbon atoms, a linear 1-alkenyl group having 2 to 7 carbon atoms, a linear 3-alkenyl group 4 to 7 carbon atoms, a linear alkoxy group having 1 to 3 carbon atoms, or a linear alkyl group having 1 to 5 carbon atoms and an end substituted by an alkoxy group having 1 to 3 carbon atoms is preferred. Further, at least one of $R^d$ and $P^e$ is particularly preferably a linear alkyl group having 1 to 7 carbon atoms, a linear 1-alkenyl group having 2 to 7 carbon atoms, or a linear 3-alkenyl group having 4 to 7 carbon atoms.

Ring G, ring H, ring I, and ring J each independently represent a trans-1,4-cyclohexylene group, a transdecahydronaphthalene-trans-2,6-diyl group, a 1,4-phenylene group which may be substituted by one or two fluorine atoms or methyl groups, a naphthalene-2,6-diyl group which may be substituted by at least one fluorine atom, a tetrahydronaphthalene-2,6-diyl group which may be substituted by one or two fluorine atoms, a 1,4-cyclohexenylene group which may be substituted by one or two fluorine atoms, a 1,3-dioxane-trans-2,5-diyl group, a pyrimidine-2,5-diyl group, or a pyridine-2,5-diyl group, but each compound preferably has not more than one transdecahydronaphthalene-trans-2,6-diyl group, naphthalene-2,6-diyl group which may be substituted by at least one fluorine atom, tetrahydronaphthalene-2,6-diyl group which may be substituted by one or two fluorine atoms, 1,4-cyclohexenylene group which may be substituted by a fluorine atom, 1,3-dioxane-trans-2,5-diyl group, pyrimidine-2,5-diyl group, or pyridine-2,5-diyl group. The other rings are each preferably a trans-1,4-cyclohexylene group or a 1,4-phenylene group which may be substituted by one or two fluorine atoms or methyl groups. The total number of fluorine atoms present in the ring G, ring H, ring I, and ring J is preferably 2 or less and more preferably 0 or 1.

$L^g$, $L^h$, and $L^i$ are linkage groups and each independently represent a single bond, an ethylene group (—CH$_2$CH$_2$—), a 1,2-propylene group (—CH(CH$_3$)CH$_2$— and —CH$_2$CH (CH$_3$)—), a 1,4-butylene group, —COO—, —OCO—, —OCF$_2$—, —CF$_2$O—, —CH═CH—, —CH═CF—, —CF═CH—, —CF═CF—, —C≡C—, or —CH═NN═CH—, but a single bond, an ethylene group, a 1,4-butylene group, —COO—, —OCO—, —OCF$_2$—, —CF$_2$O—, —CF═CF—, —C≡C—, or —CH═NN═CH— is preferred, and at least one of $L^g$ and $L^h$ in (C2) and at least two of $L^g$, $L^h$, and $L^i$ in (C3) preferably each represent a single bond.

Compounds represented by general formulae (A1) to (A3) and compounds represented by general formulae (B1) to (B3) are excluded from compounds represented by general formulae (C1) to (C3).

Compounds represented by general formulae (A1) to (A3) and compounds represented by general formulae (B1) to (B3) and general formulae (C1) to (C3) never have a structure in which heteroatoms are directly bonded to each other.

Compounds represented by general formula (1) can be produced as described below. Of course, the gist and application range of the present invention are not limited to the production example.

(Method 1)

A compound represented by general formula (13)

[Chem. 30]

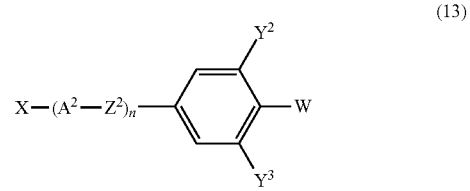

(in the formula, $A^2$ represents a 1,4-phenylene group which may be substituted by at least one fluorine, $Z^2$, n, $Y^2$, $Y^3$, and W each independently represent the same meaning as in general formula (1), and X represents a chlorine atom, a bromine atom, or an iodine atom) is reacted with a metallic reagent or alkyl metal to produce an organometallic reagent, which is then reacted with N,N-dimethylformamide and then hydrolyzed to produce a benzaldehyde derivative represented by general formula (14),

[Chem. 31]

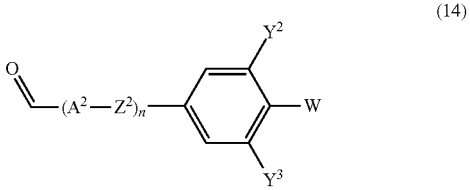

(in the formula, $A^2$ represents a 1,4-phenylene group which may be substituted by at least one fluorine, and $Z^2$, n, $Y^2$, $Y^3$, and W each independently represent the same meaning as in general formula (1)).

Any solvent may be used as long as reaction is allowed to appropriately proceed, but an ether solvent such as tetrahydrofuran, diethyl ether, or the like is preferred.

Any reagent may be used for preparing the organometallic reagent as long as reaction is allowed to appropriately proceed. When the metallic reagent is used, magnesium metal, lithium metal, or zinc metal is preferred, and when the alkylmetal reagent is used, normal butyl lithium, secondary butyl lithium, tertiary butyl lithium, or lithium diisopropylamide is preferred.

Any reaction temperature may be used for preparing the organometallic reagent as long as reaction is allowed to appropriately proceed, but a temperature of –76° C. to about a reflux temperature of the solvent is preferred. Any reaction temperature may be used for reaction with dimethylformamide as long as reaction is allowed to appropriately proceed, but a temperature of –76° C. to room temperature is preferred, and a temperature of –40° C. to 10° C. is more preferred.

In order to produce a compound containing a 1,4-cyclohexylene group or 2,6-dioxane-1,4-cyclohexylene group as $A^2$ in the general formula (14), phosphorus ylide prepared by reacting a methoxymethyl triphenylphosphine salt with a base is reacted with a compound represented by general formula (15),

[Chem. 32]

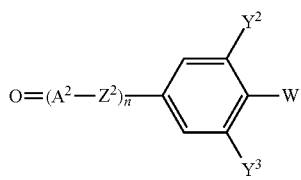

(15)

(in the formula, $A^2$ represents a 1,4-cyclohexylene group or a 2,6-dioxane-1,4-cyclohexylene group, and $Z^2$, n, $Y^2$, $Y^3$, and W each independently represent the same meaning as in general formula (1)) and then hydrolyzed with an acid aqueous solution.

Any solvent may be used as long as reaction is allowed to appropriately proceed, but an ether solvent such as diethyl ether, tetrahydrofuran, or the like is preferred.

Any reaction temperature may be used as long as reaction is allowed to appropriately proceed, but a range from −40° C. to room temperature is preferred.

Preferred examples of the base include metal hydrides such as sodium hydride and the like, alkali metal alkoxides such as sodium methoxide, sodium ethoxide, tertiary butoxide, and the like, alkyl lithium such as normal butyl lithium secondary butyl lithium, and the like.

Next, a carbonyl group of the compound represented by general formula (14) is reduced with a reducing agent to produce a methanol derivative represented by general formula (16),

[Chem. 33]

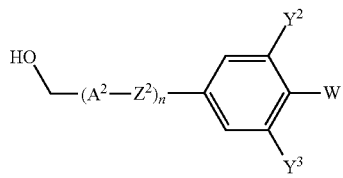

(16)

(in the formula, $A^2$, $Z^2$, n, $Y^2$, $Y^3$, and W each independently represent the same meaning as in general formula (1)).

Preferred examples of the reducing agent include lithium aluminum hydrides such as lithium aluminum hydride, bis(methoxyethoxy)aluminum lithium dihydride, and the like, and tetrahydroborates such as sodium tetrahydroborate, lithium tetrahydroborate, and the like.

When a lithium aluminum hydride is used, any solvent may be used as long as reaction is allowed to appropriately proceed, but an ether solvent such as tetrahydrofuran, diethyl ether, or the like is preferred. When a teerahydroborate is used, any solvent may be used as long as reaction is allowed to appropriately proceed, but an ether solvent such as tetrahydrofuran, diethyl ether, or the like, or an alcohol solvent such as methanol, ethanol, or the like is preferred, and a small amount of water is more preferably added.

Any reaction temperature may be used as long as reaction is allowed to appropriately proceed, but a temperature of 0° C. to the reflux temperature of the solvent is preferred.

Next, a compound represented by general formula (17),

[Chem. 34]

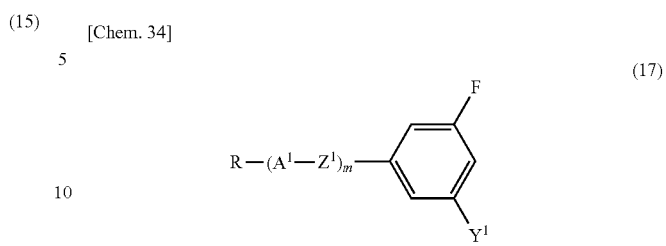

(17)

(in the formula, R, $A^1$, $Z^1$, m, and $Y^1$ each independently represent the same meaning as in general formula (1)) is reacted with a base to induce a phenyllithium which is then reacted with a borate, hydrolyzed, and then oxidized with an oxidizing agent to produce a phenol derivative represented by general formula (18),

[Chem. 35]

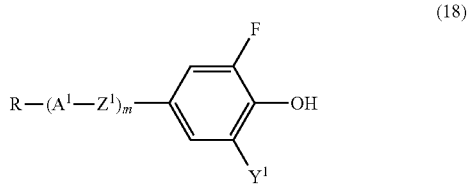

(18)

(in the formula, R, $A^1$, $Z^1$, m, and $Y^1$ each independently represent the same meaning as in general formula (1)).

Any solvent may be used as long as reaction is allowed to appropriately proceed, but an ether solvent such as tetrahydrofuran, diethyl ether, or the like is preferred.

Any reaction temperature may be used for inducing phenyllithium as long as reaction is allowed to appropriately proceed, but a temperature of −78° C. to −10° C. is preferred, and a temperature of −40° C. to −20° C. is more preferred. Any reaction temperature may be used for reaction with a borate as long as reaction is allowed to appropriately proceed, but a temperature of −40° C. to −10° C. is preferred. Any temperature may be used for oxidation as long as reaction is allowed to appropriately proceed, but a temperature of −10° C. to 40° C. is preferred.

Any base may be used as long as reaction is allowed to appropriately proceed, but alkyl lithium such as normal butyl lithium, secondary butyl lithium, or the like, or lithium amide such as lithium diisopropylamide, lithium dibutylamide, or the like is preferred.

Any borate may be used as long as reaction is allowed to appropriately proceed, but trimethyl borate or triisopropyl borate is preferred.

Any oxidizing agent may be used as long as reaction is allowed to appropriately proceed, but hydrogen peroxide, performic acid, peracetic acid, or perbenzoic acid is preferred.

Next, the methanol derivative represented by general formula (16) is condensed with the phenol derivative represented by general formula (18) in the presence of triphenylphosphine and azodicarboxylic acid ester, producing a compound represented by general formula (1).

Any solvent may be used as long as reaction is allowed to appropriately proceed, but an ether solvent such as tetrahydrofuran, diethyl ether, or the like, or a chlorinated solvent such as dichloromethane, chloroform, or the like is preferred.

Any reaction temperature may be used as long as reaction is allowed to appropriately proceed, but a temperature of −20° C. to room temperature is preferred.

Any azodicarboxylic acid ester may be used as long as reaction is allowed to appropriately proceed, but diethyl azodicarboxylate or diisopropyl azodicarboxylate is preferred.

EXAMPLES

The present invention is described in further detail below by giving examples, but the present invention is not limited to these examples.

A phase transition temperature was measured by using a polarizing microscope provided with a temperature control stage and a differential scanning calorimeter (DSC).

In examples and comparative examples below, "%" in a composition represents "% by mass".

$T_{n-i}$ represents a nematic-isotropic phase transition temperature.

Compounds are described by using abbreviations below.
THF: tetrahydrofuran
DMF: N,N-dimethylformamide
DIAD: diisopropyl azodicarboxylate
TPP: triphenylphosphine
PTSA: p-toluenesulfonic acid
NBS: N-bromosuccinic acid imide
BPO: benzoyl peroxide
Me: methyl group, Pr: n-propyl group, Bu: n-butyl group Example 1

Production of (3,4,5-trifluorophenyl)-[2,6-difluoro-4-(4-propylphenyl)phenyloxy]methane (1-1)

[Chem. 36]

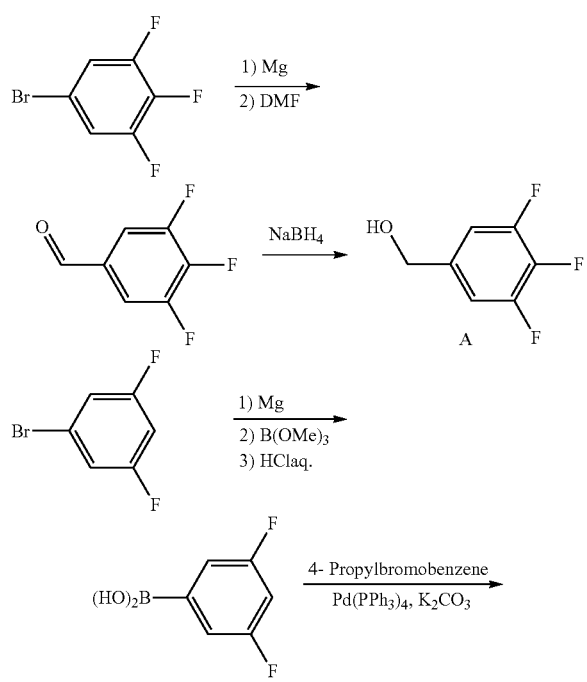

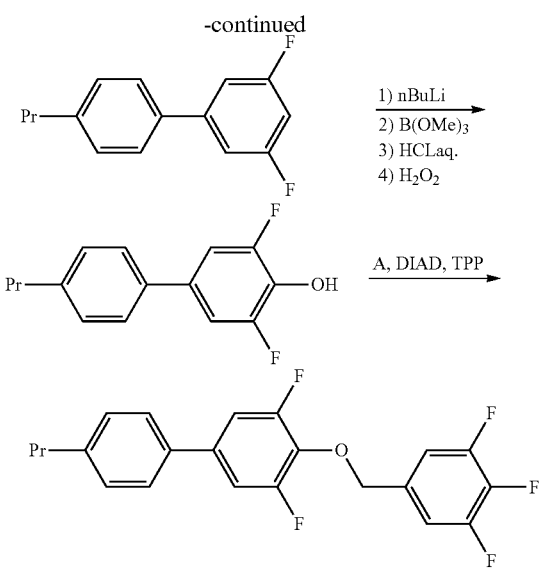

(1-1) In a nitrogen atmosphere, a solution prepared by dissolving 50 g of 3,4,5-trifluorobromobenzene in 50 mL of THF was added dropwise at a rate that caused gentle reflux to a mixed solution of 6.34 g of magnesium and 60 mL of THF. After dropwise addition, the mixture was stirred at 40° C. for 1 hour. Then, a solution prepared by dissolving 34.64 g of DMF in 60 mL of THF was added dropwise under ice cooling at such a rate that the inside temperature did not exceed 20° C., followed by stirring at room temperature for 1 hour. Then, 10% hydrochloric acid was added until the reaction system became acidic, and the mixture was stirred at room temperature for 1 hour. Then, hexane was added to the mixture to separate an organic layer, and an aqueous layer was subjected to extraction with hexane. The hexane extract was combined with the organic layer and washed with a saturated aqueous sodium bicarbonate solution and saturated brine. The resultant mixture was dried by adding sodium sulfate, and then the solvent was distilled off under reduced pressure to yield 37.91 g of 3,4,5-trifluorobenzaldehyde.

(1-2) Then, 37.91 g of 3,4,5-trifluorobenzaldehyde and 10 mL of water were dissolved in 50 mL of ethanol and cooled with ice, and 2.69 g of sodium tetrahydroborate was slowly added to the resultant solution. The mixture was stirred at room temperature for 2 hours, and 10% hydrochloric acid was added until the system became acidic, followed by stirring for 1 hour. Then, hexane was added to the mixture to separate an organic layer, and an aqueous layer was subjected to extraction with hexane. The hexane extract was combined with the organic layer and washed with saturated brine. The resultant mixture was dried by adding sodium sulfate, and then the solvent was distilled off under reduced pressure. Then, reduced-pressure distillation (3.9 kPa, b. p.=116° C. to 118° C.) yielded 26.73 g of 3,4,5-trifluorobenzyl alcohol (A).

(1-3) In a nitrogen atmosphere, a solution prepared by dissolving 100 g of 3,5-difluorobromobenzene in 150 mL of THF was added dropwise at a rate that caused gentle reflux to a mixed solution of 13.85 g of magnesium and 55 mL of THF. After dropwise addition, the mixture was stirred at 40° C. for 1 hour and cooled with ice. Then, a solution prepared by dissolving 64.59 g of trimethoxyborane in 130 mL of THF was slowly added dropwise under ice cooling, followed by stirring at room temperature for 1 hour. Then, 10% hydrochloric acid was added until the reaction system became acidic, and the mixture was stirred at room temperature for 30 minutes. Then, an organic layer was separated from the mixture, and an aqueous layer was subjected to extraction with hexane. The hexane extract was combined with the organic layer and washed with saturated brine. The resultant mixture was dried by adding sodium sulfate, and then the solvent was distilled off under reduced pressure to yield 71.65 g of 3,5-difluorophenylboronic acid.

(1-4) In a nitrogen atmosphere, a solution prepared by mixing 90.33 g of 4-propylbromobenzene, 2.62 g of tetrakis-triphenylphosphine palladium, 240 mL of an aqueous potassium carbonate solution (2 mol/L), and 450 mL of THF was heated to 60° C., and 71.65 g of 3,5-difluorophenylboronic acid was added to the solution over 30 minutes. The resultant mixture was stirred at 60° C. for 30 minutes and then allowed to cool. Then, hexane was added to the mixture to separate an organic layer, and the organic layer was washed with saturated brine and dried by adding sodium sulfate. Then, the solvent was distilled off under reduced pressure, and the residue was purified by silica gel column chromatography to yield 104.92 g of 3,5-difluoro-1-(4-propylphenyl)benzene.

(1-5) In a nitrogen atmosphere, 10.00 g of 3,5-difluoro-1-(4-propylphenyl)benzene was dissolved in 50 mL of THF, and the resultant solution was cooled to −40° C. Then, 30 mL of butyl lithium (1.6 mol/L, hexane solution) was added at such a rate that the inside temperature did not exceed −35° C. After stirring at −40° C. for 1 hour, 5.37 g of trimethoxyborane was added at such a rate that the inside temperature did not exceed −35° C. After stirring at −40° C. for 1 hour, the inside temperature was increased to room temperature, and 10% hydrochloric acid was added until the reaction system became acidic. Then, an organic layer was separated from the mixture, and an aqueous layer was subjected to extraction with toluene. The toluene extract was combined with the organic layer and cooled with ice, and 11.71 g of a 15% aqueous hydrogen peroxide solution was added to the mixture, followed by stirring at room temperature for 15 hours. Further, an organic layer was separated from the mixture, and an aqueous layer was subjected to extraction with toluene. The toluene extract was combined with the organic layer and washed with a 10% aqueous sodium sulfite solution and saturated brine. The resultant mixture was dried by adding sodium sulfate, and then the solvent was distilled off under reduced pressure. The residue was recrystallized from ethanol to yield 10.24 g of 2,6-difluoro-4-(4-propylphenyl)phenol.

(1-6) In a nitrogen atmosphere, 10.24 g of 2,6-difluoro-4-(4-propylphenyl)phenol produced in (1-5), 6.69 g of 3,4,5-trifluorobenzyl alcohol produced in (1-2), and 12.44 g of triphenylphosphine were dissolved in 40 mL of THF, and the resultant solution was cooled to −20° C., and 9.18 g of DIAD was added dropwise at a such a rate that the inside temperature did not exceed −10° C. After stirring at room temperature for 1 hour, the solvent was distilled off under reduced pressure. The residue was suspended by adding hexane, and triphenylphosphine was filtered off. An organic layer was washed with saturated brine and dried by adding sodium sulfate. Then, the solvent was distilled off under reduced pressure, and the residue was purified by silica gel column chromatography and then recrystallized from ethanol to yield 11.58 g of (3,4,5-trifluorophenyl)-[2,6-difluoro-4-(4-propylphenyl)phenyloxy]methane.

MS m/z: 392[M$^+$]

Phase transition temperature (° C.): Cr 68.5 Iso $^1$HNMR (CDCl$_3$, TMS internal standard) δ (ppm)=7.41 (2H, d, J=8.4 Hz), 7.25 (2H, d, J=8.0 Hz), 7.16-7.08 (4H, m), 5.10 (2H, s), 2.62 (2H, t, J=7.6 Hz), 1.72-1.63 (2H, m), 0.96 (3H, t, J=7.2 Hz)

Example 2

Production of (3,4-difluorophenyl)-[2,6-difluoro-4-(4-propylphenyl)phenyloxy]methane (1-2)

[Chem. 37]

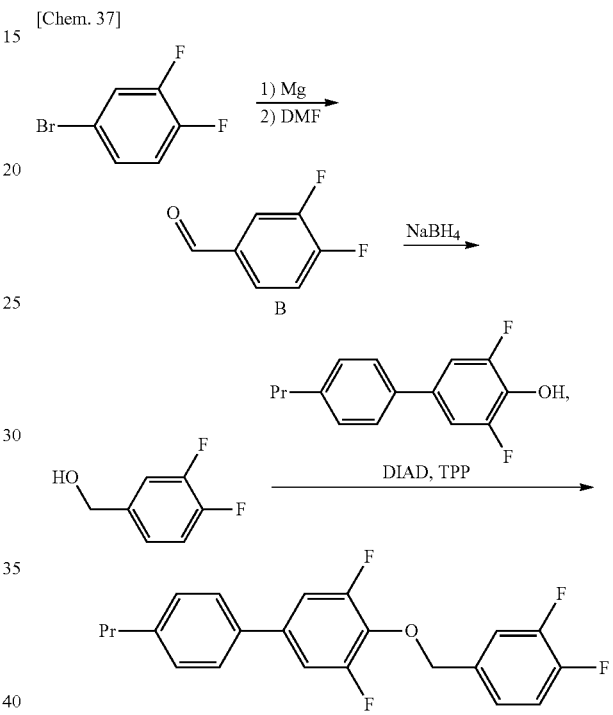

According to the same method as in Example 1 except that 3,4-difluorobromobenzene was used in place of 3,4,5-trifluorobromobenzene used in Example 1, 9.14 g of (3,4-difluorophenyl)-[2,6-difluoro-4-(4-propylphenyl)phenyloxy]methane was yielded.

MS m/z: 374 [M$^+$]

Example 3

Production of (3,4,5-trifluorophenyl)-[2,6-difluoro-4-(trans-4-propylcyclohexyl)phenyloxy]methane (2-1)

[Chem. 38]

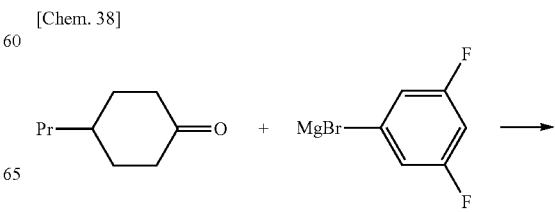

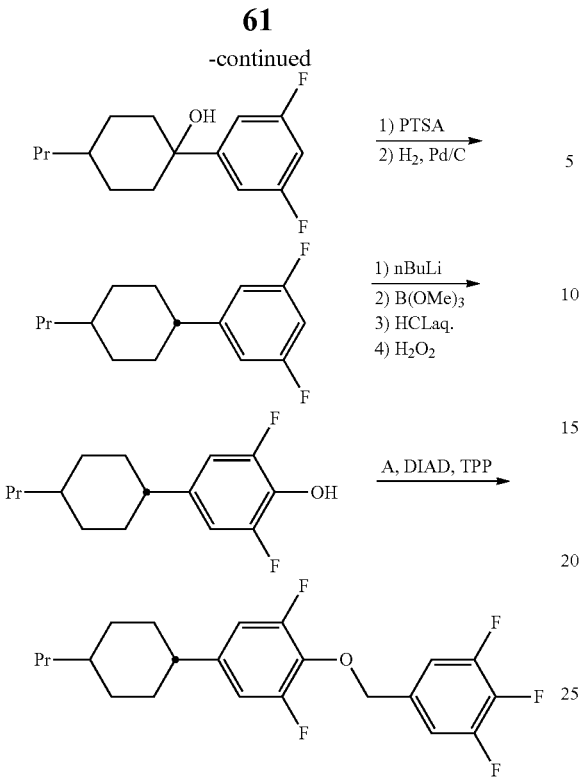

(3-1) In a nitrogen atmosphere, a solution prepared by dissolving 75.85 g of 3,5-difluorobromobenzene in 150 mL of THF was added at a rate that caused gentle reflux to a solution prepared by suspending 10.03 g of magnesium in 50 mL of THF, followed by stirring at 40° C. for 1 hour. After the resultant mixture was allowed to cool to room temperature, a solution prepared by dissolving 60.62 g of 4-propylcyclohexanone in 120 mL of THF was added to the mixture at such a rate that the inside temperature did not exceed 35° C., followed by stirring at room temperature for 2 hours. Then, 10% hydrochloric acid was added until the reaction system became acidic, and an organic layer was separated from the mixture. Further, an aqueous layer was subjected to extraction with toluene, and the toluene extract was combined with organic layer and washed with saturated brine. The resultant mixture was dried by adding sodium sulfate, and then the solvent was distilled off under reduced pressure to yield 132 g of crude 1-(1-hydroxy-4-propylcyclohexyl)-3,5-difluorobenzene.

(3-2) In a nitrogen atmosphere, 132 g of crude 1-(1-hydroxy-4-propylcyclohexyl)-3,5-difluorobenzene and 2.99 g of p-toluenesulfonic monohydrate were dissolved in 250 mL of toluene, and the resultant solution was stirred for 2 hours under reflux while the produced water was removed. After the solution was allowed to cool to room temperature, an organic layer was washed with a saturated aqueous sodium bicarbonate solution and saturated brine, and dried by adding sodium sulfate, and then the solvent was distilled off under reduced pressure. Then, the whole amount of the resultant residue was dissolved in 280 mL of ethyl acetate, and 7.1 g of palladium 5%/carbon was added to the solution, followed by stirring in a hydrogen atmosphere at 5 Mpa for 6 hours. After the palladium catalyst was filtered off, the solvent was distilled off under reduced pressure, and the residue was purified by silica gel column chromatography. Then, the whole amount of the resultant product and 3.39 g of tertiary butoxypotassium were dissolved in 350 mL of DMF, followed by stirring at room temperature for 4 hours. Then, water and hexane were added to separate an organic layer. Further, an aqueous layer was subjected to extraction with hexane, and the hexane extract was combined with the organic layer and washed with saturated brine. The resultant mixture was dried by adding sodium sulfate, the solvent was distilled off, and distillation under reduced pressure (206 Pa, b. p.=110° C. to 112° C.) yielded 58.05 g of 1-(trans-4-propylcyclohexyl)-3,5-difluorobenzene.

(3-3) The subsequent steps were performed by the same method as in Example 1 except that 1-(trans-4-propylcyclohexyl)-3,5-difluorobenzene was used in place of 3,5-difluoro-1-(4-propylphenyl)benzene used in Example 1, thereby yielding 12.51 g of (3,4,5-trifluorophenyl)-[2,6-difluoro-4-(trans-4-propylcyclohexyl)phenyloxy].

MS m/z: 398 [M+]

Phase transition temperature (° C.) Cr Iso $^1$HNMR (CDCl$_3$, TMS internal standard) δ (ppm)=7.08 (2H, d, J=6.8 Hz), 6.75 (2H, d, J=9.6 Hz), 5.03 (2H, s), 2.41-2.35 (1H, m), 1.87-1.83 (4H, m), 1.39-1.17 (7H, m), 1.07-0.93 (2H, m), 0.90 (3H, t, J=7.2 Hz)

Example 4

Production of (3,4,5-trifluorophenyl)-[2,6-difluoro-4-[4-(trans-4-propylcyclohexyl)phenyl]phenyloxy] methane (6-1)

[Chem. 39]

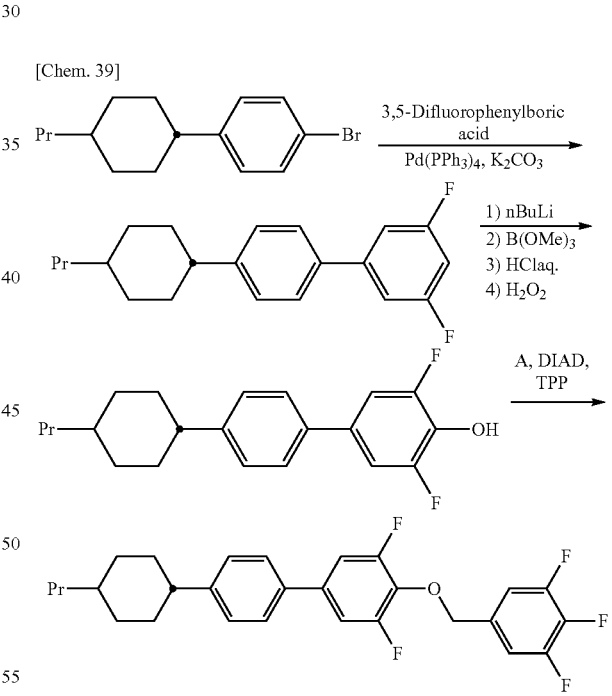

(4-1) According to the same method as in Example 1 except that 4-(trans-4-propylcyclohexyl)bromobenzene was used in place of 4-propylbromobenzene used in Example 1, 9.14 g of α-[4-(4-(4-propylcyclohexyl)phenyl)-2,6-difluorophenyloxy]-3,4,5-trifluorotoluene was yielded.

MS m/z: 474 [M+]

Phase transition temperature (° C.): Cr 83.4 N 146.2 Iso $^1$HNMR (CDCl$_3$, TMS internal standard) δ (ppm)=7.42 (2H, d, J=8.4 Hz), 7.28 (2H, d, J=8.0 Hz), 7.15-7.09 (4H, m), 5.10 (2H, s), 2.54-2.46 (1H, m), 1.90 (4H, t, J=11.2 Hz), 1.52-1.38 (2H, m), 1.37-1.26 (3H, m), 1.24-1.19 (2H, m), 1.12-1.01 (2H, m), 0.91 (3H, t, J=6.8 Hz)

Example 5

Production of (3,4-difluorophenyl)-[2,6-difluoro-4-[4-(trans-4-propylcyclohexyl)phenyl]phenyloxy]methane (6-2)

[Chem. 40]

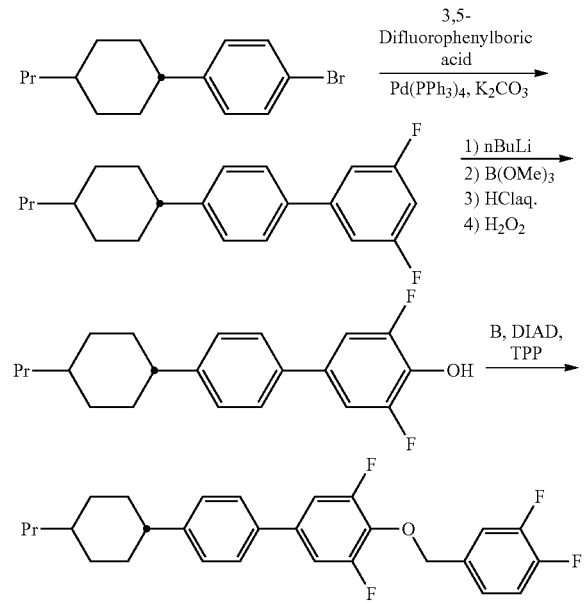

(5-1) According to the same method as in Example 4 except that 3,4-difluorobenzyl alcohol (B) was used in place of 3,4,5-trifluorobenzyl alcohol (A) used in Example 4, 8.52 g of α-[4-(4-(4-propylcyclohexyl)phenyl)-2,6-difluorophenyloxy]-3,4-difluorotoluene was yielded.

MS m/z: 456 [M+]

Phase transition temperature (° C.): Cr 70.8 N 166.9 Iso $^1$HNMR (CDCl$_3$, TMS internal standard) δ (ppm)=7.42 (2H, d), 7.35-7.29 (1H, m), 7.27 (2H, d), 7.20-7.13 (2H, m), 7.11 (2H, d), 5.12 (2H, s), 2.50 (1H, tt), 1.89 (4H, t), 1.52-1.42 (2H, m), 1.38-1.26 (3H, m), 1.25-1.91 (2H, m), 1.11-1.01 (2H, m), 0.91 (3H, t)

Example 6

Production of (3,4,5-trifluorophenyl)-[2-fluoro-4-(4-propylphenyl)phenyloxy]methane (1-4)

[Chem. 41]

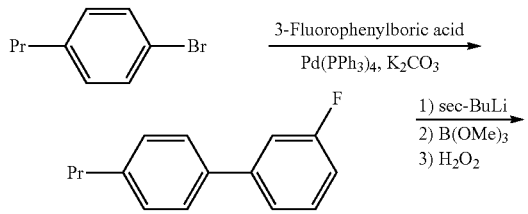

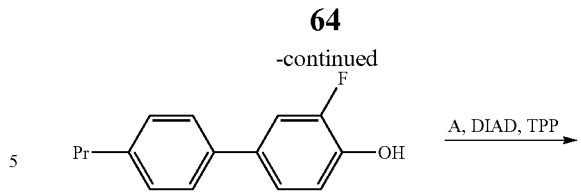

-continued (6-1) In a nitrogen atmosphere, a solution prepared by mixing 50.00 g of 4-propylbromobenzene, 0.87 g of tetrakistriphenylphosphine palladium, 60 mL of an aqueous potassium carbonate solution (2 mol/L), and 150 mL of THF was heated to 60° C., and 35.14 g of 3-fluorophenylboronic acid was added to the solution over 20 minutes. After the resultant mixture was stirred at 60° C. for 3 hours, the mixture was allowed to cool, and an organic layer was separated by adding hexane. The organic layer was washed with saturated brine and dried by adding sodium sulfate, and then the solvent was distilled off under reduced pressure. As a result of purification by silica gel column chromatography, 44.32 g of 3-fluoro-1-(4-propylphenyl)benzene was produced.

(6-2) In a nitrogen atmosphere, 44.32 g of 3-fluoro-1-(4-propylphenyl)benzene was dissolved in 220 mL of THF, the resultant solution was cooled to −74° C., and 210 mL of secondary butyl lithium (1.0 mol/L, hexane solution) was added at such a rate that the inside temperature did not exceed −60° C. After stirring at −74° C. for 1 hour, 23.64 g of trimethoxyborane was added at such a rate that the inside temperature did not exceed −60° C. After stirring at −74° C. for 1 hour, the inside temperature was increased to room temperature, and 10% hydrochloric acid was added until the system became acidic. Then, an organic layer was separated, and an aqueous layer was subjected to extraction with toluene. The toluene extract was combined with the organic layer and cooled with ice, and 54 g of a 15% aqueous hydrogen peroxide solution was added to the mixture, followed by stirring under ice cooling for 3 hours. Further, an organic layer was separated, and an aqueous layer was subjected to extraction with toluene. The toluene extract was combined with the organic layer and washed with a 10% aqueous sodium sulfite solution and saturated brine. The organic layer mixture was dried by adding sodium sulfate, and then the solvent was distilled off under reduced pressure. The residue was recrystallized from hexane to yield 41.01 g of 2-fluoro-4-(4-propylphenyl)phenol.

(6-3) The subsequent steps were performed by the same method as in Example 1 except that 2-fluoro-4-(4-propylphenyl)phenol was used in place of 2,6-difluoro-4-(4-propylphenyl)phenol used in Example 1, thereby yielding 22.56 g of (3,4,5-trifluorophenyl)-[2-fluoro-4-(4-propylphenyl)phenyloxy]methane.

MS m/z: 374 [M+]

Example 7

Production of [2,6-difluoro-4-(4-propylphenyl)phenyloxy]-[4-(3,4,5-trifluorophenyl)phenyl]methane (9-10)

[Chem. 42]

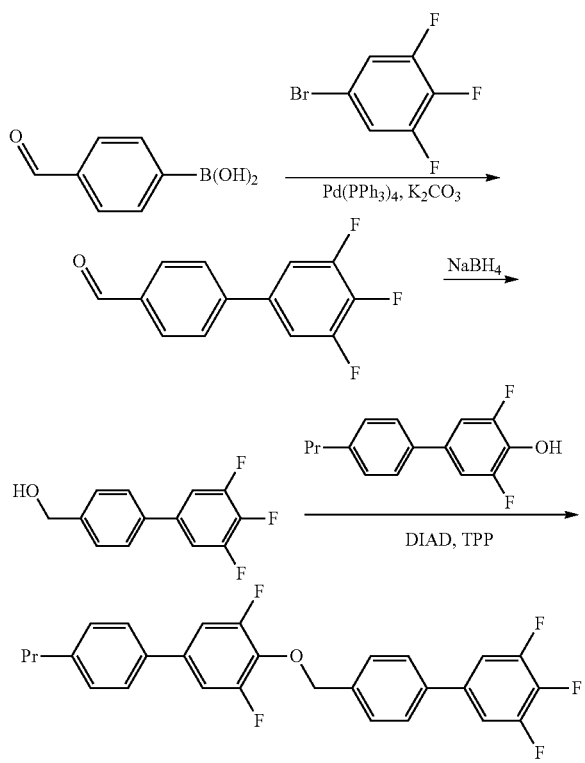

(7-1) In a nitrogen atmosphere, a solution prepared by mixing 15.00 g of 3,4,5-trifluorobromobenzene, 0.25 g of tetrakis-triphenylphosphine palladium, 30 mL of an aqueous potassium carbonate solution (2 mol/L), and 75 mL of THF was heated to 60° C., and 10.71 g of 4-formylphenylboric acid was added to the solution over 20 minutes. After the resultant mixture was stirred at 60° C. for 3 hours, the mixture was allowed to cool, and an organic layer was separated by adding hexane. The organic layer was washed with saturated brine and dried by adding sodium sulfate, and then the solvent was distilled off under reduced pressure. As a result of purification by silica gel column chromatography, 14.77 g of 4-(3,4,5-trifluorophenyl)benzaldehyde was yielded.

(7-2) Then, 14.77 g of 4-(3,4,5-trifluorophenyl)benzaldehyde and 15 mL of water were dissolved in 70 mL of ethanol, the resultant solution was cooled with ice, and 0.75 g of sodium tetrahydroborate was slowly added. After stirring at room temperature for 2 hours, 10% hydrochloric acid was added until the system became acidic, followed by stirring for 1 hour. Then, toluene was added to the mixture to separate an organic layer, and an aqueous layer was subjected to extraction with toluene. The toluene extract was combined with the organic layer and washed with saturated brine. The organic layer mixture was dried by adding sodium sulfate, and then the solvent was distilled off under reduced pressure. The residue was recrystallized from hexane to yield 12.64 g of 4-(3,4,5-trifluorophenyl)benzyl alcohol.

(7-3) The subsequent steps were performed by the same method as in Example 1 except that 4-(3,4,5-trifluorophenyl)benzyl alcohol was used in place of 3,4,5-trifluorobenzyl alcohol used in Example 1, thereby yielding 7.53 g of [2,6-difluoro-4-(4-propylphenyl)phenyloxy]-[4-(3,4,5-trifluorophenyl)phenyl]methane.

MS m/z: 468 [M+]

Example 8

Production of (4-trifluoromethoxyphenyl)-[2,6-difluoro-4-(4-propylphenyl)phenyloxy]methane (1-9)

[Chem. 43]

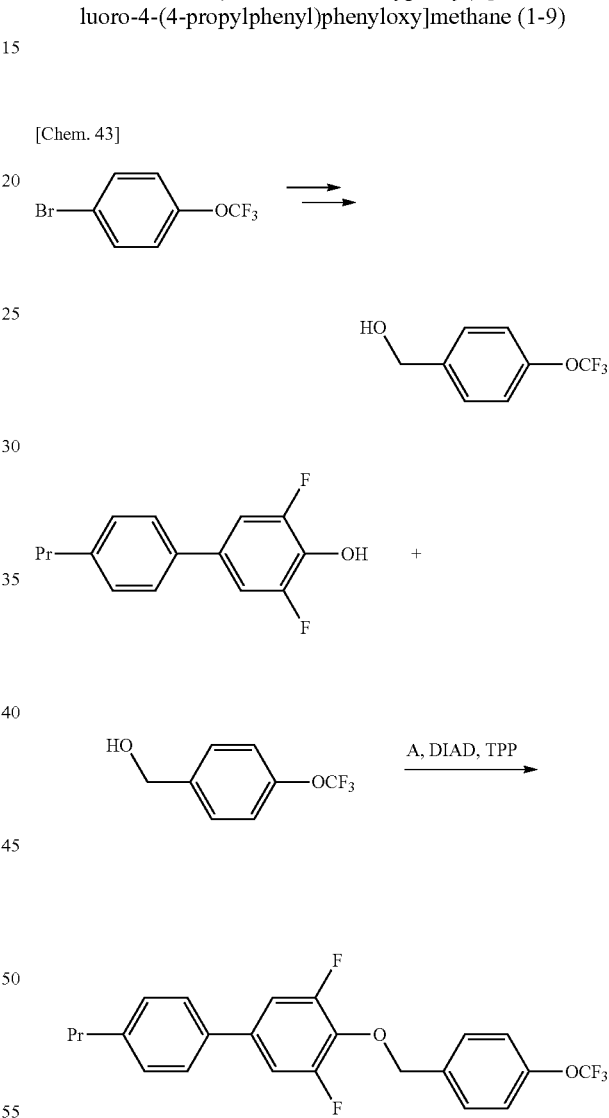

(8-1) According to the same method as in Example 1 except that 4-trifluoromethoxybromobenzene was used in place of 3,4,5-trifluorobromobenzene used in Example 1, (4-trifluoromethoxyphenyl)-[2,6-difluoro-4-(4-propylphenyl)phenyloxy]methane was yielded.

MS m/z: 422 [M+]

Phase transition temperature (° C.): Cr (66.2 SmA) Iso

$^1$HNMR (CDCl$_3$, TMS internal standard) δ (ppm)=7.51 (2H, d, J=8.4 Hz), 7.42 (2H, d, J=8.0 Hz), 7.25-7.22 (4H, m), 7.12 (2H, d, J=9.6 Hz), 5.18 (2H, s), 2.62 (2H, t, J=7.6 Hz), 1.72-1.62 (2H, m), 0.96 (3H, t, J=7.2 Hz)

Example 9

Production of (3,4,5-trifluorophenyl)-[2,6-difluoro-4-(4-(4-propylcyclohexyl)phenyl)phenyloxy]methane (7-19)

[Chem. 44]

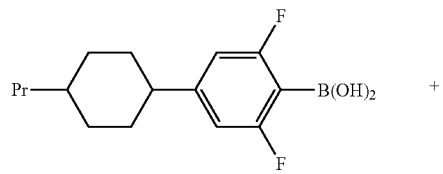

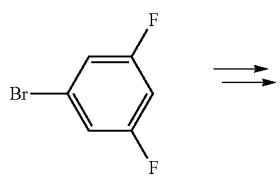

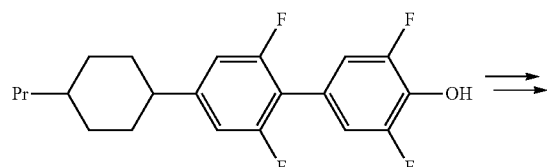

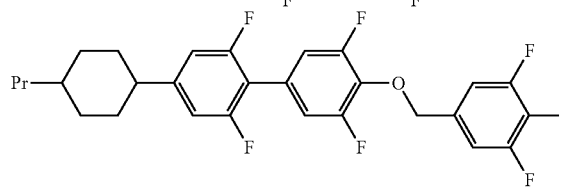

According to the same method as in Examples 1 to 8, (3,4,5-trifluorophenyl)-[2,6-difluoro-4-(4-(4-propylcyclohexyl)phenyl)phenyloxy]methane was yielded.

MS m/z: 510 [M+]

Phase transition temperature (° C.): Cr 95 N 104 Iso $^1$HNMR (CDCl$_3$, TMS internal standard) δ (ppm)=7.13 (2H, dd, J1=7.4 Hz, J2=6.7 Hz), 7.05 (2H, d, J=8.9 Hz), 6.84 (4H, d, J=9.3 Hz), 5.13 (2H, s), 2.48 (1H, tt, J1=12.2 Hz, J2=3.2 Hz), 1.92-1.87 (4H, m), 1.47-1.87 (7H, m), 1.10-1.00 (2H, m), 0.90 (3H, t, J=7.1 Hz)

Example 10

Production of 3,5-difluoro-4-(3,4,5-trifluorophenyl)phenyl-[2,6-difluoro-4-(4-propylcyclohexyl)phenyloxy]methane (13-1)

[Chem. 45]

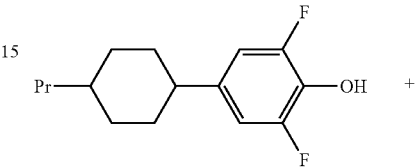

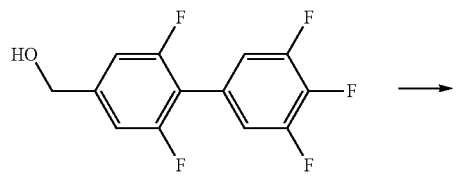

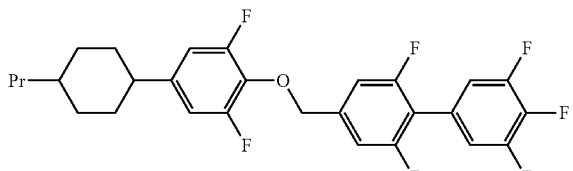

According to the same method as in Examples 1 to 8, 3,5-difluoro-4-(3,4,5-trifluorophenyl)phenyl-[2,6-difluoro-4-(4-propylcyclohexyl)phenyloxy]methane was yielded.

MS m/z: 510 [M+]

Phase transition temperature (° C.): Cr 110.5 Iso $^1$HNMR (CDCl$_3$, TMS internal standard) δ (ppm)=7.16-7.08 (4H, m), 6.77 (2H, d, J=9.6 Hz), 5.11 (2H, s), 2.43-2.37 (1H, m), 1.86 (4H, d, J=11.0 Hz), 1.41-1.26 (5H, m), 1.23-1.17 (2H, m), 1.07-0.97 (2H, m), 0.90 (3H, t, J=7.2 Hz)

Example 11

Production of 4-[3,5-difluoro-4-(3,4,5-trifluorophenyl)phenyl]cyclohexyl-(2,6-difluoro-4-propylphenyloxy)methane (15-5)

[Chem. 46]

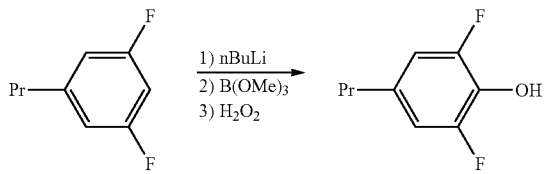

-continued

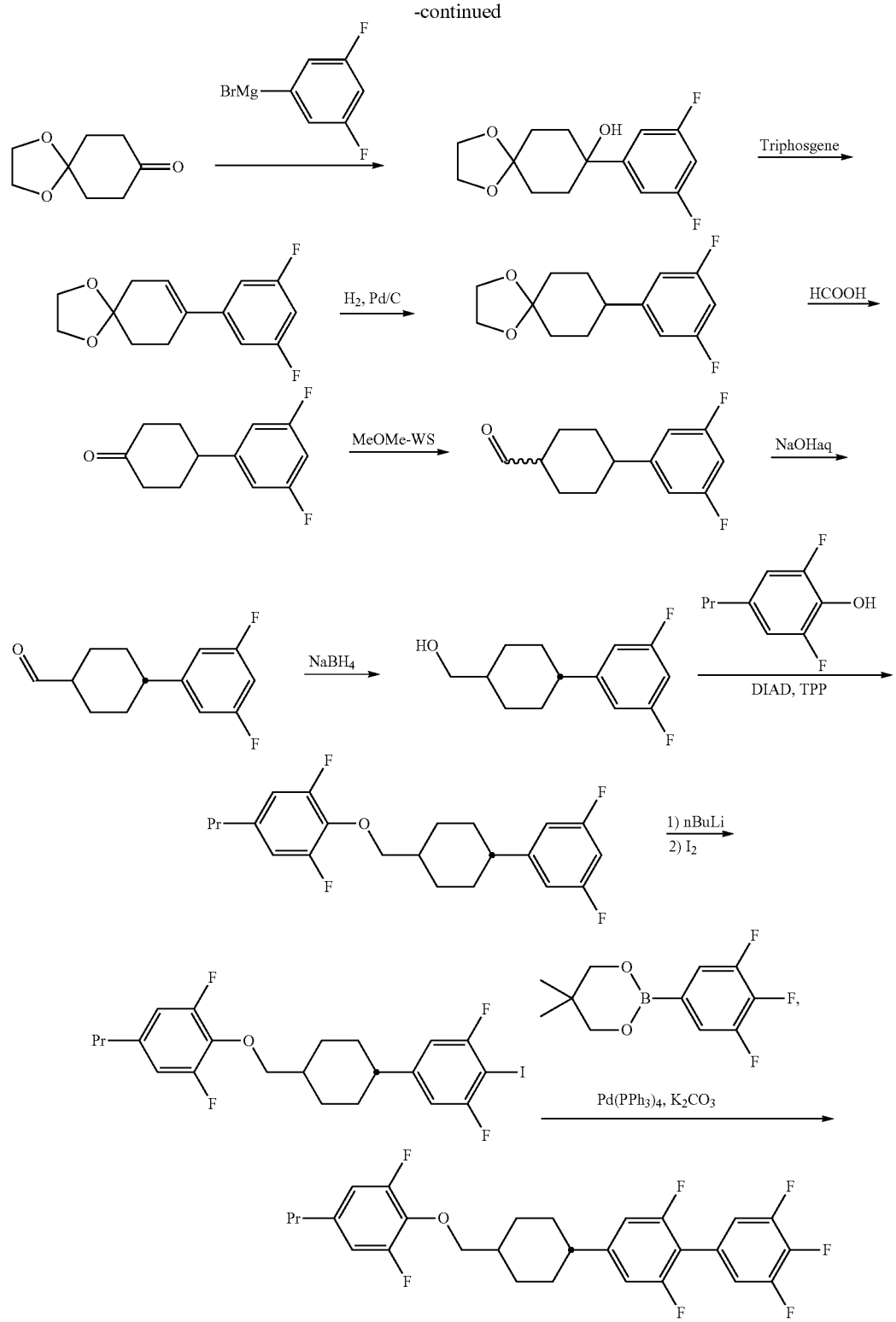

(11-1) In a nitrogen atmosphere, 3,5-difluoropropylbenzene (134 g, synthesized by the same method as in Molecular Crystals and Liquid Crystals, 1995, 260, 93-106) was dissolved in THF (650 mL), and the resultant solution was cooled to −40° C. or less. Then, a 1.6 mol/L n-butyl lithium hexane solution (640 mL) was added to the solution at such a rate that the inside temperature was not more than −35° C., followed by further stirring at −40° C. for 1 hour. Then, a solution prepared by dissolving trimethylboric acid (116 g) in THF (350 mL) was added at −40° C. and such a rate that the inside temperature was not more than −35° C. The resultant mixture was slowly heated to room temperature and further stirred at room temperature for 30 minutes, and then 10% hydrochloric acid (400 mL) was added under ice cooling to separate an organic layer which was then washed with saturated brine. Then, a 15% aqueous hydrogen peroxide solution (215 g) was slowly added, followed by stirring under heating at 40° C. for 6 hours. After cooling with ice, a 20% aqueous sodium sulfite solution (300 mL) was added to the mixture at such a rate that the inside temperature did not exceed 20° C., and an organic layer was separated. Further an aqueous layer was subjected to extraction with ethyl acetate (500 mL), and the ethyl acetate extract was combined with the organic layer, washed with saturated brine, and dried by adding sodium sulfate. After the solvent was distilled off under reduced pressure, hexane (800 mL) was added to the residue, an insoluble substance was filtered off, and a filtrate was concentrated under reduced pressure to yield 2,6-difluoro-4-propylphenol (123 g) as a yellow liquid.

MS m/z: 172 [M$^+$]

$^1$HNMR (CDCl$_3$, TMS internal standard) δ (ppm)=6.68 (2H, d, J=8.4 Hz), 2.49 (2H, t, J=7.2 Hz), 1.59 (2H, quinted, j=7.4 Hz), 0.92 (3H, t, J=7.3 Hz)

(11-2) In an argon atmosphere, 20.3 g of magnesium was suspended in THF (40 mL), and a solution of 3,5-difluorobromobenzene (149 g) in THF (450 mL) was added dropwise to the resultant suspension at an inside temperature of 40 to 65° C. After stirring at room temperature for 1 hour, a solution of 1,4-cyclohexanedione monoethylene ketal (100 g) in THF (300 mL) was added dropwise at an inside temperature of 40 to 60° C., followed by stirring at room temperature for 1 hour. Then, water (250 mL), 10% hydrochloric acid (200 mL), and 750 mL of toluene were added in that order, and the mixture was stirred at room temperature for 30 minutes to separate an organic layer. The organic layer was washed with saturated brine two times, and then dried with anhydrous sodium sulfate. The solvent was distilled off under reduced pressure to yield 178 g of 4-(3,5-difluorophenyl)-4-hydroxycyclohexanone ethylene ketal as a light yellow solid.

(11-3) In an argon atmosphere, 4-(3,5-difluorophenyl)-4-hydroxycyclohexanone ethylene ketal (178 g) and 120 g of pyridine were dissolved in 700 mL of toluene, and a solution of 68 g of triphosgene in toluene (2767 mL) was added dropwise to the resultant solution at an inside temperature of 22° C. or less. After stirring at an inside temperature of 20 to 25° C. for 2 hours, the mixture was poured into water (800 mL). An organic layer was washed with water (300 mL) two times and with saturated brine (300 mL) two times in that order to yield a toluene solution of 1-(3,5-difluorophenyl)-4-cyclohexenone ethylene ketal.

(11-4) Then, 15 g of palladium 5% on carbon (contenting 50% of water) was added to the solution yielded in 11-3, and the mixture was stirred for 4 hours in an autoclave at a hydrogen pressure of 0.4 MPa and an outside temperature of 40° C. The catalyst was filtered off, and the resultant solution was concentrated to some extent to yield a toluene solution of 4-(3,5-difluorophenyl)cyclohexanone ethylene ketal.

(11-5) Then, 500 mL of formic acid was added to the solution produced in 11-4, and the mixture was stirred for 4 hours at an inside temperature of 40° C. Then, 500 mL of water was added to the mixture and stirred, and an organic layer was washed with saturated brine, a saturated aqueous sodium bicarbonate solution, and saturated brine in that order, and then dried with anhydrous sodium sulfate. The solvent was distilled off under reduced pressure to yield 119 g of 4-(3,5-difluorophenyl)cyclohexanone as a light yellow solid.

(11-6) In an argon atmosphere, 263 g of methoxymethyl triphenylphosphonium chloride was suspended in THF (800 mL), and 90 g of potassium-tert-butoxide was added the resultant suspension at an inside temperature of 0° C. or less, followed by stirring at an inside temperature of 0° C. for 20 minutes. Then, a solution of 4-(3,5-difluorophenyl)cyclohexanone (119 g) in THF (300 mL) was added at an inside temperature of 5° C. or less, followed by stirring at an inside temperature of −5 to 8° C. for 30 minutes. After water (10 mL) was added, the solvent was distilled off under reduced pressure, and water (400 mL), methanol (400 mL), hexane (500 mL), and 7.3 g of a 70% aqueous tert-butyl hydroperoxide solution were added to the residue, followed by stirring at room temperature for 1 hour. An organic layer was separated and an aqueous layer was subjected to extraction with hexane. The hexane extract was combined with the organic layer and washed with a 50% aqueous methanol solution and water two times in that order, and the solvent was distilled off under reduced pressure. Then, 10% hydrochloric acid (400 mL) and THF (400 mL) were added to the resultant residue, followed by heating under reflux for 1 hour. An organic layer was separated and an aqueous layer was subjected to extraction with ethyl acetate. The ethyl acetate extract was combined with the organic layer and washed with saturated brine two times. The solvent was distilled off under reduced pressure, and methanol (300 mL) and a 10% aqueous sodium hydroxide solution (20 mL) were added to the resultant residue, followed by stirring at 5° C. to −15° C. for 1 hour. The mixture was neutralized with 10% hydrochloric acid, and then water (300 mL), THF (200 mL), and ethyl acetate (400 mL) were added to the mixture. An organic layer was washed with saturated brine two times and then dried with anhydrous sodium sulfate. The solvent was distilled off under reduced pressure to yield 112 g of trans-4-(3,5-difluorophenyl)cyclohexane carbaldehyde as a light yellow oil.

(11-7) Then, trans-4-(3,5-difluorophenyl)cyclohexane carbaldehyde (112 g) was dissolved in ethanol (224 mL), THF (30 mL), and water (30 mL), and sodium tetrahydroborate (9.4 g) was slowly added to the resultant solution at an outside temperature or 5° C., followed by stirring at an outside temperature of 5° C. for 10 minutes. The reaction solution was slowly poured into 10% hydrochloric acid (450 mL) and stirred for a white, and then an organic layer was separated. An aqueous layer was subjected to extraction with ethyl acetate, and the ethyl acetate extract was combined with the organic layer and washed with saturated brine two times. The mixture was dried with anhydrous sodium sulfate, and then the solvent was distilled off under reduced pressure to yield 110 g of trans-4-(3,5-difluorophenyl)cyclohexylmethanol as light yellow oil.

(11-8) In an argon atmosphere, 2,6-difluoro-4-propylphenol (70 g) produced in 11-1, trans-4-(3,5-difluorophenyl)cyclohexylmethanol (82.6 g) produced in 11-7, and triphenylphosphine (110 g) were dissolved in THF (400 mL), and DIAD (81.2 g) was added dropwise to the resultant solution at an inside temperature of 23° C. or less. After stirring at room temperature for 10 minutes, 10 mL of water was added to the mixture, and the solvent was distilled off under reduced pressure. Then, hexane (200 mL), water (200 mL), and methanol (300 mL) were added to the residue, and an organic layer was separated. An aqueous layer was subjected to extraction with hexane, and the hexane extract was combined with the organic layer and washed with a 50% aqueous methanol solution (200 mL) two times and saturated brine (200 mL) in that order. The resultant solution was purified by column chromatography (silica gel/hexane), and the solvent was distilled off under reduced pressure to produce 123.4 g of light yellow solid. The solid was recrystallized from ethanol (200 mL) to yield 80.2 g of 4-(3,5-difluorophenyl)cyclohexyl-(2,6-difluoro-4-propylphenyloxy)methane as a colorless solid.

(11-9) In an argon atmosphere, 4-(3,5-difluorophenyl)cyclohexyl-(2,6-difluoro-4-propylphenyloxy)methane (40 g) produced in 11-8 was dissolved in THF (400 mL), and a 1.6 mol/L n-butyllithium hexane solution (70 mL) was added dropwise to the resultant solution at an inside temperature of −50° C. to −60° C. The mixture was heated to −40° C. and then again cooled, and a solution of iodine (32 g) in THF (80 mL) was added dropwise at −50° C. or less. After the inside temperature was increased to 0° C., a 10% aqueous sodium sulfite solution (100 mL) was added dropwise, the mixture was stirred at room temperature for 1 hour, and an organic layer was separated. An aqueous layer was subjected to extraction with ethyl acetate, and the ethyl acetate extract was combined with the organic layer, washed with a 5% aqueous sodium sulfite solution and saturated brine two times, and then dried with anhydrous sodium sulfate. The solvent was distilled off under reduced pressure to yield 52.8 g of 4-(3,5-difluoro-4-iodophenyl)cyclohexyl-(2,6-difluoro-4-propylphenyloxy)methane as a light yellow solid.

(11-10) In an argon atmosphere, 4-(3,5-difluoro-4-iodophenyl)cyclohexyl-(2,6-difluoro-4-propylphenyloxy)methane (17.6 g) produced in 11-9, potassium carbonate (7.2 g), 5,5-dimethyl-2-(3,4,5-trifluorophenyl)-[1,3,2]dioxaborinane (13.6 g, produced by a method described in WO2003/105860), and tetrakis-tripheylphosphine palladium (1.6 g) were suspended in DMF (70 mL), followed by stirring at an inside temperature of 100° C. to 115° C. for 18 hours. Then, water (700 mL) and ethyl acetate (200 mL) were added to the resultant suspension at room temperature to separate an organic layer. An aqueous layer was subjected to extraction with hexane, and the hexane extract was combined with the organic layer, washed with saturated brine two times, and then dried with anhydrous sodium sulfate. The solvent was distilled off under reduced pressure, and the resultant residue was purified by silica gel column chromatography and then recrystallized from ethanol to yield 8.8 g of 4-[3,5-difluoro-4-(3,4,5-trifluorophenyl)phenyl]cyclohexyl-(2,6-difluoro-4-propylphenyloxy)methane as colorless crystals.

MS m/z: 510 [M$^+$]

Phase transition temperature (° C.): Cr 86 N 93.5 Iso $^1$HNMR (CDCl$_3$, TMS internal standard) δ (ppm)=7.11 (2H, t, J=7.6 Hz), 6.86 (2H, d, J=9.3 Hz), 6.71 (2H, d, J=9.2 Hz), 3.94 (2H, d, J=6.4 Hz), 2.57-2.49 (3H, m), 2.10-1.98 (4H, m), 1.89-1.81 (1H, m), 1.66-1.43 (4H, m), 1.31-1.21 (2H, m), 0.93 (3H, t, J=7.3 Hz)

Example 12

Production of 4-[3,5-difluoro-4-(4-trifluoromethoxyphenyl)phenyl]cyclohexyl-(2,6-difluoro-4-propylphenyloxy)methane (15-6)

[Chem. 47]

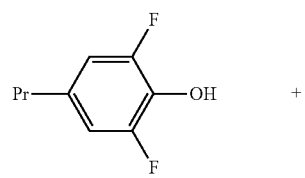

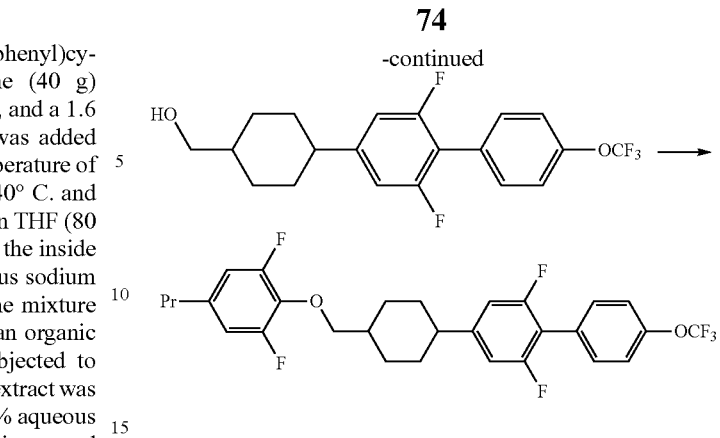

According to the same method as in Examples 1 to 11, 4-[3,5-difluoro-4-(4-trifluoromethoxyphenyl)phenyl]cyclohexyl-(2,6-difluoro-4-propylphenyloxy)methane was yielded.

MS m/z: 540 [M$^+$]

Phase transition temperature (° C.): Cr 80.5 N 151 Iso $^1$HNMR (CDCl$_3$, TMS internal standard) δ (ppm)=7.49 (2H, d, J=8.6 Hz), 7.29 (4H, d, J=8.0 Hz), 6.86 (2H, d, J=9.0 Hz), 6.71 (2H, d, J=9.0 Hz), 3.95 (2H, d, J=6.4 Hz), 2.58-2.49 (3H, m), 2.11-1.99 (4H, m), 1.87-1.82 (1H, m), 1.66-1.45 (4H, m), 1.32-1.21 (2H, m), 0.93 (3H, t, J=7.3 Hz)

Example 13

Production of 3,5-difluoro-4-(3,4,5-trifluorophenyl)phenyl-[2-fluoro-4-(4-propylcyclohexyl)phenyloxy]methane (13-4)

[Chem. 48]

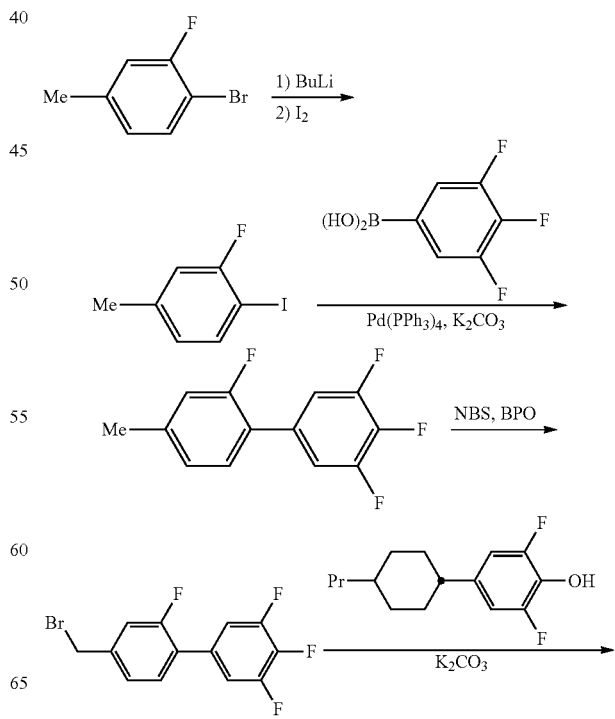

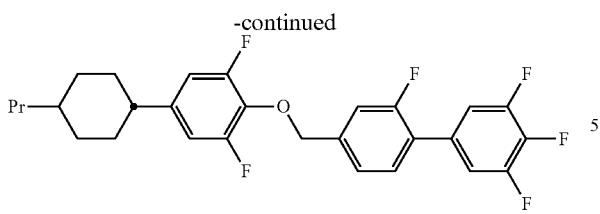

(13-1) Under dry nitrogen, a solution prepared by dissolving 4-bromo-3-fluorotoluene (10 g) in THF (50 mL) was cooled to −72° C. Then, a 1.6 mol/L n-butyl lithium hexane solution (35 mL) was added at −72° C. to the solution such a rate that the inside temperature was not more than −65° C., followed by further stirring at −72° C. for 1 hour. A solution prepared by dissolving iodine (14.8 g) in THF (30 mL) was added at −72° C. to the resultant mixture such a rate that the inside temperature was not more than −60° C., and the temperature was slowly increased to room temperature. Then, a saturated aqueous ammonium chloride solution and hexane were added at room temperature to separate an organic layer, and the organic layer was washed with a 10% aqueous sodium sulfite solution two times and saturated brine in that order, and then dried with sodium sulfate. The sodium sulfate was filtered off, and the organic solvent was distilled off under reduced pressure. The residue was purified by silica gel column chromatography to yield 13.0 g of 3-fluoro-4-iodotoluene as a yellow liquid.

(13-2) A solution prepared by suspending 3-fluoro-4-iodotoluene (12.0 g) produced in 13-1, 3,4,5-trifluorophenylboric acid (9.0 g), anhydrous potassium carbonate (4.1 g), and tetrakis-triphenylphosphine palladium(0) (0.33 g) in ethanol (60 mL) was heated to 100° C. (2.5 MPa) in an autoclave and then stirred for 17 hours. After the solution was allowed to cool to room temperature, toluene and water were added to separate an organic layer. The organic layer was washed with saturated brine and then dried with sodium sulfate. The sodium sulfate was filtered off, and the organic solvent was distilled off under reduced pressure. Then, the residue was purified by silica gel column chromatography to yield 9.5 g of 4-(3,4,5-trifluorophenyl)-3-fluorotoluene as a colorless solid.

(13-3) Under dry nitrogen, 4-(3,4,5-trifluorophenyl)-3-fluorotoluene (8.4 g) produced in 13-2, N-bromosuccinimide (6.2 g), and benzoyl peroxide (5 mg) were suspended in carbon tetrachloride (90 mL), followed by stirring under reflux for 6 hours. After the suspension was allowed to cool to room temperature, water was added to the suspension to separate an organic layer. The organic layer was washed with water and then dried by adding sodium sulfate. The organic solvent was distilled off under reduced pressure, and the residue was purified by silica gel column chromatography to yield 9.5 g of 4-(3,4,5-trifluorophenyl)-3-fluorobenzyl bromide as a yellow liquid.

(13-4) Under dry nitrogen, a solution prepared by suspending 1-(trans-4-propylcyclohexyl)-3,5-difluorophenol (5.2 g) produced in the step 3-3, 4-(3,4,5-trifluorophenyl)-3-fluorobenzyl bromide (9.5 g) produced in 13-3, and anhydrous potassium sulfate (5.6 g) in DMF (20 mL) was stirred at 70° C. for 6 hours. After, the suspension was allowed to cool to room temperature, water and toluene were added to the suspension to separate an organic layer. The organic layer was washed with saturated brine, and then dried by adding sodium sulfate. The sodium sulfate was filtered off, and the organic solvent was distilled off under reduced pressure. The residue was purified by silica gel column chromatography and then recrystallized from ethanol to yield 2.1 g of 3,5-difluoro-4-(3,4,5-trifluorophenyl)phenyl-[2,6-difluoro-4-(4-propylcyclohexyl)phenyloxy]methane as a white solid.

MS m/z: 492 [M⁺]

Phase transition temperature (° C.): Cr 70 Iso

¹HNMR (CDCl₃, TMS internal standard) δ (ppm)=7.29-7.25 (1H, m), 7.15-7.08 (4H, m), 7.01-6.98 (2H, m), 5.11 (2H, s), 2.53-2.45 (1H, m), 1.93-1.86 (4H, m), 1.48-1.27 (5H, m), 1.25-1.19 (2H, m), 1.11-1.00 (2H, m), 0.91 (3H, t, J=7.6 Hz)

Example 14

Production of (3,4,5-trifluorophenyl)-[2,6-difluoro-4-(4-(4-propylcyclohexyl)cyclohexyl)phenyloxy]methane (8-1)

[Chem. 49]

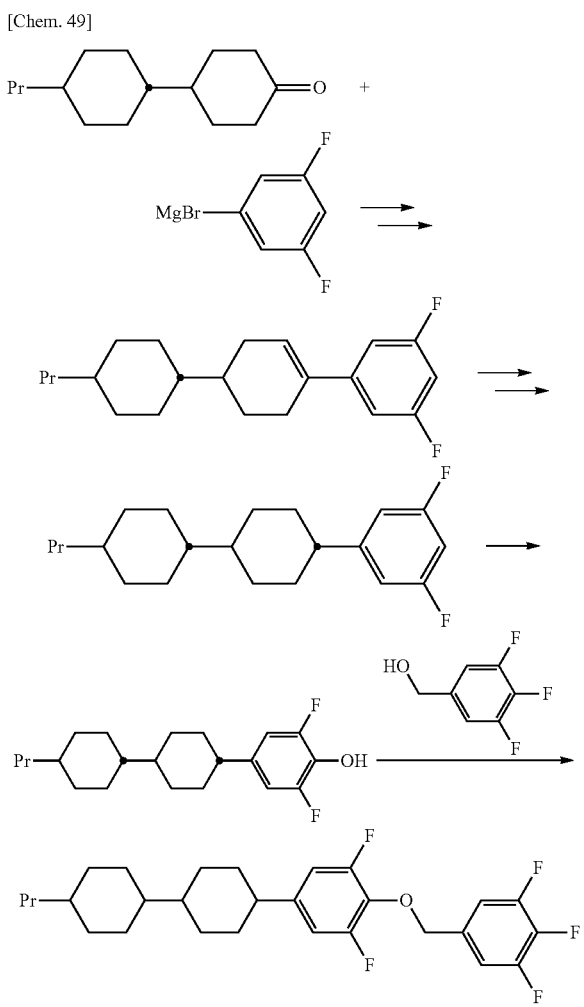

According to the same method as in Examples 1 to 8, (3,4,5-trifluorophenyl)-[2,6-difluoro-4-(4-(4-propylcyclohexyl)cyclohexyl)phenyloxy]methane was yielded.

MS m/z: 480 [M⁺]

Phase transition temperature (° C.): Cr 85.8 N 170.0 Iso

¹HNMR (CDCl₃, TMS internal standard) δ (ppm)=δ (ppm) =7.10 (2H, d, J=6.8 Hz), 7.08 (2H, d, J=6.8 Hz), 6.75 (2H, d, J=9.6 Hz), 5.03 (2H, s), 2.38-2.32 (1H, m), 1.89-1.71 (8H, m), 1.33-1.28 (4H, m), 1.16-0.94 (9H, m), 0.89-0.83 (5H, m)

Example 15

Production of (4-fluorophenyl)-[2,6-difluoro-4-(4-(4-propylcyclohexyl)cyclohexyl)phenyloxy]methane (8-3)

[Chem. 50]

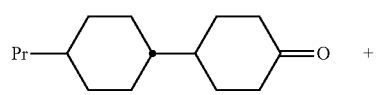

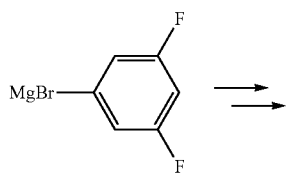

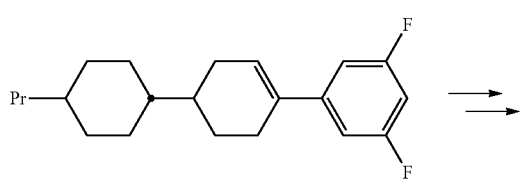

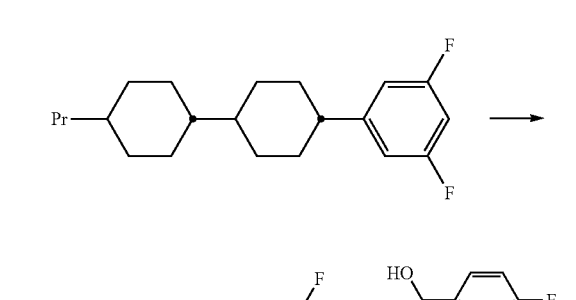

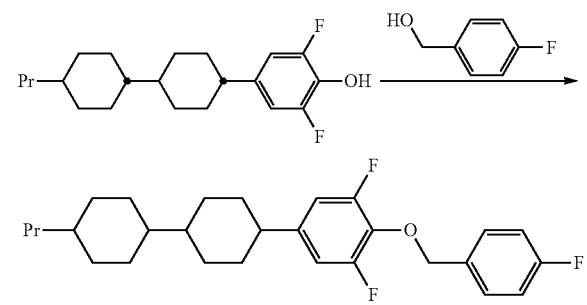

According to the same method as in Examples 1 to 8, (4-fluorophenyl)-[2,6-difluoro-4-(4-(4-propylcyclohexyl)cyclohexyl)phenyloxy]methane was yielded.

MS m/z: 444 [M$^+$]

Phase transition temperature (° C.): Cr 83.0 N 197.8 Iso $^1$HNMR (CDCl$_3$, TMS internal standard) δ (ppm)=7.44-7.40 (2H, m), 7.04 (2H, t, J=8.7 Hz), 6.72 (2H, d, J=9.6 Hz), 5.07 (2H, s), 2.38-2.32 (1H, m), 1.89-1.71 (8H, m), 1.33-1.28 (4H, m), 1.16-0.94 (9H, m), 0.89-0.81 (5H, m)

Example 16

Production of (4-trifluoromethoxyfluorophenyl)-[2,6-difluoro-4-(4-(4-propylcyclohexyl)cyclohexyl)phenyloxy]methane (8-9)

[Chem. 51]

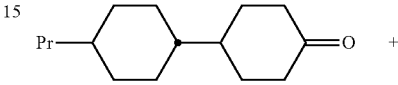

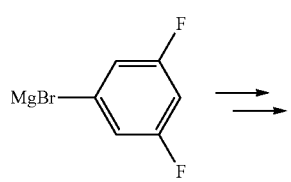

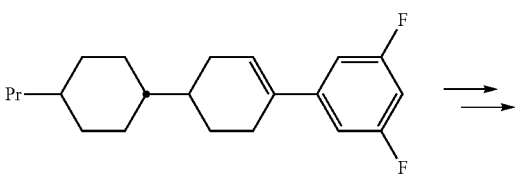

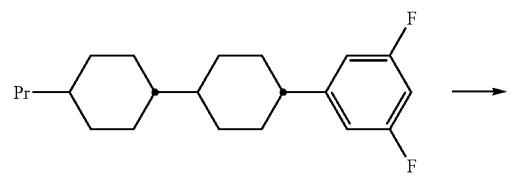

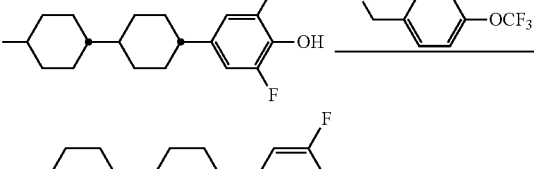

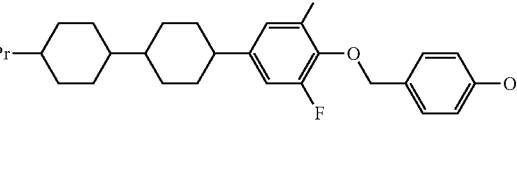

According to the same method as in Examples 1 to 8, (4-trifluoromethoxyfluorophenyl)-[2,6-difluoro-4-(4-(4-propylcyclohexyl)cyclohexyl)phenyloxy]methane was yielded.

MS m/z: 510 [M$^+$]

Phase transition temperature (° C.): Cr 68.5 S 91.3 N 190.3 Iso $^1$HNMR (CDCl$_3$, TMS internal standard) δ (ppm)=7.49 (2H, d, J=8.5 Hz), 7.22 (2H, d, J=8.1 Hz), 6.73 (2H, d, J=9.6

Hz), 5.10 (2H, s), 2.39-2.33 (1H, m), 1.89-1.71 (8H, m), 1.33-1.26 (4H, m), 1.16-0.81 (14H, m)

Example 17

Production of (4-trifluorophenyl)-[2,6-difluoro-4-(4-vinylcyclohexyl)phenyloxy]methane (2-1)

[Chem. 52]

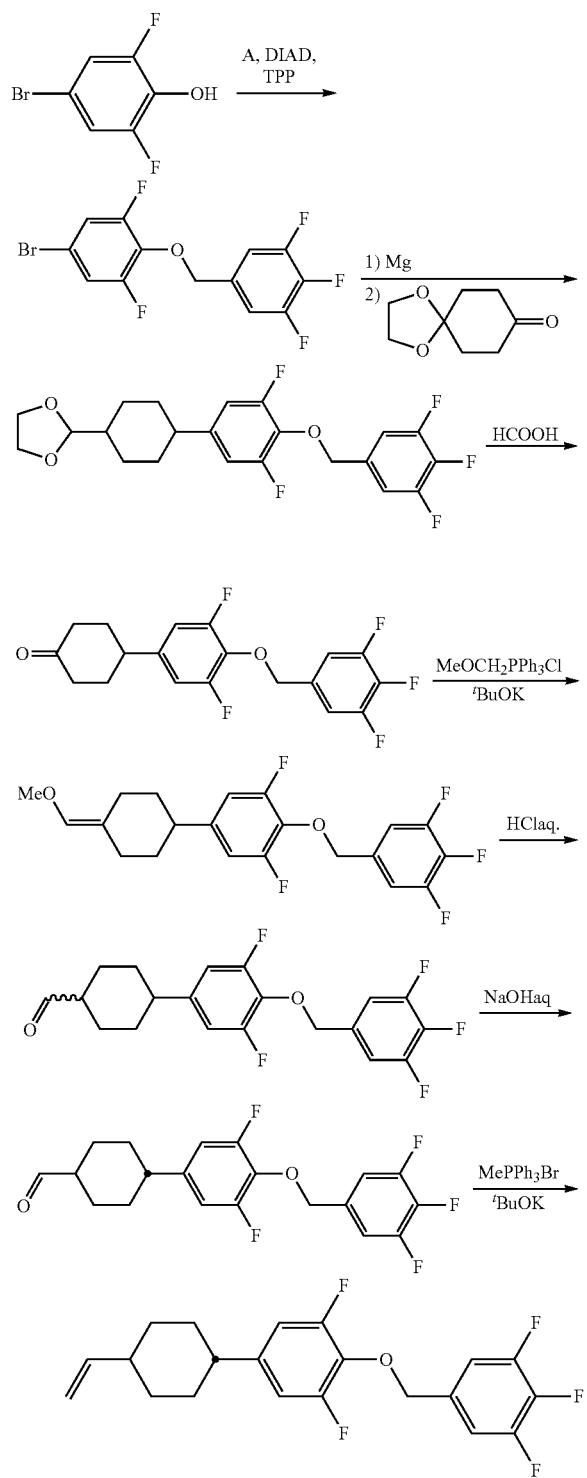

According to the same method as in Examples 1 to 11, 4-trifluorophenyl)-[2,6-difluoro-4-(4-vinylcyclohexyl)phenyloxy]methane was yielded.

MS m/z: 382 [M$^+$]

$^1$HNMR (CDCl$_3$, TMS internal standard) δ (ppm)=7.08 (2H, d, J=6.8 Hz), 6.75 (2H, d, J=9.6 Hz), 5.81-5.78 (1H, m), 5.02 (2H, s), 5.00-4.97 (2H, m), 2.41-2.35 (1H, m), 2.13-2.11 (1H, m), 1.87-1.83 (4H, m), 1.39-1.17 (4H, m)

Example 18

Production of 5-propyl-2-[4-(3,4,5-trifluorophenylmethyloxy)-3,5-difluorophenyl]tetrahydropyran (16-1)

[Chem. 53]

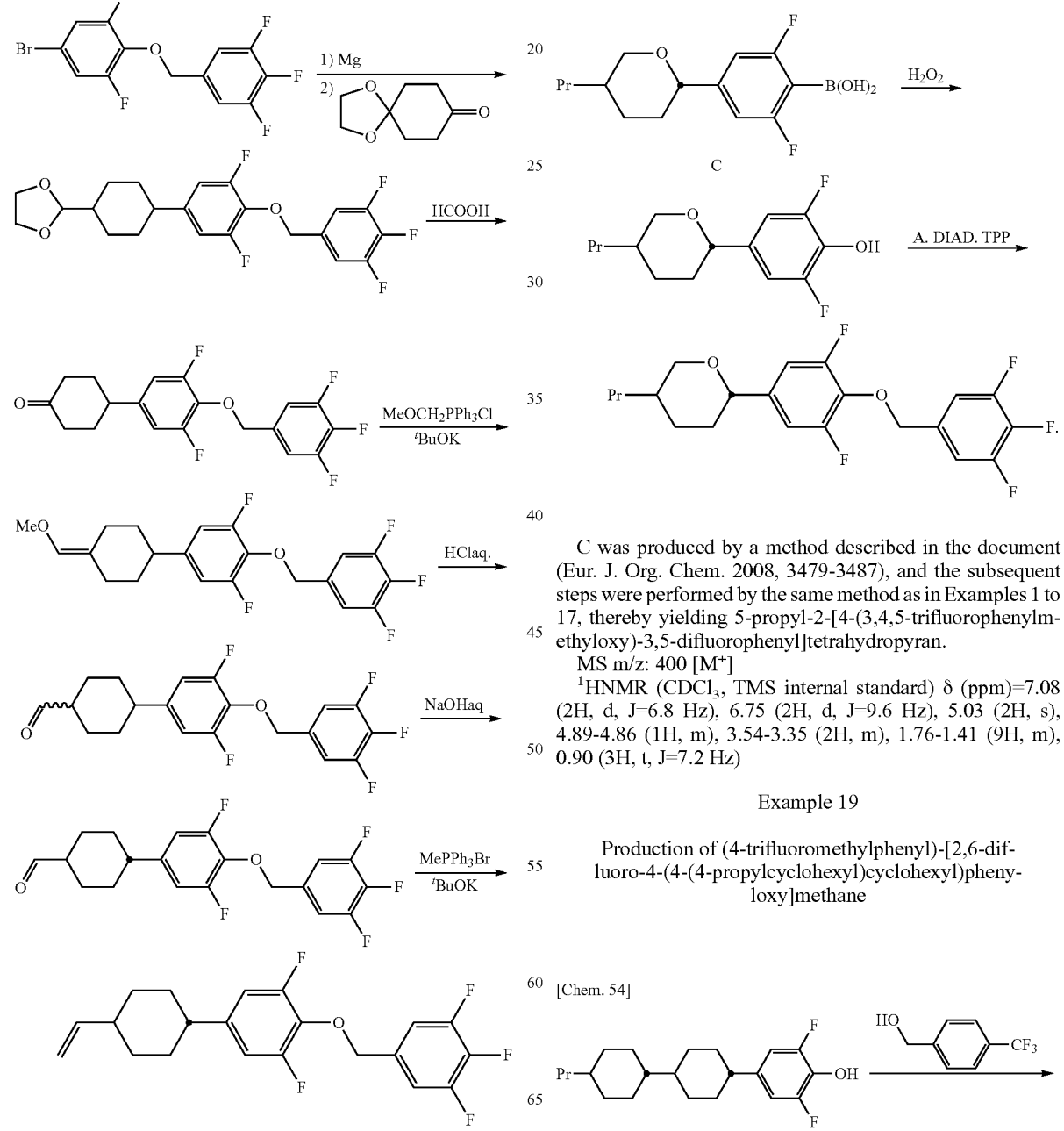

C was produced by a method described in the document (Eur. J. Org. Chem. 2008, 3479-3487), and the subsequent steps were performed by the same method as in Examples 1 to 17, thereby yielding 5-propyl-2-[4-(3,4,5-trifluorophenylmethyloxy)-3,5-difluorophenyl]tetrahydropyran.

MS m/z: 400 [M$^+$]

$^1$HNMR (CDCl$_3$, TMS internal standard) δ (ppm)=7.08 (2H, d, J=6.8 Hz), 6.75 (2H, d, J=9.6 Hz), 5.03 (2H, s), 4.89-4.86 (1H, m), 3.54-3.35 (2H, m), 1.76-1.41 (9H, m), 0.90 (3H, t, J=7.2 Hz)

Example 19

Production of (4-trifluoromethylphenyl)-[2,6-difluoro-4-(4-(4-propylcyclohexyl)cyclohexyl)phenyloxy]methane

[Chem. 54]

-continued

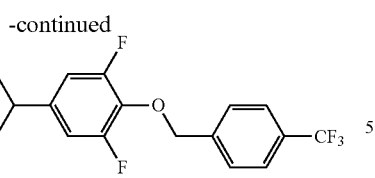

According to the same method as in Examples 1 to 11, (4-trifluoromethylphenyl)-[2,6-difluoro-4-(4-(4-propylcyclohexyl)cyclohexyl)phenyloxy]methane was yielded.

MS m/z: 494 [M$^+$]

Phase transition temperature (° C.): Cr 112 N 174 Iso $^1$HNMR (CDCl$_3$, TMS internal standard) δ (ppm)=7.35 (2H, d, J=8.2 Hz), 7.49 (2H, d, J=8.5 Hz), 6.73 (2H, d, J=9.6 Hz), 5.10 (2H, s), 2.39-2.33 (1H, m), 1.89-1.71 (8H, m), 1.33-1.26 (4H, m), 1.16-0.81 (14H, m)

Example 20

Production of (3,4,5-trifluorophenyl)-[2,6-difluoro-4-(2-fluoro-4-(4-propylphenyl)phenyl)phenyloxy]methane (5-1)

[Chem. 55]

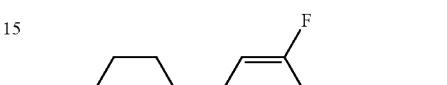

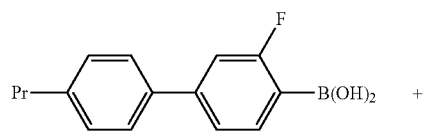

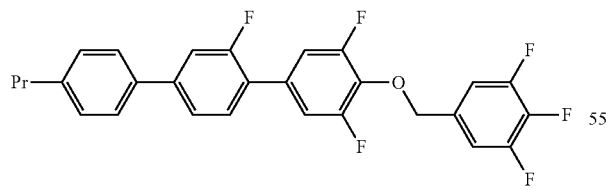

According to the same method as in Examples 1 to 11, (3,4,5-trifluorophenyl)-[2,6-difluoro-4-(2-fluoro-4-(4-propylphenyl)phenyl)phenyloxy]methane was yielded.

MS m/z: 486 [M$^+$]

Phase transition temperature (° C.): Cr 111.5 N 137.8 Iso $^1$HNMR (CDCl$_3$, TMS internal standard) δ (ppm)=7.52 (2H, d, J=8.4 Hz), 7.46-7.36 (3H, m), 7.28 (2H, d, J=8.0 Hz), 7.21-7.10 (4H, m), 5.13 (2H, s), 2.64 (1H, t, J=7.6 Hz), 1.73-1.64 (2H, m), 0.98 (3H, t, J=7.2 Hz)

Example 21

Production of 3,5-difluoro-4-(3,4-difluorophenyl)phenyl-[2,6-difluoro-4-(4-propylcyclohexyl)phenyloxy]methane (13-2)

[Chem. 56]

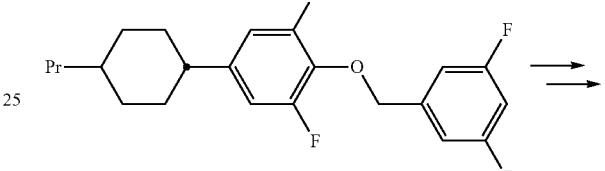

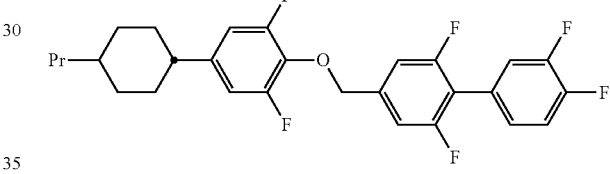

According to the same method as in Examples 1 to 11, 3,5-difluoro-4-(3,4-difluorophenyl)phenyl-[2,6-difluoro-4-(4-propylcyclohexyl)phenyloxy]methane was yielded.

MS m/z: 492 [M$^+$]

Phase transition temperature (° C.): Cr 87.6 N 97.8 Iso $^1$HNMR (CDCl$_3$, TMS internal standard) δ (ppm)=7.32-7.26 (1H, m), 7.26 (1H, dd, J1=9.1 Hz, J2=2.6 Hz), 7.21-7.18 (1H, m), 7.12 (2H, d, J=8.0 Hz), 6.76 (2H, d, J=9.7 Hz), 5.11 (2H, s), 2.42-2.36 (1H, m), 1.87-1.84 (4H, m), 1.40-1.17 (7H, m), 1.07-0.97 (2H, m), 0.90 (3H, t, J=7.2 Hz)

Example 22

Production of 4-[3,5-difluoro-4-(3,4-difluorophenyl)phenyl]cyclohexyl-(2,6-difluoro-4-propylphenyloxy)methane (15-7)

[Chem. 57]

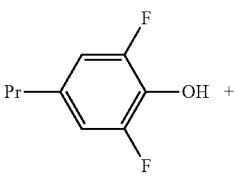

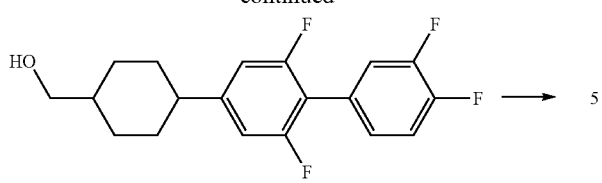

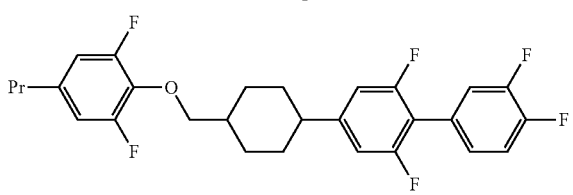

According to the same method as in Examples 1 to 11, 4-[3,5-difluoro-4-(3,4-difluorophenyl)phenyl]cyclohexyl-(2,6-difluoro-4-propylphenyloxy)methane was yielded.

MS m/z: 492 [M$^+$]

Phase transition temperature (° C.): Cr 69.5 N 111.5 Iso $^1$HNMR (CDCl$_3$, TMS internal standard) δ (ppm)=7.32-7.17 (3H, m), 6.86 (2H, d, J=9.0 Hz), 6.71 (2H, d, J=9.1 Hz), 3.95 (2H, d, J=6.1 Hz), 2.58-2.49 (3H, m), 2.17-2.01 (4H, m), 1.98-1.80 (1H, m), 1.66-1.31 (10H, m), 1.28-1.22 (2H, m), 0.91 (3H, t, J=7.2 Hz)

Example 23

Production of (3,4-difluorophenyl)-[2,6-difluoro-4-(trans-4-propylcyclohexyl)phenyloxy]methane (2-2)

[Chem. 58]

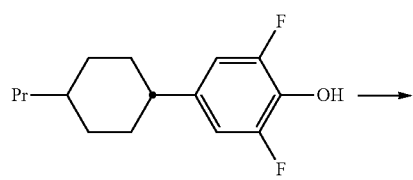

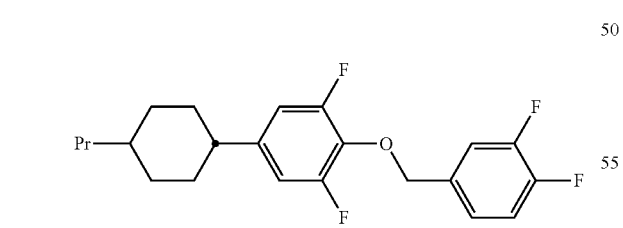

According to the same method as in Examples 1 to 11, 3,4-difluorophenyl)-[2,6-difluoro-4-(trans-4-propylcyclohexyl)phenyloxy]methane was yielded.

MS m/z: 380 [M$^+$]

Phase transition temperature (° C.): Cr 46 Iso $^1$HNMR (CDCl$_3$, TMS internal standard) δ (ppm)=7.33-7.27 (1H, m), 7.18-7.10 (2H, m), 6.73 (2H, d, J=9.8 Hz), 5.05 (2H, s), 2.41-2.35 (1H, m), 1.85 (4H, d, J=12.3 Hz), 1.38-1.24 (5H, m), 1.22-1.16 (2H, m), 1.06-0.96 (2H, m), 0.89 (3H, t, J=7.1 Hz)

Example 24

Production of (4-trifluoromethoxyphenyl)-(2,6-difluoro-4-propylphenyloxy)methane (1-45)

[Chem. 59]

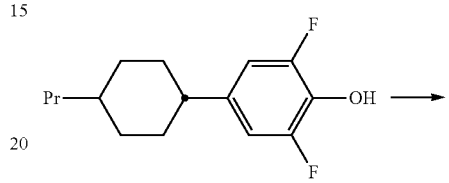

According to the same method as in Examples 1 to 11, (4-trifluoromethoxyphenyl)-(2,6-difluoro-4-propylphenyloxy)methane was yielded.

MS m/z: 346 [M$^+$]

Phase transition temperature (° C.): isotropic liquid at room temperature $^1$HNMR (CDCl$_3$, TMS internal standard) δ (ppm)=7.49 (2H, d, J=8.5 Hz), 7.21 (2H, d, J=8.5 Hz), 6.70 (2H, d, J=8.9 Hz), 5.10 (2H, s), 2.50 (2H, d, J=7.4 Hz), 1.59 (2H, quintet, J=7.6 Hz), 0.92 (3H, t, J=7.4 Hz)

Comparative Example 1

Production of (3,4,5-trifluorophenyloxy)-[2,6-difluoro-4-(4-propylphenyl)phenyl]methane

[Chem. 60]

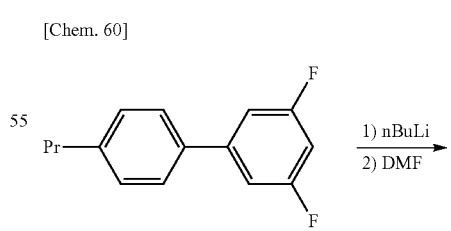

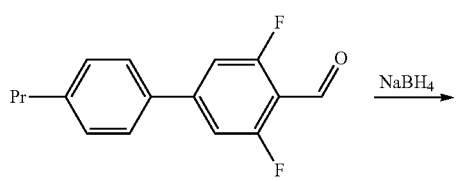

-continued

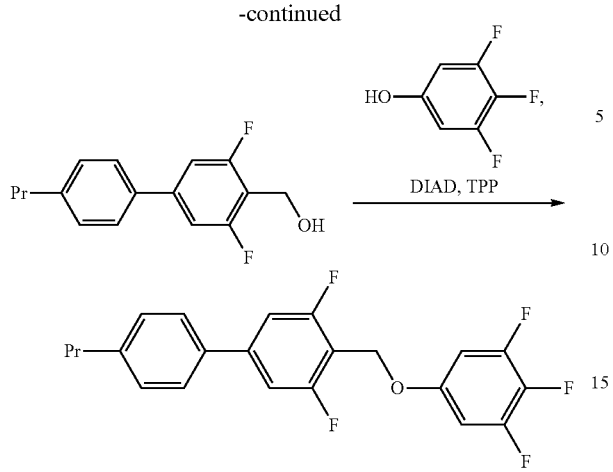

(1-1) In a nitrogen atmosphere, 50.00 g of 3,5-difluoro-1-(4-propylphenyl)benzene produced in an intermediate step of Example 1 was dissolved in 300 mL of THF, and the resultant solution was cooled to −40° C. Then, 150 mL of butyl lithium (1.6 mol/L, hexane solution) was added at such a rate that the inside temperature did not exceed −35° C., followed by stirring at −40° C. for 1 hour. Then, 21 g of DMF was added at −40° C. at such a rate that the inside temperature did not exceed −35° C., and the mixture was stirred at room temperature for 2 hours. Then, 10% hydrochloric acid was added until the reaction system became acidic to separate an organic layer. An aqueous layer was subjected to extraction with toluene, and the toluene extract was combined with the organic layer. The resultant mixture was washed with saturated aqueous sodium bicarbonate and saturated brine and dried by adding sodium sulfate. The solvent was distilled off under reduced pressure to yield 50.01 g of 2,6-difluoro-4-(4-propylphenyl)benzaldehyde.

(1-2) Then, 50.01 g of 2,6-difluoro-4-(4-propylphenyl)benzaldehyde and 7 mL g of water were dissolved in 35 mL of ethanol, the resultant solution was cooled with ice, and 2.18 g of sodium tetrahydroborate was slowly added to the solution. After stirring at room temperature for 2 hours, 10% hydrochloric acid was added until the reaction system became acidic, followed by stirring for 1 hour. Then, toluene was added to separate an organic layer, an aqueous layer was subjected to extraction with toluene, and the toluene extract was combined with the organic layer. The resultant mixture was washed with saturated brine and dried by adding sodium sulfate. Then, the solvent was distilled off under reduced pressure, and the residue was recrystallized from ethanol to yield 48.02 g of 2,6-difluoro-4-(4-propylphenyl)benzyl alcohol.

(1-3) In a nitrogen atmosphere, 10.00 g of 2,6-difluoro-4-(4-propylphenyl)benzyl alcohol, 5.65 g of 3,4,5-trifluorophenol, and 13.01 g of triphenylphosphine were dissolved in 30 mL of THF, the resultant solution was cooled to −20° C., and 8.48 g of DIAD was added dropwise at such a rate that the inside temperature did not exceed −10° C. After stirring at room temperature for 1 hour, the solvent was distilled off under reduced pressure. Then, the residue was suspended by adding hexane, and precipitated triphenylphosphine was filtered off. An organic layer was washed with saturated brine and dried by adding sodium sulfate, and the solvent was distilled off under reduced pressure. The residue was purified by silica gel column chromatography and then recrystallized from ethanol to yield 11.32 g of (3,4,5-trifluorophenyloxy)-[2,6-difluoro-4-(4-propylphenyl)phenyl]methane.

Phase transition temperature (° C.): Cr 92.4 Iso

MS m/z: 392 [M+]

$^1$HNMR (CDCl$_3$, TMS internal standard) δ (ppm)=7.47 (2H, d, J=8.4 Hz), 7.27 (2H, d, J=8.0 Hz), 7.17 (2H, d, 8.8 Hz), 6.68-6.60 (2H, m), 5.07 (2H, s), 2.64 (2H, t, J=7.6 Hz), 1.67 (2H, dt, J1=8.0 Hz, J2=7.6 Hz), 0.968 (3H, t, J=7.2 Hz)

Comparative Example 2

Production of (3,4,5-trifluorophenyl)-[4-(4-propylphenyl)phenyloxy]methane

[Chem. 61]

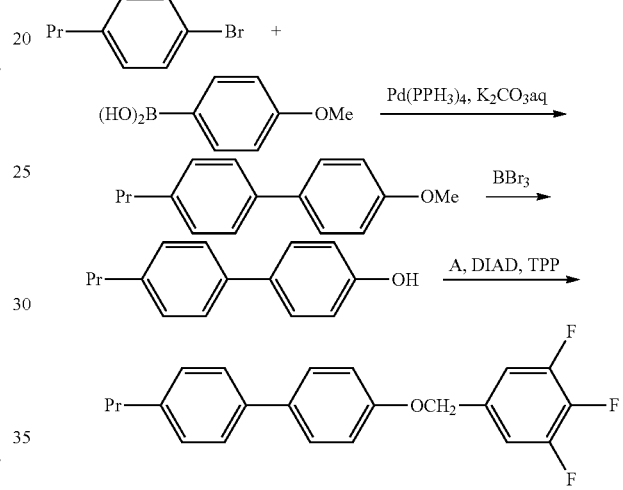

(2-1) In a nitrogen atmosphere, 20.00 g of 4-propylbromobenzene, 0.58 g of tetrakis-triphenylphosphine palladium, and 55 mL of an aqueous potassium carbonate solution (2 mol/L) were dissolved in 100 mL of ethanol, and the resultant solution was heated to 60° C. Then, a solution prepared by suspending 15.27 g of 4-methoxyphenylboronic acid in 60 mL of ethanol was added dropwise to the solution. After stirring at 60° C. for 2 hours, the mixture was allowed to cool to room temperature, and toluene was added to separate the mixture into layers. An aqueous layer was subjected to extraction with toluene, and the toluene extract was combined with an organic layer. The resultant mixture was washed with saturated brine and dried by adding sodium sulfate, and the solvent was distilled off under reduced pressure. The residue was purified by silica gel column chromatography and recrystallized from ethanol to yield 21.60 g of 4-(4-propylphenyl)anisole.

(2-2) Then, 21.60 g of 4-(4-propylphenyl)anisole was dissolved in 45 mL of dichloromethane, and the resultant solution was cooled with ice. Then, 35.79 g of boron tribromide was added to the solution at such a rate that the inside temperature did not exceed 10° C., followed by stirring at room temperature for 1 hour. Water was added to separate the mixture into layers, and an organic layer was washed with a saturated aqueous sodium bicarbonate solution and saturated brine and dried by adding sodium sulfate. Then, the solvent was distilled off under reduced pressure, and the residue was recrystallized from ethanol to yield 15.91 g of 4-(4-propylphenyl)phenol.

(2-3) In a nitrogen atmosphere, 12.15 g of 3,4,5-trifluorobenzyl alcohol (A) produced in (1-2), 15.91 g of 4-(4-propylphenyl)phenol, and 25.53 g of triphenylphosphine were dissolved in 50 mL of THF, and the resultant solution was cooled to −20° C. Then, 16.67 g of DIAD was added under cooling at such a rate that the inside temperature did not exceed −10° C., followed by stirring at room temperature for 1 hour. The solvent was distilled off under reduced pressure, a suspension was prepared by adding hexane, and precipitated triphenylphosphine oxide was removed by filtration. An organic layer was washed with saturated brine and dried by adding sodium sulfate. The solvent was distilled off under reduced pressure, and the residue was purified by silica gel column chromatography and recrystallized from ethanol to yield 22.52 g of (3,4,5-trifluorophenyl)-[4-(4-propylphenyl)phenyloxy]methane.

MS m/z: 356 [M+]

Phase transition temperature (° C.): Cr (SmA 93) 109 Iso $^1$HNMR (CDCl$_3$, TMS internal standard) δ=7.52 (2H, d, J=8.4 Hz), 7.46 (2H, d, J=8.4 Hz), 7.23 (2H, d, J=8.0 Hz), 7.08 (2H, dd, J1=7.2 Hz, J2=8.0 Hz), 6.99 (2H, d, J=8.8 Hz), 5.02 (2H, s), 2.62 (2H, t, J=8.0 Hz), 1.67 (2H, dt, J1=7.6 Hz, J2=8.0 Hz), 0.97 (3H, t, J=7.6 Hz)

Comparative Example 3

Production of (3,4,5-trifluorophenyl)-[4-(trans-4-propylcyclohexyl)phenyloxy]methane

[Chem. 62]

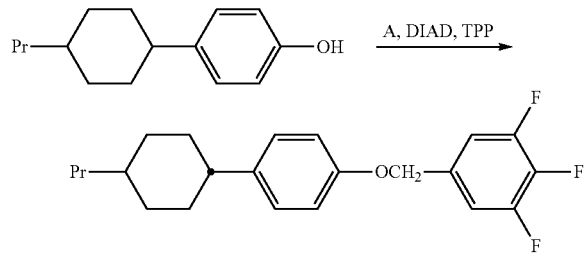

(3-1) According to the same method as in Comparative Example 2 except that trans-4-(4-propylcyclohexyl)phenol was used in place of 4-(4-propylphenyl)phenol used in Comparative Example 2, 35.50 g of (3,4,5-trifluorophenyl)-[4-(trans-4-propylcyclohexyl)phenyloxy]methane was yielded.

MS m/z: 362 [M+]

Phase transition temperature (° C.): Cr 71.5 Iso $^1$HNMR (CDCl$_3$, TMS internal standard) δ=7.13 (2H, d, J=8.8 Hz), 7.05 (2H, dd, J1=8.8 Hz, J2=8.8 Hz), 6.86 (2H, d, J=8.8 Hz), 4.96 (2H, s), 2.45-2.39 (1H, m), 1.87-1.84 (4H, m), 1.46-1.17 (7H, m), 1.08-0.99 (2H, m), 0.90 (3H, t, J=7.2 Hz)

Example 25

Preparation-1 of Liquid Crystal Composition

A host liquid crystal composition (H) having a composition below was prepared.

[Chem. 63]

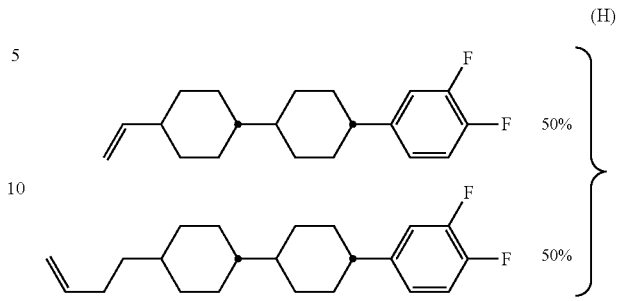

Here, physical property values of (H) are as follows.
Nematic phase upper limit temperature (T$_{n-i}$): 117.2° C.
Dielectric anisotropy (Δ∈): 4.38
Refractive index anisotropy (Δn): 0.0899
Viscosity (η$_{20}$): 20.3 mPa·s A liquid crystal composition (M-A) including 90% of the host liquid crystal (H) and 10% of (3,4,5-trifluorophenyl)-[2,6-difluoro-4-(4-propylphenyl)phenyloxy]methane (1-1) produced in Example 1 was prepared. Physical property values of the composition are as follows.
T$_{n-i}$: 102.6° C.
Δ∈: 5.99
Δn: 0.0912
η$_{20}$: 20.2 mPa·s The prepared liquid crystal composition (M-A) maintained a uniform nematic liquid crystal state at room temperature for one month or more.

Example 26

Preparation-2 of Liquid Crystal Composition

A liquid crystal composition (M-B) including 90% of the host liquid crystal (H) and 10% of (3,4-difluorophenyl)-[2,6-difluoro-4-(4-propylphenyl)phenyloxy]methane yielded in Example 2 was prepared. Physical property values of the composition are as follows.
T$_{n-i}$: 100.2° C.
Δ∈: 5.14
Δn: 0.0902
η$_{20}$: 20.1 mPa·s The prepared liquid crystal composition (M-B) maintained a uniform nematic liquid crystal state at room temperature for one month or more.

Example 27

Preparation-3 of Liquid Crystal Composition

A liquid crystal composition (M-C) including 90% of the host liquid crystal (H) and 10% of (3,4,5-trifluorophenyl)-[2,6-difluoro-4-(trans-4-propylcyclohexyl)phenyloxy]methane yielded in Example 3 was prepared. Physical property values of the composition are as follows.
T$_{n-i}$: 104.1° C.
Δ∈: 5.59
Δn: 0.0833
η$_{20}$: 19.4 mPa·s The prepared liquid crystal composition (M-C) maintained a uniform nematic liquid crystal state at room temperature for one month or more.

Example 28

Preparation-4 of liquid crystal composition

A liquid crystal composition (M-D) including 90% of the host liquid crystal (H) and 10% of (3,4-5-trifluorophenyl)-[2,6-difluoro-4-[4-(trans-4-propylcyclohexyl)phenyl]phenyloxy]methane produced in Example 4 was prepared. Physical property values of the composition are as follows.
$T_{n-i}$: 118.4° C.
$\Delta\in$: 5.60
$\Delta n$: 0.0959
$\eta_{20}$: 22.1 mPa·s The prepared liquid crystal composition (M-D) maintained a uniform nematic liquid crystal state at room temperature for one month or more.

Example 29

Preparation-5 of liquid crystal composition

A liquid crystal composition (M-E) including 90% of the host liquid crystal (H) and 10% of (3,4-difluorophenyl)-[2,6-difluoro-4-[4-(trans-4-propylcyclohexyl)phenyl]phenyloxy]methane yielded in Example 5 was prepared. Physical property values of the composition are as follows.
$T_{n-i}$: 151.2° C.
$\Delta\in$: 9.10
$\Delta n$: 0.0883
$\eta_{20}$: 21.9 mPa·s The prepared liquid crystal composition (M-E) maintained a uniform nematic liquid crystal state at room temperature for one month or more.

Comparative Example 4

Preparation-6 of Liquid Crystal Composition

A liquid crystal composition (M-F) including 90% of the host liquid crystal (H) and 10% of (3,4,5-trifluorophenyloxy)-[2,6-difluoro-4-(4-propylphenyl)phenyl]methane yielded in Comparative Example 1 was prepared. Physical property values of the composition are as follows.
$T_{n-i}$: 98.2° C.
$\Delta\in$: 6.12
$\Delta n$: 0.0908
$\eta_{20}$: 23.9 mPa·s The prepared liquid crystal composition (M-F) maintained a uniform nematic liquid crystal state at room temperature for one month or more.

Comparative Example 5

Preparation-7 of Liquid Crystal Composition

A liquid crystal composition (M-G) including 90% of the host liquid crystal (H) and 10% of (3,4,5-trifluorophenyl)-[4-(4-propylphenyl)phenyloxy]methane yielded in Comparative Example 2 was prepared. Physical property values of the composition are as follows.
$T_{n-i}$: 105.6° C.
$\Delta\in$: 4.72
$\Delta n$: 0.0963
$\eta_{20}$: 21.9 mPa·s The prepared liquid crystal composition (M-G) caused crystal precipitation at room temperature one day after.

Comparative Example 6

Preparation-8 of Liquid Crystal Composition

A liquid crystal composition (M-H) including 90% of the host liquid crystal (H) and 10% of (3,4,5-trifluorophenyl)-[4-(trans-4-propylcyclohexyl)phenyloxy]methane yielded in Comparative Example 2 was prepared. Physical property values of the composition are as follows.
$T_{n-i}$: 105.7° C.
$\Delta\in$: 4.62
$\Delta n$: 0.0878
$\eta_{20}$: 21.1 mPa·s The prepared liquid crystal composition (M-H) caused crystal precipitation at room temperature two weeks after.

Comparison between Example 8 and Comparative Example 4 revealed that the physical property values can be significantly improved according to the direction of an ether bond, and it was found that the compound of the present invention is little decreased in $T_{n-i}$ and exhibits very low $\eta_{20}$ while maintaining relatively large $\Delta\in$. On the other hand, comparison between Example 8 and Comparative Example 5 and comparison between Example 10 and Comparative Example 6 revealed that the physical property values can be significantly improved even by introducing fluorine, and it was found that the compounds of the present invention are little decreased in $T_{n-i}$, exhibit very low $\eta_{20}$, and significantly improved in solubility in a liquid crystal composition. Since Examples 10 to 12 also show relatively large $\Delta\in$, relatively high $T_{n-i}$, low $\eta_{20}$, and high solubility in a liquid crystal composition, and thus it was found that the compounds of the present invention having a 2-fluorophenyloxymethane structure show specifically excellent physical property values.

Example 30

Preparation-6 of Liquid Crystal Composition

A liquid crystal composition was prepared by the same method as in Example 25 using each of the compounds yielded in Examples 8 to 16 and 18, and physical property values thereof were measured. An extrapolation value at 100% of each of the compounds of the present invention was determined from the measured values, and the obtained values are shown in a table below.

TABLE 1

| Compound | $\Delta\epsilon$ | $\Delta n$ | $T_{n-1}$ | $\eta_{20}$ | Solubility |
|---|---|---|---|---|---|
| (1-1) | 20.0 | 0.103 | −27.8 | 19.3 | Very good |
| (1-2) | 10.3 | 0.052 | −1.2 | 19.3 | Very good |
| (2-1) | 14.5 | 0.059 | −23.8 | 13.4 | Very good |
| (6-1) | 16.6 | 0.150 | 129.2 | 38.1 | Very good |
| (6-2) | 9.10 | 0.074 | 151.2 | 36.6 | Very good |
| (1-4) | 12.1 | 0.121 | −5.1 | 29.2 | Good |
| (9-10) | 14.7 | 0.099 | 104.2 | 32.5 | Fair |
| (1-9) | 11.0 | 0.139 | 8.2 | 8.8 | Very good |
| (7-19) | 28.1 | 0.111 | 81.7 | 44.2 | Good |
| (13-1) | 27.2 | 0.116 | 63.2 | 44.1 | Fair |
| (15-5) | 35.5 | 0.104 | 75.2 | 56.9 | Very good |
| (15-6) | 20.4 | 0.127 | 122.2 | 46.0 | Very good |
| (13-4) | 13.8 | 0.042 | −78.8 | 80.0 | Very good |
| (8-1) | 13.3 | 0.067 | 145.2 | 29.5 | Very good |
| (8-3) | 6.0 | 0.092 | 188.2 | 38.0 | Very good |
| (8-9) | 7.2 | 0.108 | 176.2 | 25.1 | Very good |
| (16-1) | 18.6 | 0.052 | −32.3 | 12.3 | Very good |

INDUSTRIAL APPLICABILITY

A compound having a 2-fluorophenyloxymethane structure according to the present invention is useful for organic

The invention claimed is:

1. A compound represented by general formula (1),

[Chem. 5]

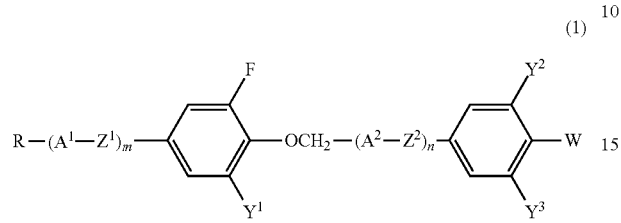

(1)

(in the formula, R represents an alkyl group having 1 to 15 carbon atoms or an alkenyl group having 2 to 15 carbon atoms, and one —CH$_2$— or two or more unadjacent —CH$_2$— present in the group may be substituted by —O—, —S—, —COO—, —OCO—, or —CO—;

A$^1$ and A$^2$ each independently represent a group selected from the group consisting of (a) a 1,4-cyclohexylene group (one —CH$_2$— or two or more unadjacent —CH$_2$— present in the group may be substituted by —O— or —S—), (b) a 1,4-phenylene group (one —CH= or two or more unadjacent —CH= present in the group may be substituted by —N=, and a hydrogen atom present in the group may be substituted by a fluorine atom), and (c) a naphthalene-2,6-diene group (a hydrogen atom present in the group may be substituted by a fluorine atom);

Z$^1$ and Z$^2$ each independently represent —CH$_2$O—, —OCH$_2$—, —CF$_2$O—, —OCF$_2$—, —CH$_2$CH$_2$—, —CF$_2$CF$_2$—, —CH=CH—, —CF=CF—, —C≡C—, or a single bond;

Y$^1$ represents a fluorine atom, and Y$^2$ and Y$^3$ each independently represent a hydrogen atom, a fluorine atom, or a chlorine atom;

W represents a fluorine atom, a chlorine atom, a cyano group, —CF$_3$—, —OCH$_2$F, —OCHF$_2$, or —OCF$_3$;

m and n each independently represent 0, 1, or 2, m+n is 0, 1, or 2, and when there is a plurality of each or any of A$^1$, A$^2$, Z$^1$, and Z$^2$, each or any of A$^1$, A$^2$, Z$^1$ and Z$^2$ may be the same or different).

2. The compound according to claim 1, wherein in the general formula (1), m represents 1 or 2, and n represents 0.

3. The compound according to claim 1, wherein in the general formula (1), m represents 0, and n represents 1 or 2.

4. The compound according to claim 1, wherein in the general formula (1), Z$^1$ and Z$^2$ each independently represent —CF$_2$O—, —OCF$_2$—, —CH$_2$CH$_2$—, or a single bond.

5. The compound according to claim 1, wherein in the general formula (1), A$^1$ and A$^2$ each independently represent a group selected from groups below

[Chem. 3]

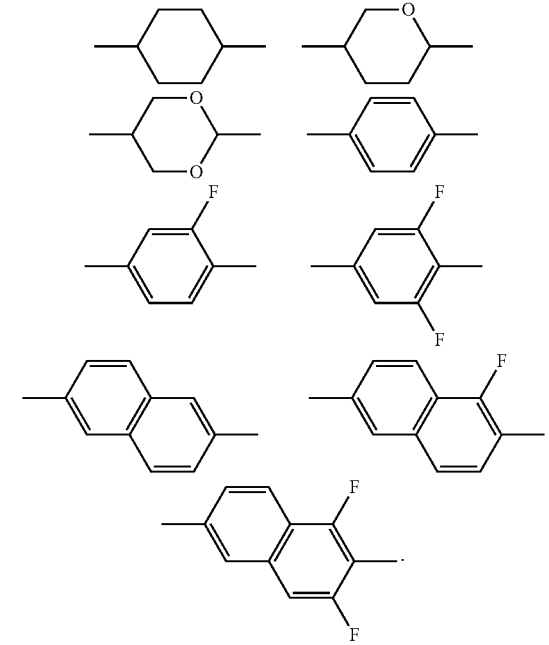

6. The compound according to claim 1, wherein in the general formula (1), A$^1$ and A$^2$ each independently represent a group selected from groups below

[Chem. 4]

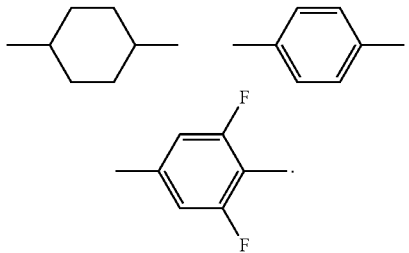

7. The compound according to claim 1, wherein in the general formula (1), Y$^2$ and Y$^3$ both represent fluorine atoms.

8. The compound according to claim 1, wherein in the general formula (1), W represents a fluorine atom, a —OCF$_3$ group, or a cyano group.

9. The compound according to claim 1, wherein in the general formula (1), W represents a —OCF$_3$ group and Y$^2$ and Y$^3$ both represent hydrogen atoms.

10. A liquid crystal composition containing at least one compound according to claim 1.

11. A liquid crystal display device using the liquid crystal composition according to claim 10.

* * * * *